(12) United States Patent
Whitehouse et al.

(10) Patent No.: US 7,524,878 B2
(45) Date of Patent: Apr. 28, 2009

(54) PHENYL SUBSTITUTED CARBOXYLIC ACIDS

(75) Inventors: Darren Whitehouse, Westbrook, CT (US); Shaojing Hu, Hamden, CT (US); Haiquan Fang, Madison, CT (US); Michael C. Van Zandt, Guilford, CT (US)

(73) Assignee: The Institute for Pharmaceuticals Discovery LLC, Branford, CT (US)

( * ) Notice: Subject to any disclaimer, the term of this patent is extended or adjusted under 35 U.S.C. 154(b) by 411 days.

(21) Appl. No.: 10/835,924

(22) Filed: Apr. 30, 2004

(65) Prior Publication Data

US 2005/0004369 A1  Jan. 6, 2005

Related U.S. Application Data

(60) Provisional application No. 60/466,868, filed on Apr. 30, 2003.

(51) Int. Cl.
*A61K 31/341* (2006.01)
*A61K 31/404* (2006.01)
*C07D 209/04* (2006.01)
*C07D 307/79* (2006.01)

(52) U.S. Cl. .......... 514/419; 514/468; 514/469; 548/490; 549/461; 549/462

(58) Field of Classification Search ........ 514/419, 514/468, 469; 548/490; 549/461, 462
See application file for complete search history.

(56) References Cited

U.S. PATENT DOCUMENTS

| | | | | |
|---|---|---|---|---|
| 4,243,678 A | * | 1/1981 | Krastinat | 514/563 |
| 6,054,260 A | * | 4/2000 | Adin et al. | 430/583 |
| 6,924,292 B2 | | 8/2005 | Kawano et al. | |

FOREIGN PATENT DOCUMENTS

| | | |
|---|---|---|
| WO | WO00/59506 | 10/2000 |
| WO | WO 0059506 | * 10/2000 |
| WO | WO01/70746 | 9/2001 |
| WO | WO 0170746 | * 9/2001 |

OTHER PUBLICATIONS

Murthy et al., Bioorg. & Med. Chem. (2002), vol. 10(7), pp. 2267-2282.*
Malamas et al., J. Med. Chem. (2000), vol. 43(7), pp. 1293-1310.*
Rodriguez et al., New J. Med. Chem. (1998), vol. 22(8), pp. 865-868.*

* cited by examiner

*Primary Examiner*—Taofiq A Solola
(74) *Attorney, Agent, or Firm*—McDonnell Boehnen Hulbert & Berghoff LLP

(57) ABSTRACT

Disclosed are compounds and pharmaceutically acceptable salts of formula (A):

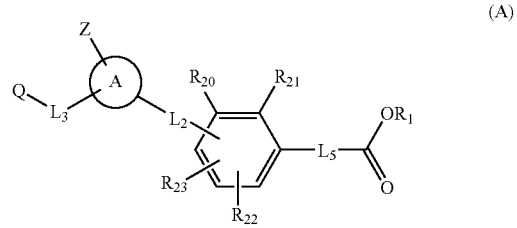

which are useful in the treatment of metabolic disorders related to insulin resistance, leptin resistance, or hyperglycemia. Compounds of the invention include inhibitors of Protein tyrosine phosphatases, in particular Protein tyrosine phosphatase-1B (PTP-1B), that are useful in the treatment of diabetes and other PTP mediated diseases, such as cancer, neurodegenerative diseases and the like. Also disclosed are pharmaceutical compositions comprising compounds of the invention and methods of treating the aforementioned conditions using such compounds.

50 Claims, No Drawings

SEQUENCE LISTING

```
<160> NUMBER OF SEQ ID NOS: 1

<210> SEQ ID NO 1
<211> LENGTH: 12
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: phosphotyrosine
<220> FEATURE:
<221> NAME/KEY: MISC_FEATURE
<222> LOCATION: (9)..(10)
<223> OTHER INFORMATION: phosphotyrosine

<400> SEQUENCE: 1

Thr Arg Asp Ile Tyr Glu Thr Asp Tyr Tyr Arg Lys
1               5                   10
```

PHENYL SUBSTITUTED CARBOXYLIC ACIDS

CROSS REFERENCE TO RELATED APPLICATIONS

This application claims priority from U.S. Provisional Application Ser. No. 60/466,868, filed Apr. 30, 2003, which is incorporated herein by reference in its entirety.

BACKGROUND OF THE INVENTION

1. Field of the Invention

The invention relates to phenyl substituted carboxylic acids and more specifically to such compounds that are useful in the treatment of syndrome X (consisting of such abnormalities as obesity, dyslipidemia, hypercoagulation, hypertension, insulin resistance and leading to heart disease and diabetes), obesity, diabetes, immunological disease, bleeding disorders and/or cancer. More specifically, it relates to such compounds that are capable of inhibiting Protein tyrosine phosphatases (PTPs), in particular Protein tyrosine phosphatase-1B (PTP-1B) which is a negative regulator of the insulin and leptin signaling pathway and improves insulin-sensitivity.

2. Description of the Related Art

This invention relates to a class of heterocycle substituted carboxylic acids that are inhibitors of various PTPs, in particular PTP-1B.

Protein tyrosine phosphatases are a large family of transmembrane or intracellular enzymes that dephosphorylate substrates involved in a variety of regulatory processes (Fischer et al., 1991, Science 253:401-406). Protein tyrosine phosphatase-1B (PTP-1B) is an approximately 50 kd intracellular protein, which is present in abundant amounts in various human tissues (Charbonneau et al., 1989, Proc. Natl. Acad. Sci. USA 86:5252-5256; Goldstein, 1993, Receptor 3:1-15).

Determining which proteins are substrates of PTP-1B has been of considerable interest. One substrate which has aroused especial interest is the insulin receptor. The binding of insulin to its receptor results in autophosphorylation of the domain. This causes activation of the insulin receptor tyrosine kinase, which phosphorylates the various insulin receptor substrate (IRS) proteins that propagate the insulin signaling event further downstream to mediate insulin's various biological effects.

Seely et al., 1996, Diabetes 45:1379-1385 ("Seely") studied the relationship of PTP-1B and the insulin receptor in vitro. Seely constructed a glutathione S-transferase (GST) fusion protein of PTP-1B that had a point mutation in the PTP-1B catalytic domain. Although catalytically inactive, this fusion protein was able to bind to the insulin receptor, as demonstrated by its ability to precipitate the insulin receptor from purified receptor preparations and from whole cell lysates derived from cells expressing the insulin receptor.

Ahmad et al., 1995, J. Biol. Chem. 270:20503-20508 used osmotic loading to introduce PTP-1B neutralizing antibodies into rat KRC-7 hepatoma cells. The presence of the antibody in the cells resulted in an increase of 42% and 38%, respectively, in insulin stimulated DNA synthesis and phosphatidyinositol 3' kinase activity. Insulin receptor autophosphorylation and insulin receptor substrate-1 tyrosine phosphorylation were increased 2.2 and 2.0-fold, respectively, in the antibody-loaded cells. The antibody-loaded cells also showed a 57% increase in insulin stimulated insulin receptor kinase activity toward exogenous peptide substrates.

Kennedy et al., 1999, Science 283: 1544-1548 showed that protein tyrosine phosphatase PTP-1B is a negative regulator of the insulin signaling pathway, indicating that inhibitors of this enzyme are beneficial in the treatment of Type 2 diabetes, which appears to involve a defect in an early process in insulin signal transduction rather than a structural defect in the insulin receptor itself. (J. M. Olefsky, W. T. Garvey, R. R. Henry, D. Brillon, S. Matthai and G. R. Freidenberg, G. R. (1988).) Cellular mechanisms of insulin resistance in non-insulin-dependent (Type II) diabetes. (Am. J. Med. 85: Suppl. 5A, 86-105.) A drug that improved insulin sensitivity would have several advantages over traditional therapy of NIDDM using sulfonylureas, which do not alleviate insulin resistance but instead compensate by increasing insulin secretion.

Ragab et al (2003, J. Biol. Chem 278(42), 40923-32) showed that PTP 1B is involved in regulating platelet aggregation. Hence, inhibition of PTP 1B can be predicted to have an effect on bleeding disorder, and cardiovascular disease.

Romsicki et al., (2003, Arch Biochem. Biophys 414(1), 40-50) showed that TC PTP is structurally and functionally very similar. A PTP 1B inhibitor is very likely to also inhibit TC PTP. A knockout of the TC PTP gene produces a phenotype with impaired immune function. (You-Ten et al., 1997, J. Exp. Med. 186(5), 683-93). Hence, inhibitors of PTP 1B can be predict to inhibit TC PTP and modulate immune response.

It has also been demonstrated that PT-P1B is a negative regulator of leptin signaling (Kaszua et al. MolCell. Endocrinology, 195:109-118, 2002). PTP-1B deficient mice show enhanced potency for exogenous leptin to suppress food intake (Cheng, et al. Developmental Cell 2:497-503, 2002). Thus, inhibitors of PTP-1B augment the beneficial effects of leptin on food intake, body weight regulation and metabolism, in normal individuals and leptin resistant individuals.

Therefore, inhibitors of PTPs, and inhibitors of PTP-LB in particular, are useful in controlling or treating obesity, syndrome X, Type 2 diabetes, in improving glucose tolerance, and in improving insulin sensitivity in patients in need thereof. Such compounds are also useful in treating or controlling other PTP mediated diseases, such as the treatment of cancer, neurodegenerative diseases, immunological disorders, bleeding and cardiovascular disorders, and the like.

SUMMARY OF THE INVENTION

In a broad aspect, the invention encompasses the compounds of formula (A) shown below, pharmaceutical compositions containing the compounds and methods employing such compounds or compositions in the treatment of diabetes and/or cancer.

The invention provides compounds of formula A:

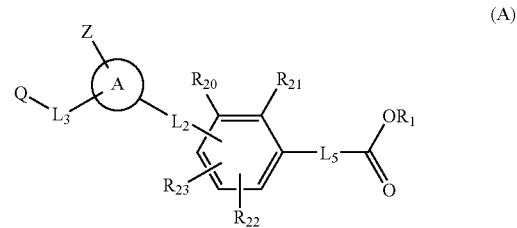

(A)

and pharmaceutically acceptable salts thereof, wherein, $R_1$ is H, $C_1$-$C_6$ alkyl, phenyl($C_1$-$C_6$)alkyl, or $C_2$-$C_6$ alkenyl;

$L_2$ is a bond or —C(O)$NR_{10}$—, —N($R_{10}$)C(O)—, —($C_1$-$C_4$) alkyl-N($R_{10}$)C(O)—, —C(O)N($R_{10}$)—($C_1$-$C_4$)alkyl-, —N(R$_{10}$)C(O)—(C$_1$-C$_4$)alkyl-, —(C$_1$-C$_4$)alkyl-C(O)N(R$_{10}$)—, —O—(C$_1$-C$_6$)alkyl-, or —(C$_1$-C$_6$)alkyl-O—;

L$_3$ is absent, a bond, —(C$_1$-C$_4$)alkyl-O—, —O—(C$_1$-C$_4$) alkyl-, —(C$_1$-C$_4$) alkyl-, -alkenyl-, -phenyl-;

L$_5$ is a bond, —O—(C$_1$-C$_6$)alkyl-, —(C$_1$-C$_6$)alkyl-O—, —C(O)N(R$_9$)—(C$_1$-C$_4$)alkyl-, —N(R$_9$)C(O)—(C$_1$-C$_4$) alkyl-, —(C$_1$-C$_4$) alkyl-C(O)N(R$_9$)—(C$_1$-C$_4$) alkyl-, —(C$_1$-C$_4$) alkyl-N(R$_9$)C(O)—(C$_1$-C$_4$) alkyl-, —N(R$_9$)—(C$_1$-C$_6$) alkyl-, —N(R$_9$)—(C$_1$-C$_6$) alkyl- wherein —(C$_1$-C$_6$) alkyl- is optionally substituted with phenyl, —(C$_1$-C$_4$) alkyl-N(R$_9$)—(C$_1$-C$_4$) alkyl-, —SO$_2$N(R$_9$)—, —SO$_2$N(R$_9$)—(C$_1$-C$_4$) alkyl-, —N(R$_9$)SO$_2$—(C$_1$-C$_4$) alkyl-, —N(R$_9$)SO$_2$—, —(C$_1$-C$_4$) alkyl-, —N(R$_9$)C(O)—, —C(O)—(C$_1$-C$_4$) alkyl-, —S—(C$_1$-C$_4$) alkyl-, or —(C$_1$-C$_4$) alkyl-S—(C$_1$-C$_4$) alkyl-, wherein R$_9$ and R$_{10}$ are independently is H, C$_1$-C$_6$ alkyl, C$_1$-C$_6$ alkoxycarbonyl, —SO$_2$-aryl, heteroarylalkyl, arylalkyl, wherein the aryl or heteroaryl groups are optionally substituted with 1, 2, 3, or 4 groups that are independently C$_1$-C$_4$ alkyl, C$_1$-C$_4$ alkoxy, halogen, OH, NO$_2$, NH$_2$, NH(C$_1$-C$_6$)alkyl, N(C$_1$-C$_6$)alkyl(C$_1$-C$_6$)alkyl, haloalkyl, or haloalkoxy;

R$_{20}$, R$_{21}$, R$_{22}$, and R$_{23}$ are independently selected from H, arylalkoxy, arylalkyl, halogen, alkyl, OH, alkoxy, NO$_2$, NH$_2$, CN, NH(C$_1$-C$_6$)alkyl, N(C$_1$-C$_6$)alkyl(C$_1$-C$_6$)alkyl, NH-aryl, NHC(O)—(C$_1$-C$_4$)alkyl-aryl, N(C$_1$-C$_4$ alkyl)C(O)—(C$_1$-C$_4$) alkyl-aryl, N(C$_1$-C$_4$)alkyl-aryl, —NHSO$_2$-aryl, —N(C$_1$-C$_4$alkyl)SO$_2$aryl, wherein the aryl group is optionally substituted with 1, 2, 3, 4, or 5 groups that are independently C$_1$-C$_6$ alkyl, C$_1$-C$_6$ alkoxy, halogen, OH, NO$_2$, haloalkyl, haloalkoxy;

the A ring is aryl, heteroaryl, heterocycloalkyl, each of which is optionally substituted with 1, 2, or 3 groups that are independently, halogen, C$_1$-C$_6$ alkyl, C$_1$-C$_6$ alkoxy, C$_1$-C$_4$ haloalkyl, C$_1$-C$_4$ haloalkoxy, NO$_2$, NH$_2$, NH(C$_1$-C$_6$)alkyl, or N(C$_1$-C$_6$)alkyl(C$_1$-C$_6$)alkyl;

Q is H, aryl, -aryl-carbonyl-aryl, -aryl-O-aryl, -aryl-alkyl-aryl, -aryl-heteroaryl, -aryl-heterocycloalkyl, -heteroaryl, -heteroaryl-alkyl-aryl, or -heterocycloalkyl, wherein the aforementioned cyclic groups are optionally substituted with 1, 2, 3, 4, or 5 groups that are independently alkoxycarbonyl, C$_1$-C$_6$ alkyl, C$_1$-C$_6$ alkoxy, halogen, haloalkyl, haloalkoxy, NR$_6$R$_7$, phenyl, phenyl-(C$_1$-C$_6$)alkyl-, or phenyloxy-; wherein R$_6$ and R$_7$ are independently H, C$_1$-C$_6$ alkyl, aryl(C$_1$-C$_6$) alkyl, C$_2$-C$_6$ alkanoyl, aryl C$_2$-C$_6$ alkanoyl, C$_1$-C$_6$ alkoxycarbonyl, aryl C$_1$-C$_6$ alkoxycarbonyl, heteroarylcarbonyl, heteroaryl, heterocycloalkylcarbonyl, —C(O)NH$_2$, —C(O)NH(C$_1$-C$_6$)alkyl, —C(O)N(C$_1$-C$_6$)alkyl(C$_1$-C$_6$) alkyl, or —SO$_2$-aryl, wherein the cyclic groups are optionally substituted with 1, 2, 3, or 4 groups that are independently halogen, C$_1$-C$_4$ alkyl, C$_1$-C$_4$ alkoxy, NO$_2$, OH, NH$_2$, NH(C$_1$-C$_6$)alkyl, N(C$_1$-C$_6$)alkyl(C$_1$-C$_6$)alkyl, haloalkyl or haloalkoxy;

and

Z is absent, H, —NHC(O)aryl, —N(C$_1$-C$_4$ alkyl)C(O)aryl, or aryl (phenyl), wherein the aryl groups are optionally substituted with 1, 2, 3, 4, or 5 groups that are independently C$_1$-C$_6$ alkyl, C$_1$-C$_6$ alkoxy, halogen, haloalkyl, haloalkoxy, or NO$_2$, or Z is —NHC(O)—(C$_1$-C$_4$)alkyl-(C$_3$-C$_7$)cycloalkyl, —N(C$_1$-C$_4$)alkylC(O)—(C$_1$-C$_4$)alkyl-(C$_3$-C$_7$)cycloalkyl.

The compounds of formula A bind to PTPs, and in particular to PTP-1B. The interaction with the enzyme, specifically PTP-1B, preferably results in inhibition of the enzyme.

The invention also includes intermediates that are useful in making the compounds of the invention.

The invention also provides pharmaceutical compositions comprising a compound or salt of formula A and at least one pharmaceutically acceptable carrier, solvent, adjuvant or diluent.

The invention further provides methods of treating disease such as diabetes, syndrome X, cancer, immunological disease, bleeding disorders, or cardiovascular disease in a patient in need of such treatment, comprising administering to the patient a compound or pharmaceutically acceptable salt of formula A, or a pharmaceutical composition comprising a compound or salt of formula A.

In another aspect, the invention provides a method for inhibiting protein tyrosine phosphatases, preferably PTP-1B, comprising administering a therapeutically effective amount of a compound of formula A.

In another aspect, the invention provides a method for treating metabolic disorders related to insulin resistance or hyperglycemia, comprising administering to a patient in need of such treatment a therapeutically effective amount of a compound of formula A.

The invention also provides the use of a compound or salt according to formula A for the manufacture of a medicament for use in treating diabetes or cancer or other diseases related to PTP.

The invention also provides methods of preparing the compounds of the invention and the intermediates used in those methods.

The invention also provides methods and compositions for combination therapy of Type I and Type II diabetes. In these embodiments, the invention provides formulations and pharmaceutical compositions, as well as methods for treating Type I and Type II diabetes with the compounds of formula A plus additional compounds and medicaments as disclosed in more detail below. In these embodiments, the methods of the invention can comprise treatment methods for Type I and Type II diabetes where the compounds of formula A are formulated with a therapeutically-effective amount of said additional compounds and medicaments. In alternative embodiments, treatment methods of the invention for Type I and Type II diabetes comprise administration of the inventive compounds of formula A as disclosed herein concomitantly, simultaneously or together with a therapeutically-effective amount of said additional compounds and medicaments.

DETAILED DESCRIPTION OF THE INVENTION

A preferred class of compounds of formula A are compounds of formula I:

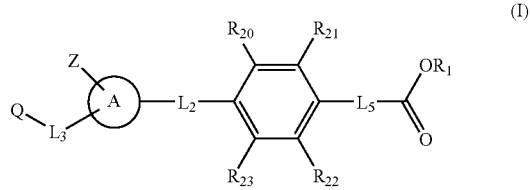

(I)

Preferred compounds of formula I are compounds of formula I-a, wherein,

Q is H, phenyl, -phenyl-O-phenyl, -phenyl-carbonyl-phenyl, -phenyl-(C$_1$-C$_4$)alkyl-phenyl, -phenyl-pyridyl, -phenyl-pyrimidyl, -phenyl-benzofuranyl, -phenyl-indolyl, -phenyl-piperidinyl, -phenyl-pyrrolidinyl, -phenyl-piperazinyl, indolizinyl, benzofuranyl, indolyl, dibenzofuranyl, -benzothienyl-$(C_1-C_4)$alkyl-phenyl, -indolyl-$(C_1-C_4)$alkyl-phenyl, benzofuranyl-$(C_1-C_4)$ alkyl-phenyl, piperidinyl, pyrrolidinyl, tetrahydroisoquinolinyl, or imidazo[2,1-b] thiazol-3-one, wherein the aforementioned cyclic groups are optionally substituted with 1, 2, 3, 4, or 5 groups that are independently alkoxycarbonyl, $C_1-C_6$ alkyl, $C_1-C_6$ alkoxy, halogen, haloalkyl, haloalkoxy, $NR_6R_7$, phenyl, or phenyl-$(C_1-C_6)$alkyl-; wherein $R_6$ and $R_7$ are independently H, $C_1-C_6$ alkyl, phenyl$(C_1-C_6)$ alkyl, $C_2-C_6$ alkanoyl, phenyl$(C_2-C_6)$alkanoyl, $C_1-C_6$ alkoxycarbonyl, phenyl$(C_1-C_6)$alkoxycarbonyl, heteroarylcarbonyl, heteroaryl, heterocycloalkylcarbonyl, —C(O)NH$_2$, —C(O)NH($C_1-C_6$)alkyl, —C(O)N($C_1-C_6$) alkyl($C_1-C_6$)alkyl, or —SO$_2$-aryl, wherein the cyclic groups are optionally substituted with 1, 2, 3, or 4 groups that are independently halogen, $C_1-C_4$ alkyl, $C_1-C_4$ alkoxy, NO$_2$, OH, NH$_2$, NH($C_1-C_6$)alkyl, N($C_1-C_6$)alkyl($C_1-C_6$) alkyl, haloalkyl or haloalkoxy; and Z is absent, H, or phenyl, wherein the phenyl group is optionally substituted with 1, 2, 3, 4, or 5 groups that are independently $C_1-C_6$ alkyl, $C_1-C_6$ alkoxy, halogen, $C_1-C_4$ haloalkyl, $C_1-C_4$ haloalkoxy, or NO$_2$.

A preferred class of compounds of formula I-a are compounds of formula I-b, wherein, the A ring is phenyl, pyrido[1,2-a]indolyl, furanyl, thienyl, benzofuranyl, dibenzofuranyl, indolyl, thiazolyl, thiazolidinyl, each of which is optionally substituted with 1, 2, or 3 groups that are independently, halogen, $C_1-C_6$ alkyl, $C_1-C_6$ alkoxy, $C_1-C_4$ haloalkyl, $C_1-C_4$ haloalkoxy, NO$_2$, NH$_2$, NH($C_1-C_6$)alkyl, or N($C_1-C_6$)alkyl($C_1-C_6$)alkyl; and $R_{20}$, $R_{21}$, $R_{22}$, and $R_{23}$ are independently selected from H, phenyl$(C_1-C_6)$alkoxy, phenyl$(C_1-C_6)$alkyl, halogen, ($C_1-C_6$)alkyl, OH, alkoxy, CN, NO$_2$, NH$_2$, NH($C_1-C_6$)alkyl, N($C_1-C_6$)alkyl($C_1-C_6$)alkyl, NH-phenyl, NHC(O)—($C_1-C_4$) alkyl-phenyl, N($C_1-C_4$ alkyl)C(O)—($C_1-C_4$)alkyl-phenyl, N($C_1-C_4$)alkyl-phenyl, —NHSO$_2$-phenyl, —N($C_1-C_4$alkyl)SO$_2$phenyl, wherein the phenyl group is optionally substituted with 1, 2, 3, 4, or 5 groups that are independently $C_1-C_6$ alkyl, $C_1-C_6$ alkoxy, halogen, OH, NO$_2$, $C_1-C_4$ haloalkyl, $C_1-C_4$ haloalkoxy.

A preferred class of compounds of formula I-b are compounds of formula I-c, wherein, $R_1$ is H, $C_1-C_6$ alkyl, benzyl, or allyl;

$L_2$ is a bond or —C(O)NR$_{10}$—, —N(R$_{10}$)C(O)—, —($C_1-C_4$) alkyl-N(R$_{10}$)C(O)—, —C(O)N(R$_{10}$)—($C_1-C_4$)alkyl-, —N(R$_{10}$)C(O)—($C_1-C_4$)alkyl-, —($C_1-C_4$)alkyl-C(O)N (R$_{10}$)—, —O—($C_1-C_6$)alkyl-, or —($C_1-C_6$)alkyl-O—;

$L_3$ is absent, a bond, —($C_1-C_4$)alkyl-O—, —O—($C_1-C_4$) alkyl, —($C_1-C_4$) alkyl-, -alkenyl-, or -phenyl-;

$L_5$ is a bond, —O—($C_1-C_6$)alkyl-, —($C_1-C_6$)alkyl-O—, —C(O)N(R$_9$)—($C_1-C_4$) alkyl-, —N(R$_9$)C(O)—($C_1-C_4$) alkyl-, —N(R$_9$)—($C_1-C_6$) alkyl-, —N(R$_9$)—($C_1-C_6$) alkyl- wherein —($C_1-C_6$) alkyl- is optionally substituted with phenyl, —($C_1-C_4$) alkyl-N(R$_9$), —($C_1-C_4$) alkyl-N (R$_9$)—($C_1-C_4$) alkyl-, —SO$_2$N(R$_9$)—, —SO$_2$N(R$_9$)—($C_1-C_4$) alkyl-, —N(R$_9$)SO$_2$—($C_1-C_4$)alkyl-, —N(R$_9$) SO$_2$—, —($C_1-C_4$) alkyl-, —N(R$_9$)—($C_1-C_6$) alkyl-wherein —($C_1-C_6$) alkyl- is optionally substituted with phenyl, —N(R$_9$)C(O)—, —C(O)—($C_1-C_4$) alkyl-, —S—($C_1-C_4$) alkyl-, or —($C_1-C_4$) alkyl-S—($C_1-C_4$) alkyl-, wherein $R_9$ and $R_{10}$ are independently is H, $C_1-C_6$ alkyl, $C_1-C_6$ alkoxycarbonyl, —SO$_2$phenyl, —$C_1-C_6$ alkyl-furanyl, —$C_1-C_6$ alkyl-tetrazolyl, —$C_1-C_6$-alkyl thienyl, —$C_1-C_6$-alkyl pyrrolyl, —$C_1-C_6$-alkyl pyridyl, benzyl, wherein the aryl and heteroaryl groups are optionally substituted with 1, 2, 3, or 4 groups that are independently $C_1-C_4$ alkyl, $C_1-C_4$ alkoxy, halogen, OH, NO$_2$, NH$_2$, NH($C_1-C_6$)alkyl, N($C_1-C_6$)alkyl($C_1-C_6$)alkyl, $C_1-C_4$ haloalkyl, or $C_1-C_4$ haloalkoxy.

A preferred class of compounds of formula I-c are compounds of formula I-d, wherein, $L_2$ is a bond or —C(O)NR$_{10}$-, —N(R$_{10}$)C(O)—, —($C_1-C_4$) alkyl-C(O)N(R$_{10}$)—, —O—($C_1-C_6$)alkyl-, or —($C_1-C_6$) alkyl-O—;

the A ring is phenyl, pyrido[1,2-a]indolyl, furanyl, thienyl, indolyl, thiazolyl, thiazolidinyl, each of which is optionally substituted with 1, 2, or 3 groups that are independently, halogen, $C_1-C_6$ alkyl, $C_1-C_6$ alkoxy, $C_1-C_2$ haloalkyl, $C_1-C_2$ haloalkoxy, NO$_2$, NH$_2$, NH($C_1-C_6$)alkyl, or N($C_1-C_6$)alkyl($C_1-C_6$)alkyl;

Z is phenyl, optionally substituted with 1, 2, 3, 4, or 5 groups that are independently $C_1-C_6$ alkyl, $C_1-C_6$ alkoxy, halogen, $C_1-C_4$ haloalkyl, $C_1-C_4$ haloalkoxy, or NO$_2$.

A preferred class of compounds of formulas I-c or I-d are compounds of formula I-e, wherein, $R_{22}$ and $R_{23}$ are both H;

$L_5$ is a bond, —SO$_2$N(R$_9$)—, —SO$_2$N(R$_9$)—($C_1-C_4$)alkyl-, —N(R$_9$)SO$_2$—($C_1-C_4$)alkyl-, or —N(R$_9$)SO$_2$—; and Q is phenyl, -phenyl-O-phenyl, indolizinyl, benzofuranyl, indolyl, dibenzofuranyl, -benzothienyl-($C_1-C_4$)alkyl-phenyl, -indolyl-($C_1-C_4$)alkyl-phenyl, or benzofuranyl-($C_1-C_4$)alkyl-phenyl, wherein the aforementioned cyclic groups are optionally substituted with 1, 2, 3, 4, or 5 groups that are independently alkoxycarbonyl, $C_1-C_6$ alkyl, $C_1-C_6$ alkoxy, halogen, haloalkyl, haloalkoxy, NR$_6$R$_7$, phenyl, or phenyl-($C_1-C_6$)alkyl-.

A preferred class of compounds of formula I-e are compounds of formula I-f, wherein, $R_9$ is H, $C_1-C_6$ alkyl, $C_1-C_6$ alkoxycarbonyl, —SO$_2$phenyl, —$C_1-C_6$ alkyl-furanyl, —$C_1-C_6$ alkyl-tetrazolyl, —$C_1-C_6$-alkyl thienyl, —$C_1-C_6$- alkyl pyrrolyl, —$C_1-C_6$- alkyl pyridyl, benzyl, wherein the aryl and heteroaryl groups are optionally substituted with 1, 2, 3, or 4 groups that are independently $C_1-C_4$ alkyl, $C_1-C_4$ alkoxy, halogen, OH, NO$_2$, NH$_2$, NH($C_1-C_6$)alkyl, N($C_1-C_6$)alkyl($C_1-C_6$)alkyl, $C_1-C_2$ haloalkyl (preferably CF$_3$), or $C_1-C_4$ haloalkoxy (preferably OCF$_3$); and $L_3$ is a bond, —($C_1-C_4$)alkyl-O—, —O—($C_1-C_4$)alkyl, —($C_1-C_4$) alkyl-, -alkenyl-, or -phenyl-.

A preferred class of compounds of formula I-f are compounds of formula I-g, wherein, $L_2$ is a bond or —C(O)NR$_{10}$—, —N(R$_{10}$)C(O)—, —O—($C_1-C_6$)alkyl-, or —($C_1-C_6$)alkyl-O—;

the A ring is phenyl, furanyl, indolyl, thiazolyl, each of which is optionally substituted with 1, 2, or 3 groups that are independently, halogen, $C_1-C_6$ alkyl, $C_1-C_6$ alkoxy, $C_1-C_2$ haloalkyl, $C_1-C_2$ haloalkoxy, NO$_2$, NH$_2$, NH($C_1-C_6$)alkyl, or N($C_1-C_6$)alkyl($C_1-C_6$)alkyl;

Q is phenyl, -phenyl-O-phenyl, benzofuranyl, indolyl, dibenzofuranyl, or benzofuranyl-CH$_2$-phenyl, wherein the aforementioned cyclic groups are optionally substituted with 1, 2, 3, 4, or 5 groups that are independently $C_1-C_6$ alkoxycarbonyl, $C_1-C_6$ alkyl, $C_1-C_6$ alkoxy, halogen, CF$_3$, OCF$_3$, NR$_6$R$_7$, phenyl, or phenyl-($C_1-C_6$)alkyl-; wherein $R_6$ and $R_7$ are independently H, $C_1-C_6$ alkyl, benzyl, $C_2-C_6$ alkanoyl, phenyl($C_1-C_6$)alkanoyl, $C_1-C_6$ alkoxycarbonyl, or —SO$_2$-phenyl, wherein the cyclic groups are optionally substituted with 1, 2, 3, or 4 groups that are independently halogen, $C_1-C_4$ alkyl, $C_1-C_4$ alkoxy, NO$_2$, OH, NH$_2$, NH($C_1-C_6$)alkyl, N($C_1-C_6$)alkyl($C_1-C_6$)alkyl, CF$_3$, or OCF$_3$; and Z is phenyl, optionally substituted with 1, 2, or 3 groups that are independently $C_1$-$C_6$ alkyl, $C_1$-$C_6$ alkoxy, halogen, $CF_3$, $OCF_3$, or $NO_2$.

A preferred class of compounds of formula I-e are compounds of formula I-h, wherein, $L_3$ is a bond, —($C_1$-$C_4$)alkyl-O—, —O—($C_1$-$C_4$)alkyl, —($C_1$-$C_4$) alkyl-;

$L_5$ is —$SO_2$N($R_9$)—, —$SO_2$N($R_9$)—($C_1$-$C_4$) alkyl-, —N($R_9$)$SO_2$—($C_1$-$C_4$)alkyl-, or —N($R_9$)$SO_2$—;

$R_1$ is H or $C_1$-$C_6$ alkyl;

$R_{21}$ is H; and $R_{22}$ is H, phenyl($C_1$-$C_6$)alkoxy, benzyl, halogen, ($C_1$-$C_6$) alkyl, OH, $C_1$-$C_6$ alkoxy, $NO_2$, $NH_2$, NH($C_1$-$C_6$)alkyl, or N($C_1$-$C_6$)alkyl($C_1$-$C_6$)alkyl, wherein the phenyl group is optionally substituted with 1, 2, 3, 4, or 5 groups that are independently $C_1$-$C_6$ alkyl, $C_1$-$C_6$ alkoxy, halogen, OH, $NO_2$, $CF_3$ or $OCF_3$.

A preferred class of compounds of formula I-h are compounds of formula I-i, wherein, the A ring is phenyl, indolyl, or thiazolyl, each of which is optionally substituted with 1, or 2 groups that are independently, halogen, $C_1$-$C_6$ alkyl, $C_1$-$C_6$ alkoxy, $CF_3$, $OCF_3$, $NO_2$, $NH_2$, NH($C_1$-$C_6$)alkyl, or N($C_1$-$C_6$)alkyl($C_1$-$C_6$)alkyl;

Q is phenyl, -phenyl-O-phenyl, benzofuranyl, dibenzofuranyl, or benzofuranyl-$CH_2$-phenyl, wherein the aforementioned cyclic groups are optionally substituted with 1, 2, or 3 groups that are independently $C_1$-$C_6$ alkoxycarbonyl, $C_1$-$C_6$ alkyl, $C_1$-$C_6$ alkoxy, halogen, $CF_3$, $OCF_3$, $NH_2$, NH($C_1$-$C_6$)alkyl, or N($C_1$-$C_6$)alkyl($C_1$-$C_6$)alkyl.

A preferred class of compounds of formula I-c are compounds of formula II, (II)

wherein n is 0, 1, 2, 3, or 4; and each $R_{10}$ is independently, halogen, $C_1$-$C_6$ alkyl, $C_1$-$C_6$ alkoxy, $C_1$-$C_4$ haloalkyl, $C_1$-$C_4$ haloalkoxy, $NO_2$, $NH_2$, NH($C_1$-$C_6$)alkyl, or N($C_1$-$C_6$)alkyl($C_1$-$C_6$)alkyl $R_1$ is H, $C_1$-$C_6$ alkyl, or benzyl;

Q is H, phenyl, -phenyl-O-phenyl, -phenyl-($C_1$-$C_4$)alkyl-phenyl, -phenyl-pyridyl, -phenyl-pyrimidyl, -phenyl-benzofuranyl, -phenyl-indolyl, -phenyl-piperidinyl, -phenyl-pyrrolidinyl, -phenyl-piperazinyl, indolizinyl, benzofuranyl, indolyl, dibenzofuranyl, -benzothienyl-($C_1$-$C_4$)alkyl-phenyl, -indolyl-($C_1$-$C_4$)alkyl-phenyl, benzofuranyl-($C_1$-$C_4$)alkyl-phenyl, piperidinyl, pyrrolidinyl, tetrahydroisoquinolinyl, or imidazo[2,1-b]thiazol-3-one, wherein the aforementioned cyclic groups are optionally substituted with 1, 2, 3, 4, or 5 groups that are independently alkoxycarbonyl, $C_1$-$C_6$ alkyl, $C_1$-$C_6$ alkoxy, halogen, haloalkyl, haloalkoxy, $NR_6R_7$, phenyl, or phenyl-($C_1$-$C_6$)alkyl-;

$L_2$ is a bond or —C(O)$NR_{10}$-, —N($R_{10}$)C(O)—, —($C_1$-$C_4$) alkyl-N($R_{10}$)C(O)—, —C(O)N($R_{10}$)—($C_1$-$C_4$)alkyl-, —N($R_{10}$)C(O)—($C_1$-$C_4$)alkyl-C(O)N($R_{10}$)—, —O—($C_1$-$C_4$)alkyl-, or —($C_1$-$C_4$)alkyl-O—;

$R_9$ and $R_{10}$ are independently is H, $C_1$-$C_6$ alkyl, —$SO_2$phenyl, —$CH_2$-furanyl, —$CH_2$-tetrazolyl, benzyl, wherein the aryl and heteroaryl groups are optionally substituted with 1, 2, 3, or 4 groups that are independently $C_1$-$C_4$ alkyl, $C_1$-$C_4$ alkoxy, halogen, OH, $NO_2$, $NH_2$, NH($C_1$-$C_6$)alkyl, N($C_1$-$C_6$)alkyl($C_1$-$C_6$) alkyl, $C_1$-$C_4$ haloalkyl, or $C_1$-$C_4$ haloalkoxy.

Preferred compounds of formula II include compounds of formula II-a, wherein $L_3$ is a bond, —($C_1$-$C_4$)alkyl-O—, —O—($C_1$-$C_4$)alkyl, or —($C_1$-$C_4$)alkyl-; and $R_{20}$ and $R_{21}$ are independently selected from H, phenyl($C_1$-$C_6$)alkoxy, phenyl($C_1$-$C_6$)alkyl, halogen, ($C_1$-$C_6$)alkyl, OH, $C_1$-$C_6$ alkoxy, $NO_2$, $NH_2$, NH($C_1$-$C_6$)alkyl, N($C_1$-$C_6$) alkyl($C_1$-$C_6$)alkyl, wherein the phenyl group is optionally substituted with 1, 2, 3, 4, or 5 groups that are independently $C_1$-$C_6$ alkyl, $C_1$-$C_6$ alkoxy, halogen, OH, $NO_2$, $C_1$-$C_2$ haloalkyl, or $C_1$-$C_2$ haloalkoxy.

Preferred compounds of formula II-a include compounds of formula II-b, wherein $R_1$ is H, or $C_1$-$C_6$ alkyl, Q is H, phenyl, -phenyl-O-phenyl, indolizinyl, benzofuranyl, indolyl, dibenzofuranyl, -benzothienyl-($C_1$-$C_4$)alkyl-phenyl, -indolyl-($C_1$-$C_4$)alkyl-phenyl, benzofuranyl-($C_1$-$C_4$) alkyl-phenyl, piperidinyl, pyrrolidinyl, tetrahydroisoquinolinyl, or imidazo[2,1-b]thiazol-3-one, wherein the aforementioned cyclic groups are optionally substituted with 1, 2, 3, 4, or 5 groups that are independently alkoxycarbonyl, $C_1$-$C_6$ alkyl, $C_1$-$C_6$ alkoxy, halogen, haloalkyl, haloalkoxy, $NR_6R_7$, phenyl, or phenyl-($C_1$-$C_6$)alkyl-.

Preferred class of compounds of formula II-b include compounds of formula III, (III)

wherein n is 0, 1, 2, 3, or 4; and each $R_{10}$ is independently, halogen, $C_1$-$C_6$ alkyl, $C_1$-$C_6$ alkoxy, $C_1$-$C_4$ haloalkyl, $C_1$-$C_4$ haloalkoxy, $NO_2$, $NH_2$, NH($C_1$-$C_6$)alkyl, or N($C_1$-$C_6$)alkyl($C_1$-$C_6$)alkyl.

Preferred compounds of formula III include compounds of formula III-a, wherein $L_3$ is a bond or —$C_1$-$C_4$ alkyl-; and $L_5$ is a bond, —O—($C_1$-$C_6$)alkyl-, —($C_1$-$C_6$)alkyl-O—, —C(O)N($R_9$)—($C_1$-$C_4$) alkyl-, —N($R_9$)C(O)—($C_1$-$C_4$) alkyl-, —N($R_9$)—($C_1$-$C_6$) alkyl-, —($C_1$-$C_4$) alkyl-N($R_9$), —($C_1$-$C_4$) alkyl-N($R_9$)—($C_1$-$C_4$) alkyl-, —$SO_2$N($R_9$)—, —$SO_2$N($R_9$)—($C_1$-$C_4$) alkyl-, —N($R_9$)$SO_2$-($C_1$-$C_4$) alkyl-, —N($R_9$)$SO_2$—, —($C_1$-$C_4$) alkyl-, —N($R_9$)C(O)—, —C(O)—($C_1$-$C_4$) alkyl-, —S—($C_1$-$C_4$) alkyl-, or —($C_1$-$C_4$) alkyl-S—($C_1$-$C_4$) alkyl-.

Preferred compounds of formula III-a include compounds of formula III-b, wherein $L_5$ is a bond, —O—($C_1$-$C_6$)alkyl-, —($C_1$-$C_6$)alkyl-O—, —($C_1$-$C_4$) alkyl-, —C(O)—($C_1$-$C_4$) alkyl-, —S—($C_1$-$C_4$) alkyl-, or —($C_1$-$C_4$) alkyl-S—($C_1$-$C_4$) alkyl-.

Preferred compounds of formula III-b include compounds of formula III-c, wherein $R_1$ and $R_{21}$ are both H; and $R_{22}$ is H, phenyl($C_1$-$C_6$)alkoxy, benzyl, halogen, ($C_1$-$C_6$) alkyl, OH, $C_1$-$C_6$ alkoxy, $NO_2$, $NH_2$, NH($C_1$-$C_6$)alkyl, or N($C_1$-$C_6$)alkyl($C_1$-$C_6$)alkyl, wherein the phenyl group is optionally substituted with 1, 2, 3, 4, or 5 groups that are independently $C_1$-$C_6$ alkyl, $C_1$-$C_6$ alkoxy, halogen, OH, $NO_2$, $C_1$-$C_2$ haloalkyl, or $C_1$-$C_2$ haloalkoxy.

Preferred compounds of formula III-c include compounds of formula III-d, wherein $L_5$ is —O—($C_1$-$C_6$)alkyl- or —($C_1$-$C_6$)alkyl-O—.

Preferred compounds of formula III-c include compounds of formula III-e, wherein $L_5$ is —($C_1$-$C_4$)alkyl- or —C(O)—($C_1$-$C_4$) alkyl-. In another aspect, $L_5$ is —$CH_2$—.

Preferred compounds of formula III-c include compounds of formula III-f, wherein $L_5$ is —S—($C_1$-$C_4$)alkyl- or —($C_1$-$C_4$)alkyl-S—($C_1$-$C_4$) alkyl-. In another aspect, $L_5$ is —S—($C_1$-$C_2$)alkyl-.

Preferred compounds of formula III-a include compounds of formula III-g, wherein $L_5$ is —C(O)N($R_9$)—($C_1$-$C_4$) alkyl-, —N($R_9$)C(O)—($C_1$-$C_4$) alkyl-, —N($R_9$)—($C_1$-$C_6$) alkyl-, —($C_1$-$C_4$) alkyl-N($R_9$), —($C_1$-$C_4$) alkyl-N($R_9$)-($C_1$-$C_4$) alkyl-, —$SO_2$N($R_9$)—, —$SO_2$N($R_9$)—($C_1$-$C_4$) alkyl-, —N($R_9$)$SO_2$—($C_1$-$C_4$)alkyl-, —N($R_9$)$SO_2$—, —N($R_9$)C(O)—, wherein $R_9$ is H, $C_1$-$C_6$ alkyl, —$SO_2$phenyl, —$C_1$-$C_6$ alkyl-furanyl, —$C_1$-$C_6$ alkyl-tetrazolyl, —$C_1$-$C_6$-alkyl thienyl, —$C_1$-$C_6$-alkyl pyrrolyl, —$C_1$-$C_6$-alkyl pyridyl, benzyl, wherein the aryl and heteroaryl groups are optionally substituted with 1, 2, 3, or 4 groups that are independently $C_1$-$C_4$ alkyl, $C_1$-$C_4$ alkoxy, halogen, OH, $NO_2$, $NH_2$, NH($C_1$-$C_6$)alkyl, N($C_1$-$C_6$)alkyl($C_1$-$C_6$)alkyl, $C_1$-$C_4$ haloalkyl, or $C_1$-$C_4$ haloalkoxy.

Preferred compounds of formula III-g include compounds of formula III-h, wherein $R_1$ and $R_{21}$ are both H; and $R_{22}$ is H, phenyl($C_1$-$C_6$)alkoxy, benzyl, halogen, ($C_1$-$C_6$) alkyl, OH, $C_1$-$C_6$ alkoxy, $NO_2$, $NH_2$, NH($C_1$-$C_6$)alkyl, or N($C_1$-$C_6$)alkyl($C_1$-$C_6$)alkyl, wherein the phenyl group is optionally substituted with 1, 2, 3, 4, or 5 groups that are independently $C_1$-$C_6$ alkyl, $C_1$-$C_6$ alkoxy, halogen, OH, $NO_2$, $C_1$-$C_2$ haloalkyl, or $C_1$-$C_2$ haloalkoxy.

Preferred compounds of formula III-h include compounds of formula III-i, wherein $R_9$ is H, $C_1$-$C_6$ alkyl, —$SO_2$phenyl, —$C_1$-$C_4$ alkyl-furanyl, —$C_1$-$C_4$ alkyl-tetrazolyl, —$C_1$-$C_4$- alkyl thienyl, —$C_1$-$C_4$- alkyl pyrrolyl, —$C_1$-$C_4$- alkyl pyridyl, benzyl, wherein the aryl and heteroaryl groups are optionally substituted with 1, 2, 3, or 4 groups that are independently $C_1$-$C_4$ alkyl, $C_1$-$C_4$ alkoxy, halogen, OH, $NO_2$, $NH_2$, NH($C_1$-$C_6$)alkyl, N($C_1$-$C_6$)alkyl($C_1$-$C_6$)alkyl, $CF_3$, or $OCF_3$.

Preferred compounds of formula III-i include compounds of formula III-j, wherein $L_5$ is —C(O)N($R_9$)—($C_1$-$C_4$) alkyl-, —N($R_9$)C(O)—($C_1$-$C_4$) alkyl-, or —N($R_9$)C(O)—.

Preferred compounds of formula III-j include compounds of formula III-k, wherein $R_9$ is H, $C_1$-$C_6$ alkyl, or benzyl, wherein phenyl group is optionally substituted with 1, 2, 3, or 4 groups that are independently $C_1$-$C_4$ alkyl, $C_1$-$C_4$ alkoxy, halogen, OH, $NO_2$, $NH_2$, NH($C_1$-$C_6$)alkyl, N($C_1$-$C_6$)alkyl($C_1$-$C_6$)alkyl, $CF_3$, or $OCF_3$.

Preferred compounds of formula III-j include compounds of formula III-l, wherein $R_9$ is H, —$SO_2$phenyl, —$C_1$-$C_4$ alkyl-furanyl, —$C_1$-$C_4$ alkyl-tetrazolyl, —$C_1$-$C_4$- alkyl thienyl, —$C_1$-$C_4$- alkyl pyrrolyl, —$C_1$-$C_4$- alkyl pyridyl, wherein the aryl and heteroaryl groups are optionally substituted with 1, 2, 3, or 4 groups that are independently $C_1$-$C_4$ alkyl, $C_1$-$C_4$ alkoxy, halogen, OH, $NO_2$, $NH_2$, NH($C_1$-$C_6$)alkyl, N($C_1$-$C_6$)alkyl($C_1$-$C_6$)alkyl, $CF_3$, or $OCF_3$.

Preferred compounds of formula III-i include compounds of formula III-m, wherein $L_5$ is —N($R_9$)—($C_1$-$C_6$) alkyl-, —($C_1$-$C_4$) alkyl-N($R_9$), or —($C_1$-$C_4$) alkyl-N($R_9$)—($C_1$-$C_4$) alkyl-.

Preferred compounds of formula III-m include compounds of formula III-n, wherein $R_9$ is H, $C_1$-$C_6$ alkyl, or benzyl, wherein phenyl group is optionally substituted with 1, 2, 3, or 4 groups that are independently $C_1$-$C_4$ alkyl, $C_1$-$C_4$ alkoxy, halogen, OH, $NO_2$, $NH_2$, NH($C_1$-$C_6$)alkyl, N($C_1$-$C_6$)alkyl($C_1$-$C_6$)alkyl, $CF_3$, or $OCF_3$.

Preferred compounds of formula III-m include compounds of formula III-o, wherein $R_9$ is H, —$SO_2$phenyl, —$C_1$-$C_4$ alkyl-furanyl, —$C_1$-$C_4$ alkyl-tetrazolyl, —$C_1$-$C_4$- alkyl thienyl, —$C_1$-$C_4$- alkyl pyrrolyl, —$C_1$-$C_4$- alkyl pyridyl, wherein the aryl and heteroaryl groups are optionally substituted with 1, 2, 3, or 4 groups that are independently $C_1$-$C_4$ alkyl, $C_1$-$C_4$ alkoxy, halogen, OH, $NO_2$, $NH_2$, NH($C_1$-$C_6$)alkyl, N($C_1$-$C_6$)alkyl($C_1$-$C_6$) alkyl, $CF_3$, or $OCF_3$.

Preferred compounds of formula III-i include compounds of formula III-p, wherein $L_5$ is —$SO_2$N($R_9$)—, —$SO_2$N($R_9$)—($C_1$-$C_4$) alkyl-, —N($R_9$)$SO_2$—($C_1$-$C_4$)alkyl-, —N($R_9$)$SO_2$—.

Preferred compounds of formula III-p include compounds of formula III-q, wherein $R_9$ is H, $C_1$-$C_6$ alkyl, or benzyl, wherein phenyl group is optionally substituted with 1, 2, 3, or 4 groups that are independently $C_1$-$C_4$ alkyl, $C_1$-$C_4$ alkoxy, halogen, OH, $NO_2$, $NH_2$, NH($C_1$-$C_6$)alkyl, N($C_1$-$C_6$)alkyl($C_1$-$C_6$)alkyl, $CF_3$, or $OCF_3$.

Preferred compounds of formula III-p include compounds of formula III-r, wherein $R_9$ is H, —$SO_2$phenyl, —$C_1$-$C_4$ alkyl-furanyl, —$C_1$-$C_4$ alkyl-tetrazolyl, —$C_1$-$C_4$- alkyl thienyl, —$C_1$-$C_4$- alkyl pyrrolyl, —$C_1$-$C_4$- alkyl pyridyl, wherein the aryl and heteroaryl groups are optionally substituted with 1, 2, 3, or 4 groups that are independently $C_1$-$C_4$ alkyl, $C_1$-$C_4$ alkoxy, halogen, OH, $NO_2$, $NH_2$, NH($C_1$-$C_6$)alkyl, N($C_1$-$C_6$)alkyl($C_1$-$C_6$) alkyl, $CF_3$, or $OCF_3$.

Preferred compounds of formula III-a include compounds of formula III-s, wherein $R_1$ and $R_{21}$ are both H; and $R_{22}$ is H, phenyl($C_1$-$C_6$)alkoxy, benzyl, halogen, ($C_1$-$C_6$) alkyl, OH, $C_1$-$C_6$ alkoxy, $NO_2$, $NH_2$, NH($C_1$-$C_6$)alkyl, or N($C_1$-$C_6$)alkyl($C_1$-$C_6$)alkyl, wherein the phenyl group is optionally substituted with 1, 2, 3, 4, or 5 groups that are independently $C_1$-$C_6$ alkyl, $C_1$-$C_6$ alkoxy, halogen, OH, $NO_2$, $CF_3$, or $OCF_3$.

Preferred compound of formula III-s include compounds of formula IV,

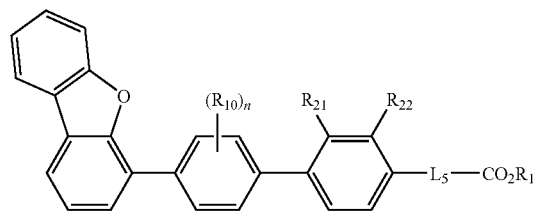

(IV)

wherein n is 0, 1, 2, 3, or 4; and each $R_{10}$ is independently, halogen, $C_1$-$C_6$ alkyl, $C_1$-$C_6$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl.

Preferred compound of formula III-s include compounds of formula V,

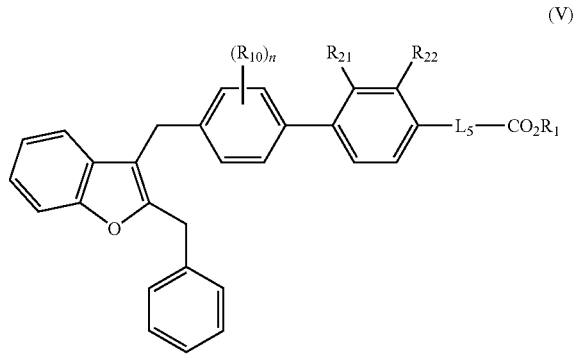

(V)

wherein
n is 0, 1, 2, 3, or 4; and
each $R_{10}$ is independently, halogen, $C_1$-$C_6$ alkyl, $C_1$-$C_6$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl.

Preferred compound of formula III-s include compounds of formula VI,

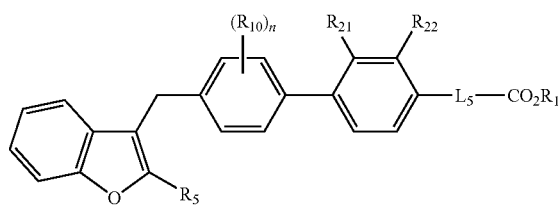

(VI)

wherein
n is 0, 1, 2, 3, or 4;
each $R_{10}$ is independently, halogen, $C_1$-$C_6$ alkyl, $C_1$-$C_6$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl; and
$R_5$ is alkoxycarbonyl, $C_1$-$C_6$ alkyl, $C_1$-$C_6$ alkoxy, halogen, $C_1$-$C_4$ haloalkyl, $C_1$-$C_4$ haloalkoxy, $NH_2$, $NH(C_1$-$C_6)$alkyl, $N(C_1$-$C_6)$alkyl$(C_1$-$C_6)$alkyl, or phenyl.

Preferred compound of formula III-s include compounds of formula VII,

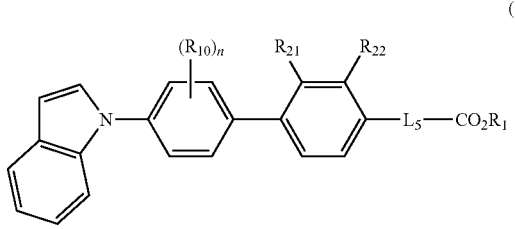

(VII)

wherein
n is 0, 1, 2, 3, or 4; and each $R_{10}$ is independently, halogen, $C_1$-$C_6$ alkyl, $C_1$-$C_6$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl.

Preferred compound of formula III-s include compounds of formula VIII,

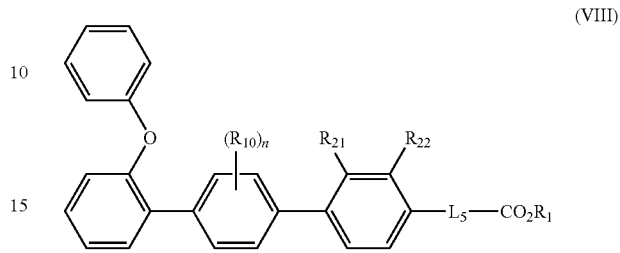

(VIII)

wherein
n is 0, 1, 2, 3, or 4; and
each $R_{10}$ is independently, halogen, $C_1$-$C_6$ alkyl, $C_1$-$C_6$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl.

A preferred class of compounds of formula A are compounds of formula X,

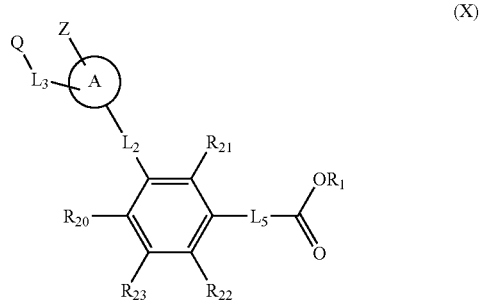

(X)

Preferred compounds of formula X are compounds of formula X-a, wherein,
Q is H, phenyl, -phenyl-O-phenyl, -phenyl-carbonyl-phenyl, -phenyl-$(C_1$-$C_4)$alkyl-phenyl, -phenyl-pyridyl, -phenyl-pyrimidyl, -phenyl-benzofuranyl, -phenyl-indolyl, -phenyl-piperidinyl, -phenyl-pyrrolidinyl, -phenyl-piperazinyl, indolizinyl, benzofuranyl, indolyl, dibenzofuranyl, -benzothienyl-$(C_1$-$C_4)$alkyl-phenyl, -indolyl-$(C_1$-$C_4)$alkyl-phenyl, benzofuranyl-$(C_1$-$C_4)$alkyl-phenyl, piperidinyl, pyrrolidinyl, tetrahydroisoquinolinyl, or imidazo[2,1-b]thiazol-3-one, wherein the aforementioned cyclic groups are optionally substituted with 1, 2, 3, 4, or 5 groups that are independently alkoxycarbonyl, $C_1$-$C_6$ alkyl, $C_1$-$C_6$ alkoxy, halogen, haloalkyl, haloalkoxy, $NR_6R_7$, phenyl, or phenyl-$(C_1$-$C_6)$alkyl-; wherein
$R_6$ and $R_7$ are independently H, $C_1$-$C_6$ alkyl, phenyl$(C_1$-$C_6)$alkyl, $C_2$-$C_6$ alkanoyl, phenyl$(C_2$-$C_6)$alkanoyl, $C_1$-$C_6$ alkoxycarbonyl, phenyl$(C_1$-$C_6)$alkoxycarbonyl, heteroarylcarbonyl, heteroaryl, heterocycloalkylcarbonyl, —C(O)NH$_2$, —C(O)NH$(C_1$-$C_6)$alkyl, —C(O)N$(C_1$-$C_6)$alkyl$(C_1$-$C_6)$alkyl, or —SO$_2$-aryl, wherein the cyclic groups are optionally substituted with 1, 2, 3, or 4 groups that are independently halogen, $C_1$-$C_4$ alkyl, $C_1$-$C_4$ alkoxy, $NO_2$, OH, $NH_2$, $NH(C_1$-$C_6)$alkyl, $N(C_1$-$C_6)$alkyl$(C_1$-$C_6)$alkyl, haloalkyl or haloalkoxy; and
Z is absent, H, or phenyl, wherein the phenyl group is optionally substituted with 1, 2, 3, 4, or 5 groups that are independently $C_1$-$C_6$ alkyl, $C_1$-$C_6$ alkoxy, halogen, $C_1$-$C_4$ haloalkyl, $C_1$-$C_4$ haloalkoxy, or $NO_2$.

A preferred class of compounds of formula X-a are compounds of formula X-b, wherein, the A ring is phenyl, -phenyl-O-phenyl, pyrido[1,2-a]indolyl, furanyl, thienyl, benzofuranyl, dibenzofuranyl, indolyl, thiazolyl, thiazolidinyl, each of which is optionally substituted with 1, 2, or 3 groups that are independently, halogen, $C_1$-$C_6$ alkyl, $C_1$-$C_6$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl; and $R_{20}$, $R_{21}$, $R_{22}$, and $R_{23}$ are independently selected from H, phenyl$(C_1$-$C_6)$alkoxy, phenyl$(C_1$-$C_6)$alkyl, halogen, $(C_1$-$C_6)$alkyl, OH, alkoxy, CN, $NO_2$, $NH_2$, $NH(C_1$-$C_6)$alkyl, $N(C_1$-$C_6)$alkyl$(C_1$-$C_6)$alkyl, NH-phenyl, NHC(O)—$(C_1$-$C_4)$ alkyl-phenyl, $N(C_1$-$C_4$ alkyl)C(O)—$(C_1$-$C_4)$ alkyl-phenyl, $N(C_1$-$C_4)$alkyl-phenyl, —$NHSO_2$-phenyl, —$N(C_1$-$C_4$alkyl)$SO_2$phenyl, wherein the phenyl group is optionally substituted with 1, 2, 3, 4, or 5 groups that are independently $C_1$-$C_6$ alkyl, $C_1$-$C_6$ alkoxy, halogen, OH, $NO_2$, $C_1$-$C_4$ haloalkyl, $C_1$-$C_4$ haloalkoxy.

A preferred class of compounds of formula X-b are compounds of formula X-c, wherein, $R_1$ is H, $C_1$-$C_6$ alkyl, benzyl, or allyl;

$L_2$ is a bond or —C(O)$NR_{10}$—, —$N(R_{10})$C(O)—, —$(C_1$-$C_4)$ alkyl-$N(R_{10})$C(O)—, —C(O)$N(R_{10})$—$(C_1$-$C_4)$alkyl-, —$N(R_{10})$C(O)—$(C_1$-$C_4)$alkyl-, —$(C_1$-$C_4)$alkyl-C(O)N$(R_{10})$—, —O—$(C_1$-$C_6)$alkyl-, or —$(C_1$-$C_6)$alkyl-O—;

$L_3$ is absent, a bond, —$(C_1$-$C_4)$alkyl-O—, —O—$(C_1$-$C_4)$ alkyl, —$(C_1$-$C_4)$ alkyl-, -alkenyl-, or -phenyl-;

$L_5$ is a bond, —O—$(C_1$-$C_6)$alkyl-, —$(C_1$-$C_6)$alkyl-O—, —C(O)$N(R_9)$—$(C_1$-$C_4)$ alkyl-, —$N(R_9)$C(O)—$(C_1$-$C_4)$ alkyl-, —$N(R_9)$—$(C_1$-$C_6)$alkyl-, -$(C_1$-$C_4)$ alkyl-$N(R_9)$-, —$(C_1$-$C_4)$ alkyl-$N(R_9)$—$(C_1$-$C_4)$ alkyl-, —$SO_2N(R_9)$—, —$SO_2N(R_9)$—$(C_1$-$C_4)$ alkyl-, —$N(R_9)SO_2$—$(C_1$-$C_4)$ alkyl-, —$N(R_9)SO_2$—, —$(C_1$-$C_4)$ alkyl-, —$N(R_9)$—$(C_1$-$C_6)$ alkyl- wherein -$(C_1$-$C_6)$ alkyl- is optionally substituted with phenyl, —$N(R_9)$C(O)—, —C(O)—$(C_1$-$C_4)$ alkyl-, —S—$(C_1$-$C_4)$ alkyl-, or —$(C_1$-$C_4)$ alkyl-S—$(C_1$-$C_4)$ alkyl-, wherein $R_9$ and $R_{10}$ are independently is H, $C_1$-$C_6$ alkyl, —$SO_2$phenyl, —$C_1$-$C_6$ alkyl-furanyl, —$C_1$-$C_6$ alkyl-tetrazolyl, —$C_1$-$C_6$-alkyl thienyl, —$C_1$-$C_6$- alkyl pyrrolyl, —$C_1$-$C_6$- alkyl pyridyl, benzyl, wherein the aryl and heteroaryl groups are optionally substituted with 1, 2, 3, or 4 groups that are independently $C_1$-$C_4$ alkyl, $C_1$-$C_4$ alkoxy, halogen, OH, $NO_2$, $NH_2$, $NH(C_1$-$C_6)$alkyl, $N(C_1$-$C_6)$alkyl$(C_1$-$C_6)$alkyl, $C_1$-$C_4$ haloalkyl, or $C_1$-$C_4$ haloalkoxy.

A preferred class of compounds of formula X-c are compounds of formula X-d, wherein, $L_2$ is a bond;

$L_3$ is a bond, —$(C_1$-$C_4)$alkyl-O—, —O—$(C_1$-$C_4)$alkyl, or —$(C_1$-$C_4)$ alkyl-;

the A ring is phenyl; and

Z is absent.

A preferred class of compounds of formulas X-c or X-d are compounds of formula X-e, wherein, $R_{21}$ and $R_{23}$ are both H;

$R_{22}$ is OH or phenyl$(C_1$-$C_6)$alkoxy;

$L_5$ is —$N(R_9)$C(O)—$(C_1$-$C_4)$alkyl-, or —$N(R_9)$C(O)—, and

Q is phenyl, benzofuranyl, indolyl, dibenzofuranyl, wherein the aforementioned cyclic groups are optionally substituted with 1, 2, 3, 4, or 5 groups that are independently alkoxycarbonyl, $C_1$-$C_6$ alkyl, $C_1$-$C_6$ alkoxy, halogen, haloalkyl, haloalkoxy, $NR_6R_7$, or phenyl.

A preferred class of compounds of formula X-e are compounds of formula I-f, wherein $R_9$ is H.

Preferred compounds of formula X-e are compounds of formula X-f, wherein Q is benzofuran, optionally substituted with $C_1$-$C_6$ alkyl.

In another aspect, the invention provides a method of treating diabetes comprising administering a pharmaceutically acceptable amount of a compound of formula A to a patient in need of such treatment.

In yet another aspect, the invention provides a pharmaceutical composition comprising a compound of formula A and at least one pharmaceutically acceptable solvent, carrier, adjuvant or excipient.

In another aspect, the invention provides a method of treating diabetes, comprising administering to a patient in need of such treatment a pharmaceutically acceptable amount of a compounds of formula A.

In another aspect, the invention encompasses a method of treating diabetes comprising administering to a patient in need thereof, a pharmaceutically acceptable amount of a compound or salt of formula A or a pharmaceutical composition comprising a compound or salt of formula A.

In another aspect, the invention encompasses a method of inhibiting TPT-1B comprising administering to a patient in need thereof, a pharmaceutically acceptable amount of a compound or salt of formula A or a pharmaceutical composition comprising a compound or salt of formula A.

In another aspect, the invention encompasses a method of treating cancer or neurodegenerative diseases comprising administering to a patient in need thereof, a pharmaceutically acceptable amount of a compound or salt of formula A or a pharmaceutical composition comprising a compound or salt of formula A.

In another aspect, the invention provides a method of treating syndrome X (consisting of such abnormalities as obesity, dyslipidemia, hypercoagulation, hypertension, insulin resistance and leading to heart disease and diabetes), obesity, diabetes, immunological disease, bleeding disorders and/or cancer comprising administering a pharmaceutically acceptable amount of a compound of formula A to a patient in need of such treatment.

As noted above, the compounds of the invention bind to and preferably, inhibit PTP-1B. As a result that are useful in the treatment of various diseases, including controlling or treating Type 2 diabetes, improving glucose tolerance, and in improving insulin sensitivity in patients in need thereof. The compounds are also useful in treating or controlling other PTP-1B mediated diseases, such as the treatment of cancer, neurodegenerative diseases and the like.

The term "alkoxy" represents an alkyl group of indicated number of carbon atoms attached to the parent molecular moiety through an oxygen bridge. Examples of alkoxy groups include, for example, methoxy, ethoxy, propoxy and isopropoxy.

As used herein, the term "alkyl" includes those alkyl groups of a designed number, of carbon atoms. Alkyl groups may be straight, or branched. Examples of "alkyl" include methyl, ethyl, propyl, isopropyl, butyl, iso-, sec- and tert-butyl, pentyl, hexyl, heptyl, 3-ethylbutyl, and the like.

The term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl, naphthyl, and anthracenyl. More preferred aryl groups are phenyl and naphthyl. Most preferred is phenyl.

The term "cycloalkyl" refers to a $C_3$-$C_8$ cyclic hydrocarbon. Examples of cycloalkyl include cyclopropyl, cyclobutyl, cyclopentyl, cyclohexyl, cycloheptyl and cyclooctyl.

The terms "halogen" or "halo" indicate fluorine, chlorine, bromine, and iodine.

The term "heterocycloalkyl" refers to a ring or ring system containing at least one heteroatom selected from nitrogen, oxygen, and sulfur, wherein said heteroatom is in a non-aromatic ring. The heterocycloalkyl ring is optionally fused to or otherwise attached to other heterocycloalkyl rings and/or non-aromatic hydrocarbon rings and/or phenyl rings. Preferred heterocycloalkyl groups have from 3 to 7 members. Examples of heterocycloalkyl groups include, for example, 1,2,3,4-tetrahydroisoquinolinyl, piperazinyl, morpholinyl, piperidinyl, tetrahydrofuranyl, pyrrolidinyl, pyridinonyl, and pyrazolidinyl. Preferred heterocycloalkyl groups include piperidinyl, piperazinyl, morpholinyl, pyrrolidinyl, pyridinonyl, dihydropyrrolidinyl, and pyrrolidinonyl.

The term "heteroaryl" refers to an aromatic ring system containing at least one heteroatom selected from nitrogen, oxygen, and sulfur. The heteroaryl ring may be fused or otherwise attached to one or more heteroaryl rings, aromatic or non-aromatic hydrocarbon rings or heterocycloalkyl rings. Examples of heteroaryl groups include, for example, pyridine, furan, thienyl, 5,6,7,8-tetrahydroisoquinoline and pyrimidine. Preferred examples of heteroaryl groups include thienyl, benzothienyl, pyridyl, quinolyl, pyrazolyl, pyrimidyl, imidazolyl, benzimidazolyl, furanyl, benzofuranyl, dibenzofuranyl, thiazolyl, benzothiazolyl, isoxazolyl, oxadiazolyl, isothiazolyl, benzisothiazolyl, triazolyl, pyrrolyl, indolyl, pyrazolyl, and benzopyrazolyl.

The compounds of this invention may contain one or more asymmetric carbon atoms, so that the compounds can exist in different stereoisomeric forms. These compounds can be, for example, racemates, chiral non-racemic or diastereomers. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound.

When the compounds described herein contain olefinic double bonds or other centers of geometric asymmetry, and unless otherwise specified, it is intended that the compounds include the cis, trans, Z- and E-configurations. Likewise, all tautomeric forms are also intended to be included.

The compounds of general Formula A may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of general Formula A and a pharmaceutically acceptable carrier. One or more compounds of general Formula A may be present in association with one or more non-toxic pharmaceutically acceptable carriers and/or diluents and/or adjuvants, and if desired other active ingredients. The pharmaceutical compositions containing compounds of general Formula A may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula A may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of general Formula A may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For disorders of the eye or other external tissues, e.g., mouth and skin, the formulations are preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w. For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may be preferable to apply a topical preparation of compounds of this invention to the affected area two to four times a day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water. Preferred non-human animals include domesticated animals.

As noted above, the invention also provides methods and compositions for combination therapy of Type I and Type II diabetes. In one such aspect, the invention provides methods of using compounds of formula A in combination with one or more angiotensin converting enzyme (ACE) inhibitors for improving the cardiovascular risk profile in patients experiencing or subject to Syndrome X or type II diabetes (non-insulin-dependent diabetes mellitus), preferably in human type II diabetics. These methods may also be characterized as the reduction of risk factors for heart disease, stroke or heart attack in a type II diabetic.

These methods include the reduction of hyperlipidemia in a patients experiencing or subject to Syndrome X or type II diabetes. These methods include methods lowering low density lipoprotein (LDL) blood levels and to increase high density lipoprotein (HDL) blood levels. The methods herein may further be characterized as useful for inhibiting, preventing or reducing atherosclerosis in a type II diabetics, or for reducing the risk factors thereof.

These methods also include the lowering of free fatty acid blood levels and triglyceride levels in type II diabetics.

Among the ACE inhibitors which may be utilized with the invention described herein are quinapril, ramipril, verapamil, captopril, diltiazem, clonidine, hydrochlorthiazide, benazepril, prazosin, fosinopril, lisinopril, atenolol, enalapril, perindropril, perindropril tert-butylamine, trandolapril and moexipril, or a pharmaceutically acceptable salt form of one or more of these compounds.

The invention also provides methods of using PTPase inhibitors of formula A for improving the cardiovascular or cerebrovascular risk profile in patients experiencing or subject to type II diabetes (non-insulin-dependent diabetes mellitus), preferably in human type II diabetics or a patient experiencing or subject to Syndrome X. These methods may also be characterized as the reduction of risk factors for heart disease, stroke or heart attack in a type II diabetic or a patient experiencing or subject to Syndrome X.

The invention also provides methods of using a pharmacological combination of one or more PTPase inhibiting agents, one or more biguanide agents, and, optionally one or more sulfonlylurea agents for treatment of type II diabetes or Syndrome X in a patient in need of such treatment. Also provided are methods of using these agents to treat or inhibit metabolic disorders mediated by insulin resistance or hyperglycemia in a patient in need thereof. Further included in this invention is a method of modulating blood glucose levels in a patient in need thereof.

Each of these methods comprises administering to a patient in need thereof pharmaceutically effective amounts of:
a) a PTPase inhibiting agent of formula I; and
b) a biguanide agent; and
c) optionally, a sulfonylurea agent.

Biguanide agents useful with this invention include metformin and its pharmaceutically acceptable salt forms. Sulfonylurea agents useful for the methods and combinations of this invention may be selected from the group of glyburide, glyburide, glipizide, glimepiride, chlorpropamide, tolbutamide, or tolazamide, or a pharmaceutically acceptable salt form of these agents.

This invention also provides pharmaceutical compositions and methods of using PTPase inhibitors of formula A in combination with one or more alpha-glucosidase inhibitors, such as miglitol or acarbose, for improving the cardiovascular risk profile in patients experiencing or subject to Syndrome X or type II diabetes (non-insulin-dependent diabetes mellitus), preferably in human type II diabetics. These methods may also be characterized as the reduction of risk factors for heart disease, stroke or heart attack in a patient in such need.

These methods include the reduction of hyperlipidemia in type II diabetics, including methods in type II diabetics for lowering low density lipoprotein (LDL) blood levels and to increase high density lipoprotein (HDL) blood levels. The methods herein may further be characterized as useful for inhibiting, preventing or reducing atherosclerosis in a type II diabetic or a patient experiencing or subject to Syndrome X, or the risk factors of either.

These methods also include the lowering free fatty acid blood levels and triglyceride levels in type II diabetics, or a patient experiencing or subject to Syndrome X.

Among the alpha-glucosidase inhibitors which may be utilized with the invention described herein are miglitol or acarbose, or a pharmaceutically acceptable salt form of one or more of these compounds.

This invention further provides methods for using a PTPase inhibitor of the invention and a sulfonylurea agent for the management of Syndrome X or type 2 diabetes and for improving the cardiovascular risk profile in patients experiencing or subject to those maladies. These methods may also be characterized as the reduction of risk factors in such patients for heart disease, stroke or heart attack in a type II diabetic. Such methods include the reduction of hyperlipidemia in a patients experiencing or subject to Syndrome X or type II diabetes and include methods for lowering low density lipoprotein (LDL) blood levels, high density lipoprotein (HDL) blood levels, and overall blood lipoprotein levels. The methods herein may further be characterized as inhibiting, preventing or reducing atherosclerosis in patients subject to or experiencing Syndrome X or type II diabetes, or the risk factors thereof. Such methods further include the lowering of free fatty acid blood levels and triglyceride levels in such patients.

Representative sulfonylurea agents include glipizide, glyburide (glibenclamide), chlorpropamide, tolbutamide, tolazamide and glimepriride, or the pharmaceutically acceptable salt forms thereof.

In addition, the invention provides combinations of a PTPase inhibitor of the invention and at least one thiazolidinedione agents. Such combinations are useful for treatment, inhibition or maintenance of Syndrome X or type II diabetes in patients in need of such treatment. Accordingly, methods of using such combinations are provided by the invention. Thus, the invention provides methods of using these agents to treat or inhibit metabolic disorders mediated by insulin resistance or hyperglycemia in patients in need thereof. Further included in this invention are methods of modulating blood glucose levels in a patient in need thereof.

Each of these methods comprises administering to a patient in need thereof pharmaceutically effective amounts of:

a) a thiazolidinedione agent, such as selected from the group of pioglitzone and rosiglitazone, or a pharmaceutically acceptable salt form of these agents; and b) a compound of formula A.

The invention also provides pharmaceutical compositions and methods of using PTPase inhibitors in combination with one or more antilipemic agents. Such methods and compositions are useful for improving the cardiovascular risk profile in patients experiencing or subject to type II diabetes (non-insulin-dependent diabetes mellitus), preferably in type II diabetics or Syndrome X. These methods also include reducing the risk factors for heart disease, stroke or heart attack in a type II diabetic or a patient experiencing or subject to Syndrome X. Such methods further include the reduction of hyperlipidemia in type II diabetics, including such methods in type II diabetics for lowering low density lipoprotein (LDL) blood levels and to increase high density lipoprotein (HDL) blood levels. These compositions and methods are also useful for inhibiting, preventing or reducing atherosclerosis in a type II diabetic or a patient experiencing or subject to Syndrome X, or the risk factors thereof. In this aspect, the compositions and methods are useful for lowering of free fatty acid blood levels and triglyceride levels in type II diabetics, or patients experiencing or subject to Syndrome X.

Representative antilipemic or agents, also known as antihyperlipidemic agents, suitable for use in the invention are bile acid sequestrants, fibric acid derivatives, HMG-CoA reductase inhibitors and nicotinic acid compounds. Bile acid sequestrant agents useful with this invention include colestipol and colesevelam, and their pharmaceutically acceptable salt forms. Fibric acid derivatives which may be used with the present invention include clifofibrate, gemfibrozil and fenofibrate. HMG-CoA reductase inhibitors, also known as statins, useful with this invention include cerivastatin, fluvastatin, atorvastatin, lovastatin, pravastatin and simvastatin, or the pharmaceutically acceptable salt forms thereof. Niacin is an example of a nicotinic acid compound which may be used with the methods of this invention. Also useful are lipase inhibiting agents, such as orlistat.

This invention also provides pharmaceutical compositions that are a combination of a compound of Formula A and an aldose reductase inhibitor (ARI). Such combinations are useful in methods for treating, inhibiting or preventing type II diabetes, or its related and associated symptoms, disorders and maladies. These methods comprise administering to a patient in need of such therapy a pharmaceutically effective amount of a composition comprising a combination of pharmaceutically effective amounts of a compound of formula A and an ARI. These compositions and methods are useful for the treatment, prevention or inhibition of diabetic neuropathy, diabetic nephropathy, retinopathy, keratopathy, diabetic uveitis, cataracts.

Representative suitable ARIs are disclosed in U.S. Pat. Nos. 6,420,426 and 6,214,991.

Combinations of the compounds of Formula A and an ARI are also useful for inhibition or reduction of risk factors for heart disease, stroke or heart attack in a type II diabetic. Therefore, in this aspect the invention is useful for reducing hyperlipidemia and/or low density lipoprotein (LDL) blood levels in type II diabetics. Also included in this aspect are methods for inhibiting, preventing or reducing atherosclerosis or the risk factors thereof in type II diabetics. This aspect includes lowering of free fatty acid blood levels and triglyceride levels.

This invention also provides methods of using a compound of formula A and insulin(s) for the management of type I or type II diabetes. Accordingly, the invention provides for combination therapy, i.e., where a compound of Formula A is administered in combination with insulin. Such combination therapy encompasses simultaneous or sequential administration of the compound of Formula A and insulin. The insulins useful in this aspect include both naturally occurring and synthetic insulins.

Insulins useful with the methods and combinations of this invention include rapid acting insulins, intermediate acting insulins, long acting insulins and combinations of intermediate and rapid acting insulins.

Rapid acting commercially available insulin products include HUMALOG® Brand Lispro Injection (rDNA origin); HUMULIN® Regular Human Injection, USP [rDNA origin]; HUMULIN® Regular U-500 Concentrated Human Injection, USP [rDNA origin]; REGULAR ILETIN® II (insulin injection, USP, purified pork) available from Eli Lilly and Co.; and the NOVALIN® Human Insulin Injection and VENOSULIN® BR Buffered Regular Human Injection, each available from Novo Nordisk Pharmaceuticals.

Commercially available intermediate acting insulins useful with this invention include, but are not limited to, the HUMULIN® L brand LENTE® human insulin [rDNA origin] zinc suspension, HUMULIN® N NPH human insulin [rDNA origin] isophane suspension, LENTE® ILETIN.RTM. II insulin zinc suspension, USP, purified pork, and NPH ILETIN® II isophane insulin suspension, USP, purified pork, available from Eli Lilly and Company, LANTUS® insulin glargine [rDNA origin] injection, available from Aventis Pharmaceuticals, and the NOVOLIN L Lente® human insulin zinc suspension (recombinant DNA origin), and NOVOLIN® N NPH human insulin isophane suspension (recombinant DNA origin) products available from Novo Nordisk Pharmaceuticals, Inc, Princeton N.J.

Also useful with the methods and formulations of this invention are intermediate and rapid acting insulin combinations, such as the HUMALOG® Mix 75/25 (75% Insulin Lispro Protamine Suspension and 25% Insulin Lispro Injection), HUMULIN® 50/50 (50% Human Insulin Isophane Suspension and 50% Human Insulin Injection) and HUMULIN® 70/30 (70% Human Insulin Isophane Suspension and 30% Human Insulin Injection), each available from Eli Lilly and Company. Also useful are the NOVALIN® 70/30 (70% NPH, Human Insulin Isophane Suspension and 30% Regular, Human Insulin Injection) line of combination products available from Novo Nordisk Pharmaceuticals.

A commercially available long acting insulin for use with this invention is the HUMULIN® U Ultralente® human insulin [rDNA origin] extended zinc suspension, available from Eli Lilly and Company.

Also useful in the methods of this invention are inhaled insulin products, such as the EXUBERA® inhaled insulin product developed by Pfizer Inc. and Aventis SA.

Each of these insulin products can be administered as directed by a medical professional using administrations, dosages and regimens known in the art, such as those published for each product in the Physicians' Desk Reference, 55 Edition, 2001, published by Medical Economics Company, Inc. at Montvale, N.J., the relevant sections of which are incorporated herein by reference. In this aspect, the invention includes, for example, methods for improving the cardiovascular and cerebrovascular risk profiles in patients experiencing or subject to type I or type II diabetes (non-insulin-dependent diabetes mellitus), preferably in human type II diabetics. These methods may also be characterized as the inhibition or reduction of risk factors for heart disease, stroke or heart attack in a type II diabetic.

The compounds of the present invention may be prepared by use of known chemical reactions and procedures. Representative methods for synthesizing compounds of the invention are presented below. It is understood that the nature of the substituents required for the desired target compound often determines the preferred method of synthesis. All variable groups of these methods are as described in the generic description if they are not specifically defined below.

Methods of Preparation

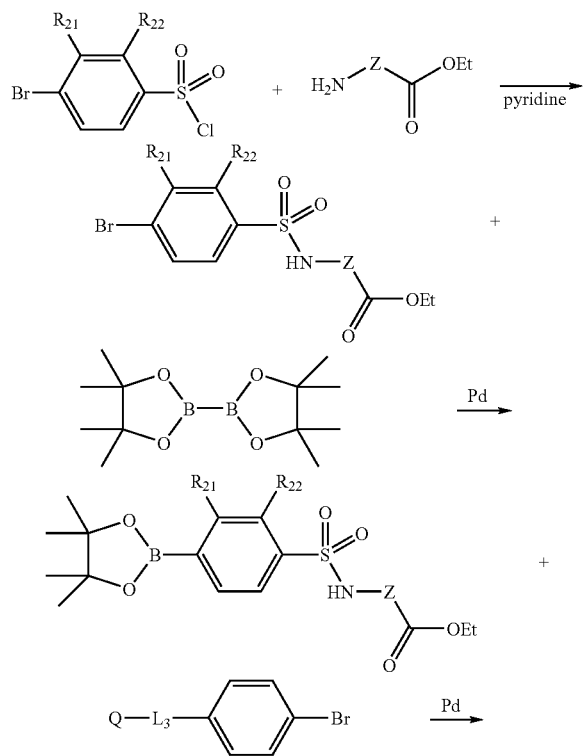

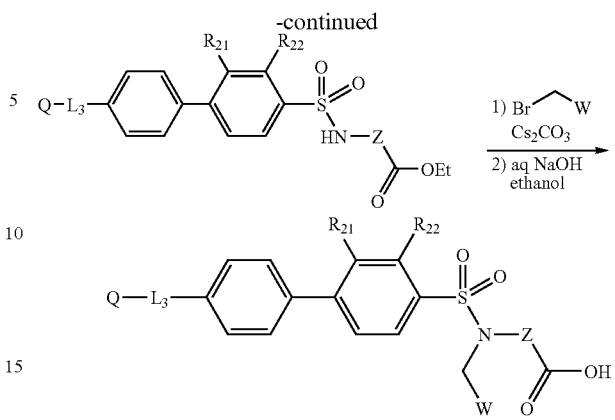

A method for preparing compounds of the invention is illustrated in scheme 1. Certain compounds of the invention are prepared from a substituted 4-bromobenzenesulfonylchloride or 4-bromobenzeneacid chloride as illustrated in scheme 1.

Treatment with the desired amino acid ester in the presence of a base, such as pyridine or triethylamine, gives the corresponding sulfonamide or amide. Activation of the aryl bromide by treatment with bis(pinacolato)diboron and a palladium catalyst give the boronic ester, which is subsequently coupled to a variety of aryl or heteroaryl bromides or iodides using a palladium catalyst. For some examples, the desired aryl or heteroaryl bromide may need to be prepared separately. In general the preparation of these intermediates can be accomplished using methods known in the art.

Once the $L_3$-Q group is in place, the sulfonamide or amine nitrogen can be alkylated with the desired side chain alkyl halide. This is usually done with a base, such as cesium carbonate, or sodium hydride. Finally, the ester intermediate is hydrolyzed to give the target compound.

Those having skill in the art will recognize that the starting materials and reaction conditions may be varied, the sequence of the reactions altered, and additional steps employed to produce compounds encompassed by the present invention, as demonstrated by the following examples. In some cases, protection of certain reactive functionalities may be necessary to achieve some of the above transformations. In general, the need for such protecting groups as well as the conditions necessary to attach and remove such groups will be apparent to those skilled in the art of organic synthesis.

The disclosures of all articles and references mentioned in this application, including patents, are incorporated herein by reference in their entirety.

Structures were named using Name Pro IUPAC Naming Software, version 5.09, available from Advanced Chemical Development, Inc., 90 Adelaide Street West, Toronto, Ontario, M5H 3V9, Canada or with ChemDraw v. 6.02, which is available from Cambridgesoft.com in Cambridge, Mass.

CHEMISTRY EXAMPLES

The preparation of intermediates and compounds of the invention is illustrated further by the following examples, which are not to be construed as limiting the invention in scope or spirit to the specific procedures and compounds described in them. In all cases, unless otherwise specified, the column chromatography is performed using a silica gel solid phase.

Example 1

Preparation of 4-Dibenzofuran-4-yl-phenyl-boronic acid

Step 1: (4-Dibenzofuran-4-yl-phenyl)-trimethyl-silane

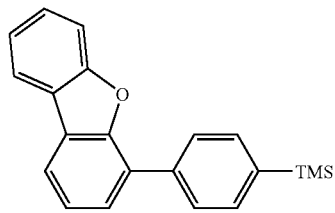

A solution of dibenzofuran-4-yl-boronic acid (20.0 g, 94.3 mmol), (4-bromo-phenyl)-trimethyl-silane (21.62 g, 94.3 mmol), $K_2CO_3$ (39.1 g, 3 equiv., 283 mmol) in toluene (100 mL), ethanol (60 mL) and water (30 mL) was purged with nitrogen for 5 min (bubbled into solution) and treated with $Pd(PPh_3)_4$ (3.59 g, 2.9 mmol). After heating to 80° C. for 4 h, the solution was cooled to room temperature, poured into water (300 mL) and extracted with ethyl acetate (300 mL). The organic phase was washed with sat'd aq NaCl, dried over anhydrous $MgSO_4$, filtered and concentrated in vacuo. Purification by flash column chromatography (5-20% ethyl acetate in heptane) afforded (4-dibenzofuran-4-yl-phenyl)-trimethyl-silane as a colorless oil (28.9 g, 96%).

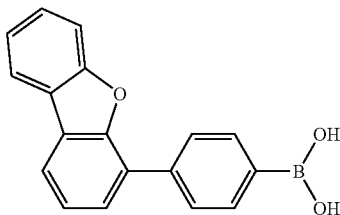

Step 2: 4-Dibenzofuran-4-yl-phenyl-boronic acid

A solution of (4-dibenzofuran-4-yl-phenyl)-trimethyl-silane (28 6 g, 90.2 mmol) in dichloromethane (350 mL, 0.26 M) was cooled to −78° C. and carefully treated with borontribromide (135 mL, 1.5 equiv., 135 mmol). After the addition was complete, the solution was warmed to room temperature and stirred for 3 h. Next, the reaction mixture was re-cooled to −78° C., treated with dry methanol (30 mL), slowly warmed to room temperature and stirred for 1.5 h. Next, the solution was re-cooled to −78° C., carefully quenched with 10% aq HCl (50 mL), warmed to room temperature and stirred for 1 h (solids form). The resulting solution was poured into water (500 mL) and extracted with ethyl acetate (3×700 mL). The combined organic layers were washed with sat'd aq NaCl, dried over anhydrous $MgSO_4$, filtered and concentrated in vacuo. The crude product was suspended in a 10% ethyl acetate in heptane solution, filtered and washed with the same solution (5×60 mL) to give 4-dibenzofuran-4-yl-phenyl-boronic acid as a white solid (20.2 g, 77%).

Example 2

5-Benzyl-5-{2-[4'-(2-benzylbenzofuran-3-yl)-biphen-4-yl]-2-oxoethyl}-2,2-dimethyl-[1,3]-dioxane-4,6-dione

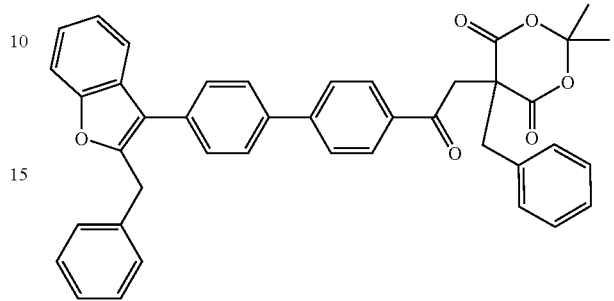

A solution of 5-{2-[4'-(2-benzylbenzofuran-3-yl)-biphen-4-yl]-2-oxoethyl}-2,2-dimethyl-[1,3]dioxane-4,6-dione (200 mg, 0.37 mmol) in THF/DMF (5:1; 6 mL) was added dropwise to a stirred suspension of sodium hydride (95%, 10.2 mg, 0.40 mmol) in anhydrous THF (5 mL) at room temperature. The clear solution was stirred at room temperature for 30 mins and then a solution of benzyl bromide (76 mg, 0.44 mmol) in THF (5 mL) was added dropwise, followed by the addition of tetra-n-butylammonium iodide (5 mg) as a solid. The reaction mixture was warmed to 60° C. for 4 hrs (TLC control), cooled to room temperature and then water (10 mL) was added cautiously. The reaction mixture was extracted with diethyl ether (3×15 mL). The combined extract was washed with water (2×10 mL), brine (3×10 mL), dried over anhydrous $MgSO_4$, filtered and concentrated in vacuo. Purification of the product by trituration and filtration from MeOH afforded the title compound as a pale yellow solid (210 mg). 1H-NMR ($CDCl_3$, 300 MHz): δ 8.12 (2H, d, J=8 Hz, Ar-H), 7.88 (4H, d, J=6 Hz, Ar-H), 7.53-7.69 (4H, m, Ar-H), 7.26 (1H, m, Ar-H), 7.14 (11H, m, Ar-H), 4.26 (2H, s, $PhCH_2$), 4.16 (2H, $CH_2CO$), 3.38 (2H, s, $PhCH_2$), 1.98 (3H, s, Me), 0.78 (3H, s, Me).

Example 3

1-(4-Bromophenyl)-1H-indole

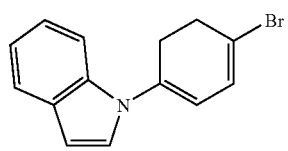

A solution of 1H-indole (3.0 g, 25.6 mmol), 4-fluorobromobenzene (4.48 g, 25.6 mmol), potassium fluoride (40% wt on alumina; 3.0 g) and 18-crown-6 (690 mg, 2.56 mmol) in anhydrous DMSO (30 mL) was heated at 150° C. for 24 hours, and then cooled to room temperature. The reaction mixture was poured into water (50 mL) and extracted with diethyl ether (3×50 mL). The combined organic extract was washed with water (2×30 mL), brine (3×30 mL), dried over anhydrous $MgSO_4$, filtered and concentrated in vacuo. Purification of the product by flash column chromatography, using 20% ethyl acetate/hexane as eluent, afforded the title compound has a pale yellow solid (5.5 g, 76%).

Example 4

4'-Indol-1-yl-biphenyl-4-carbaldehyde

To a stirred solution of the bromide (from example 3) (7.77 g, 28.6 mmol) and tetrakis-(triphenylphosphine)palladium (0) (1.8 g, 1.45 mmol) in toluene (100 mL) was added a solution of 4-formylphenylboronic acid (5.21 g, 34.5 mmol) in ethanol (20 mL) and 2N sodium carbonate (28.6 mL, 57.2 mmol). The resulting suspension was stirred at 90° C. for 4 hrs (TLC control). The reaction was cooled, diluted with water (50 mL) and extracted with diethyl ether (3×100 mL). The combined extract was washed with water, brine, dried over anhydrous $MgSO_4$, filtered and concentrated in vacuo. The resulting brown solid was redissolved in tetrahydrofuran (50 mL). 2N Hydrochloric acid (10 mL) was added and the resulting solution was stirred at room temperature for 1 hour, and then diluted with water (50 mL) and extracted with diethyl ether (3×100 mL). The combined extract was washed with water, brine, dried over anhydrous $MgSO_4$, filtered and concentrated in vacuo. Purification of the product by flash column chromatography, using 20% ethyl acetate in heptane as eluent, afforded the title compound as a white solid (8.02 g, 94%), 1H NMR ($CDCl_3$, 300 MHz) δ 10.1 (1H, s, CHO), 8.01 (2H, d, J=8 Hz, Ar-H), 7.70 (5H, m, Ar-H), 7.62 (2H, d, J=8 Hz, Ar-H), 7.39 (1H, d, J=3.5 Hz, Ar-H), 7.22 (3H, m, Ar-H), 6.74 (1H, d, J=3.5 Hz, Ar-H).

Example 5

(4'-Indol-1-yl-biphen-4-yl)methanol

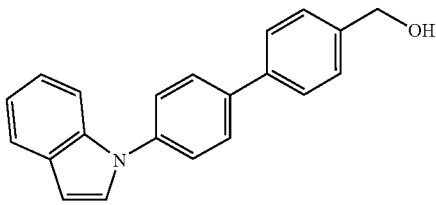

Sodium borohydride (783 mg, 20.6 mmol) was added portion-wise to a stirred solution of aldehyde (prepared in example 4) (3.06 g, 10.3 mmol) in a mixture of anhydrous THF and ethanol (1:1; 100 mL) at room temperature. The reaction mixture was stirred for 10 minutes at room temperature (TLC control), poured into water (50 mL) and acidified to pH 4 with 2N hydrochloric acid, and then extracted with diethyl ether (3×20 mL). The combined extract was washed with 0.5 N hydrochloric acid (2×10 mL), water and finally brine. The ethereal solution was dried over anhydrous $MgSO_4$, filtered and concentrated in vacuo. Purification of the product by flash column chromatography, using 30% ethyl acetate/hexane as eluent, afforded the title compound has a white solid (2.80 g, 91%); 1H NMR ($CDCl_3$, 300 MHz) δ 7.55-7.78 (7H, m, Ar-H), 7.52 (2H, d, J=8 Hz, Ar-H), 7.41 (1H, d, J=3.5 Hz, Ar-H), 7.22 (3H, m, Ar-H), 6.72 (1H, d, J=3.5 Hz, Ar-H), 4.79 (2H, d, J=5.5 Hz, $CH_2O$).

Example 6

Methanesulfonic acid, (4'-Indol-1-yl-biphen-4-yl)methyl ester

Methanesulfonyl chloride (194 mg, 131 μL, 1.7 mmol) was added dropwise to a cooled (0° C.) solution of alcohol (prepared in example 5) (620 mg, 1.54 mmol) and triethylamine (311 mg, 0.43 mL, 3.08 mmol) in anhydrous methylene chloride (10 mL). The clear reaction mixture was stirred at 0° C. for 2-4 hrs (TLC control), then poured into water (50 mL), and extracted with diethyl ether (3×30 mL). The combined extract was washed with 0.5 N hydrochloric acid (2×10 mL), water and finally brine. The ethereal solution was dried over anhydrous $MgSO_4$, filtered and concentrated in vacuo. The crude mesylate was used in the subsequent alkylation step without further purification.

Example 7

4'-Dibenzofuran-4-yl-biphenyl-4-carbaldehyde

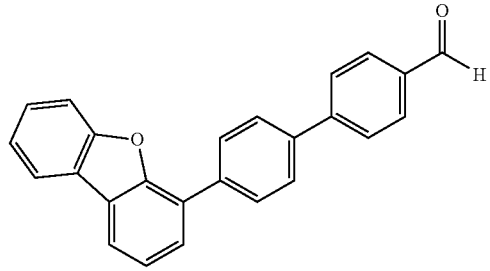

A solution of dibenzofuran-4-boronic acid (1.0 g, 4.7 mmol) in ethanol (10 mL) was added to a stirred solution of 1-bromo-4-iodobenzene (1.33 g, 4.7 mmol) and tetrakis-(triphenylphosphine)palladium(0) (271 mg, 5 mol %) in toluene (40 mL). 2N sodium carbonate (4.7 mL, 9.4 mmol) was added and the reaction was heated to 90° C. (oil bath temp.) for 2-3 hrs until complete (TLC control).

The reaction mixture was cooled to room temperature and partitioned between water and diethyl ether. The phases were separated, the aqueous phase being further extracted with diethyl ether (2×20 mL). The combined extract was washed with water and brine. The ethereal solution was dried over anhydrous $MgSO_4$, filtered and concentrated in vacuo to yield 4-(4-bromophenyl)-dibenzofuran as a yellow solid, which was used immediately without further purification.

A solution of 4-formylphenylboronic acid (0.9 g, 5.64 mmol) in ethanol (10 mL) was added to a stirred solution of the crude 4-(4-bromophenyl)-dibenzofuran (from the previous reaction) in toluene (40 mL). tetrakis-(Triphenylphosphine)palladium(0) (270 mg, 5 mol %) and 2N sodium carbonate (4.7 mL, 9.4 mmol) were added and the reaction was heated to 100° C. (oil bath temp.) for 2-3 hrs until complete (TLC control). The reaction mixture was cooled to room temperature and partitioned between water and ethyl acetate. The phases were separated, the aqueous phase being further extracted with ethyl acetate (2×20 mL). The combined extract was washed with 0.5 N hydrochloric acid, water and brine and then dried over anhydrous $MgSO_4$, filtered and concentrated

Example 8

(4'-Dibenzofuran-4-yl-bipenyl-4-yl)methanol

Sodium borohydride (322 mg, 8.4 mmol) was added portion-wise to a stirred solution of aldehyde (prepared in example 7) (1.48 g, 4.2 mmol) in a mixture of anhydrous THF and ethanol (1:2; 50 mL) at room temperature. The reaction mixture was stirred for 5-10 minutes at room temperature (TLC control), poured into water (50 mL) and acidified to pH 4 with 2N hydrochloric acid, and then extracted with diethyl ether (3×30 mL). The combined extract was washed with 0.5 N hydrochloric acid (2×10 mL), water and finally brine. The ethereal solution was dried over anhydrous MgSO$_4$, filtered and concentrated in vacuo. Purification of the product by flash column chromatography, using 30% ethyl acetate/hexane as eluent, afforded the title compound has a white solid (1.40 g).

Example 9

Methanesulfonic acid, 4'-dibenzofuran-4-yl-biphenyl-4-y-lmethyl ester

Methanesulfonyl chloride (490 mg, 330 µL, 4.3 mmol) was added dropwise to a cooled (0° C.) solution of alcohol (prepared in example 8) (1.38 g, 3.9 mmol) and triethylamine (800 mg, 1.1 mL, 7.9 mmol) in anhydrous methylene chloride (50 mL). The clear reaction mixture was stirred at 0° C. for 2-4 hrs (TLC control), then poured into water (50 mL), and extracted with diethyl ether (3×30 mL). The combined extract was washed with 0.5 N hydrochloric acid (2×10 mL), water and finally brine. The ethereal solution was dried over anhydrous MgSO$_4$, filtered and concentrated in vacuo. The crude mesylate was used in the subsequent alkylation step without further purification.

Example 10

Trifluoro-methanesulfonic acid 4-(2-benzyl-benzofuran-3-yl)-phenyl ester

To a stirred solution of the known phenol, 4-(2-benzylbenzofuran-3-yl)-phenol, (7.2 g, 24 mmol) in anhydrous methylene chloride (100 mL), was added triethylamine (4.86 g, 6.7 mL, 48 mmol) and then N-phenyltrifluoromethanesulfonimide (9.4 g, 26.4 mmol) portionwise as a solid. The resulting solution was stirred for 2 hours at room temperature and then diluted with water, extracted with diethyl ether (3×100 mL). The combined extract was washed with water, brine, dried over anhydrous MgSO$_4$, filtered and concentrated in vacuo. Purification of the product by flash column chromatography, using 10% ethyl acetate in heptane as eluent, afforded the title compound as a white solid (9.35 g, 90%).

Example 11

4'-(2-Benzylbenzofuran-3-yl)biphenyl-4-carbaldehyde

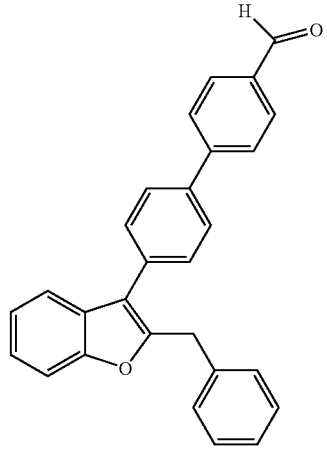

To a stirred solution of the triflate (from example 10) (9.35 g, 21.6 mmol) and tetrakis-(triphenylphosphine)palladium (0) (750 mg, 0.65 mmol) in toluene (70 mL) was added a solution of 4-formylphenylboronic acid (4.06 g, 27.05 mmol) in ethanol (20 mL) and 2N sodium carbonate (21.6 mL, 43.2 mmol). The resulting suspension was stirred at 100° C. for 4 hrs (TLC control). The reaction was cooled, diluted with water (50 mL) and extracted with diethyl ether (3×100 mL). The combined extract was washed with water, brine, dried over anhydrous MgSO$_4$, filtered and concentrated in vacuo.

The resulting brown solid was redissolved in tetrahydrofuran (50 mL). 2N Hydrochloric acid (10 mL) was added and the resulting solution was stirred at room temperature for 1 hour, and then diluted with water (50 mL) and extracted with diethyl ether (3×100 mL). The combined extract was washed with water, brine, dried over anhydrous MgSO$_4$, filtered and concentrated in vacuo. Purification of the product by flash column chromatography, using 20% ethyl acetate in heptane as eluent, afforded the title compound as a white solid (7.34 g, 88%).

Example 12

4'-(2-Benzylbenzofuran-3-yl)biphenyl-4-methanol

To a solution of 4'-(2-benzylbenzofuran-3-yl)biphenyl-4-carbaldehyde (5.0 g, 12.9 mmol) in ethanol (100 mL) and tetrahydrofuran (25 mL) was added sodium borohydride (980 mg, 25.8 mmol) as a solid in 3 portions. The reaction was stirred at room temperature for 1 hour (TLC control) and then poured into water (100 mL) and extracted with diethyl ether (3×100 mL). The combined extract was washed with water, brine, dried over anhydrous MgSO$_4$, filtered and concentrated in vacuo to afford the title compound as a white solid (5.02 g, 99%).

Example 13

2-Benzyl-3-(4'-bromomethylbiphen-4-yl)benzofuran

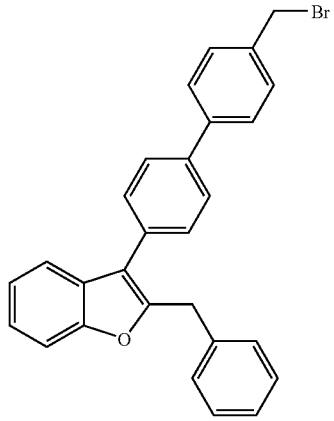

To a solution of 4'-(2-benzylbenzofuran-3-yl)biphenyl-4-methanol (5.01 g, 12.7 mmol) in anhydrous acetonitrile (75 mL) was added dibromtriphenylphosphorane (5.45 g, 12.7 mmol) as a solid portionwise over 15 mins. The reaction was stirred for 2 hours (TLC control) and then poured into water (100 mL) and extracted with diethyl ether (3×100 mL). The combined extract was washed with water, brine, dried over anhydrous MgSO$_4$, filtered and concentrated in vacuo to afford the title compound as an off-white solid (4.98 g, 87%): 1H NMR (CDCl$_3$, 300 MHz): δ 7.70 (2H, m, Ar-H), 7.63 (4H, m, Ar-H), 7.50 (3H, m, Ar-H), 7.30 (4H, m, Ar-H), 7.25 (4H, m, Ar-H), 4.57 (2H, s, CH$_2$Br), 4.26 (2H, PhCH$_2$).

Example 14

4'-Bromo-biphenyl-4-carboxylic acid methyl ester

A mixture of methyl 4-iodobenzoate, 9.38 g (35.8 mmol), 4-bromophenylboronic acid 7.18 g (35.8 mmol), Pd(PPh$_3$)$_4$, 2.07 g (1.79 mmol), in 180 mL of toluene and 100 mL of ethanol was heated to obtain a clear solution. To the solution was added 30 mL of 4.0M aq. Na$_2$CO$_3$. The reaction mixture refluxed for 4 h at 80° C. The mixture was cooled to room temperature and diluted with 300 mL ethyl acetate. The organic layer was washed with 2×300 mL portions of water, 2×300 mL portions of sat. aq. NaCl, and dried (MgSO$_4$). After the solution was concentrated, the residue was purified by column chromatography (eluted with 7% EtOAc-Heptane) to afford the desired product in 7.8 g (78%) as a white solid. $^1$H NMR (CDCl$_3$) 8.10 (d, 2H, J=9.0 Hz), 7.62 (d, 2H, J=9.0 Hz), 7.59 (d, 2H, J=9.3 Hz), 7.48 (d, 2H, J=9.3 Hz), 3.95 (s, 3H).

Example 15

(4'-Bromo-biphenyl-4-yl)-methanol

A solution of 4'-Bromo-biphenyl-4-carboxylic acid methyl ester, 7.8 g (27.9 mmol) in 150 mL of tetrahydrofuran was cooled to 0° C. via ice-water bath. Lithiumaluminum-hydride, 1.1 g (27.9 mmol) was added to the solution in one portion. The reaction mixture stirred at 0° C. for 1 h. The mixture was slowly quenched with 10 mL of isopropyl alcohol, then with 10 mL of water. The aqueous mixture was extracted with 3×50 mL portions of ethyl acetate. The organic layers were combined, washed with sat. aq. NaCl, and dried (MgSO$_4$). The solution was concentrated to afford the desired product in 7.01 g (100%) as a white solid. The material was taken to the next step without further purification.

Example 16

4'-Bromo-4-bromomethyl-biphenyl

A solution of (4'-bromo-biphenyl-4-yl)-methanol, 7.01 g (27.9 mmol) and dibromo-triphenylphosphorane 11.8 g (27.9 mmol) in 150 mL of methylene chloride stirred at room temperature for 2 h. The solution was diluted with 100 mL of water and extracted with 2×200 mL portions of diethyl ether. The organic layers were combined, washed with sat. aq. NaCl, and dried (MgSO$_4$). After the solution was concentrated, the residue was purified through a short plug of silica gel (eluted with 50% EtOAc-Heptane) to afford the desired product in 9.1 g (100%) as a white solid. The material was taken to the next step without further purification.

Example 17

(4-Dibenzofuran-4-yl-phenyl)boronic acid

Step 1: (4-Dibenzofuran-4-yl-phenyl)-trimethyl-silane

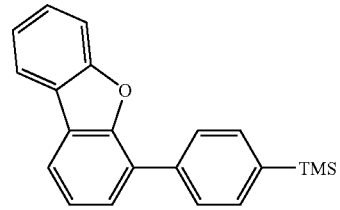

A solution of dibenzofuran-4-yl-boronic acid (20.0 g, 94.3 mmol), (4-bromo-phenyl)-trimethyl-silane (21.62 g, 94.3 mmol), K$_2$CO$_3$ (39.1 g, 3 equiv., 283 mmol) in toluene (100 mL), ethanol (60 mL) and water (30 mL) was purgged with nitrogen for 5 min (bubbled into solution) and treated with Pd(PPh$_3$)$_4$ (3.59 g, 2.9 mmol). After heating to 80° C. for 4 h, the solution was cooled to room temperature, poured into water (300 mL) and extracted with ethyl acetate (300 mL). The organic phase was washed with sat'd aq NaCl, dried over anhydrous MgSO$_4$, filtered and concentrated in vacuo. Purification by flash column chromatography (5-20% ethyl acetate in heptane) afforded (4-dibenzofuran-4-yl-phenyl)-trimethyl-silane as a colorless oil (28.9 g, 96%).

Step 2: 4-Dibenzofuran-4-yl-phenyl-boronic acid

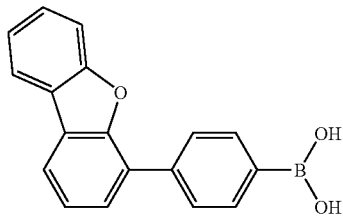

A solution of (4-dibenzofuran-4-yl-phenyl)-trimethyl-silane (28 6 g, 90.2 mmol) in dichloromethane (350 mL, 0.26 M) was cooled to −78° C. and carefully treated with borontribromide (135 mL, 1.5 equiv., 135 mmol). After the addition was complete, the solution was warmed to room temperature and stirred for 3 h. Next, the reaction mixture was re-cooled to −78° C., treated with dry methanol (30 mL), slowly warmed to room temperature and stirred for 1.5 h. Next, the solution was re-cooled to −78° C., carefully quenched with 10% aq HCl (50 mL), warmed to room temperature and stirred for 1 h (solids form). The resulting solution was poured into water (500 mL) and extracted with ethyl acetate (3×700 mL). The combined organic layers were washed with sat'd aq NaCl, dried over anhydrous MgSO$_4$, filtered and concentrated in vacuo. The crude product was suspended in a 10% ethyl acetate in heptane solution, filtered and washed with the same solution (5×60 mL) to give 4-dibenzofuran-4-yl-phenyl-boronic acid as a white solid (20.2 g, 77%).

Example 18

Preparation of [[4'-(2-Benzyl-benzofuran-3-yl)-biphenyl-4-sulfonyl]-(3-trifluoromethyl-benzyl)-amino]-acetic acid Step 1: Preparation of Tert-Butyl-[(4-bromobenzenesulfonyl)-(3-trifluoromethylbenzyl)amino]acetate.

3-Trifluoromethylbenzyl bromide (313 mg, 1.31 mmol) was added dropwise to a stirred suspension of tert-butyl-(4-bromobenzesulfonylamino)acetate (404 mg, 1.16 mmol) and cesium carbonate (768 mg, 2.36 mmol) in anhyd DMF (5 mL). The resultant reaction mixture was stirred at room temperature for 24 h, diluted with ethyl acetate (20 mL), washed with sat'd aq LiCl (3×10 mL), sat'd aq NaCl, dried over anhyd MgSO$_4$, filtered and concentrated in vacuo. Purification by flash column chromatography (10% ethyl acetate in heptane) afforded the title compound as a colorless oil (293 mg).

Step 2: Preparation of Tert-Butyl-{[4'-(2-benzylbenzofuran-3-yl)biphenyl-4-sulfonyl]-(3-trifluoromethyl-benzyl)amino}acetate.

A solution of 2-benzyl-3-[4'-(4,4,5,5-tetramethyl-[1,3,2]-dioxaborolan-2-yl)phenyl]-benzofuran (268 mg 0.653 mmol) in anhyd DMSO (5 mL) was added to a stirred suspension of tert-Butyl-[(4-bromobenzenesulfonyl)-(3-trifluoromethylbenzyl)amino]-acetate (296 mg, 0.58 mmol) and tripotassium phosphate (0.37 g, 1.76 mmol) in anhyd DMSO (5 mL). [1,1'-Bis(diphenylphosphino)ferrocene]dichloropalladium(II)-DCM complex (60 mg, 0.07 mmol) was added as a solid, and the resulting suspension was heated to 80° C. for 25 h. The reaction mixture was cooled to room temperature, diluted with ethyl acetate, filtered though celite, and washed with sat'd aq LiCl (3×10 mL), sat'd aq NaCl (1×10 mL), dried over anhyd MgSO$_4$, filtered and concentrated in vacuo. Purification by flash column chromatography (heptane) afforded the title compound as a white solid (95 mg).

Step 3: [[4'-(2-Benzyl-benzofuran-3-yl)biphenyl-4-sulfonyl]-(3-trifluoromethylbenzyl)-amino]acetic acid.

Tert-Butyl-{[4'-(2-benzylbenzofuran-3-yl)biphenyl-4-sulfonyl]-(3-trifluoromethyl-benzyl)amino}acetate (90 mg) was dissolved in methylene chloride (4 mL). TFA (1 mL) was added and the reaction mixture was stirred at room temperature for 16 h, and then concentrated in vacuo. Purification by flash column chromatography (5% methanol in methylene chloride) afforded the title compound as an off white solid (45 mg).

Example 19

Preparation of N-[4'-(2-Butyl-benzofuran-3-ylmethyl)-4-(3-phenyl-propoxy)-biphenyl-3-yl]-oxalamic acid

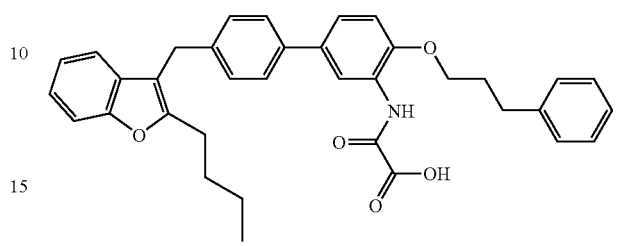

Step 1: (4-Bromo-phenyl)-(2-butyl-benzofuran-3-yl)-methanone

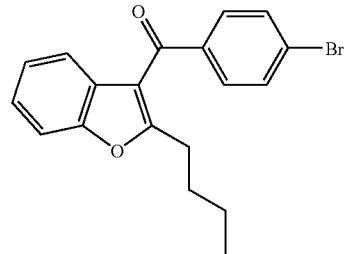

A solution of 2-n-butylbenzofurane (19.8 g, 114 mmol) and 4-bromobenzoyl chloride (25.0 g, 114 mmol) in dry dichloromethane (300 mL, 0.4 M) was cooled to 0° C. and treated with AlCl$_3$ (16.6 g, 1.1 equiv., 125.4 mmol) in 3 portions. After the additions were complete, the solution was stirred for 3 h and carefully added to ice water. After separation, the aqueous layer was extracted with dichloromethane (2×200 mL) and the combined organic layers were washed with water, sat'd aq NaCl, dried over anhydrous MgSO$_4$, filtered and concentrated in vacuo. Purification by flash column chromatography (1-2% ethyl acetate in heptane) afforded (4-bromo-phenyl)-(2-butyl-benzofuran-3-yl)-methanone (14.6 g, 36%).

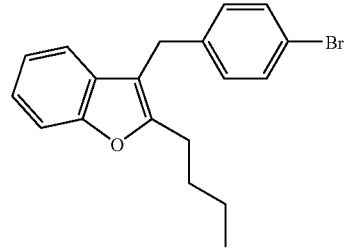

Step 2: 3-(4-Bromo-benzyl)-2-butyl-benzofuran

A solution of (4-bromo-phenyl)-(2-butyl-benzofuran-3-yl)-methanone (2.25 g, 6.32 mmol) in ethanol (20 mL, 0.3 M) was cooled to 0° C. and treated with NaBH$_4$ (0.263 g, 1.1 equiv, 6.95 mmol). After stirring for 1 h, the mixture was poured into a 50% ether in water solution (200 mL). After separation, the aqueous layer was extracted with ether (50 mL) and the combined organic layers were washed with water, sat'd aq NaCl, dried over anhydrous MgSO₄, filtered and concentrated in vacuo. The resulting alcohol was subsequently disolved in dry dichloromethane (50 mL), cooled to 0° C. and treated with triethylsilane (2.0 mL, 2.0 equiv., 12.64 mmol) dropwise via syringe. After stirring an additional 5 min, trifluoroacetic acid (2.43 mL, 5.0 equiv., 31.6 mmol) was added over 2 min and the mixture was stirred for 3 h. Once complete, the solution was washed with water, sat'd aq NaCl, dried over anhydrous MgSO₄, filtered and concentrated in vacuo. Purification by flash column chromatography (0-2% ethyl acetate in heptane) afforded 3-(4-bromo-benzyl)-2-butyl-benzofuran as a pale yellow oil (1.34 g, 63%).

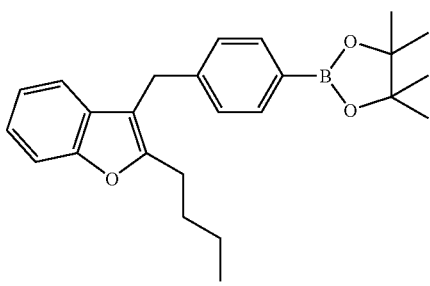

Step 3: 2-Butyl-3-[4-(4,4,5,5-tetramethyl-[1,3,2]dioxaborolan-2-yl)-benzyl]-benzofuran A solution of 3-(4-bromo-benzyl)-2-butyl-benzofuran (14.03 g, 41.5 mmol), bis(pinacolato)diborane (11.60 g, 1.1 equiv., 45.7 mmol), potassium acetate (12.2 g, 3.0 equiv., 125 mmol) in DMSO (100 mL, 0.4 M) was treated with PdCl₂(dppf).CH₂Cl₂ (4.15 g, 0.1 equiv., 4.15 mmol) and heated to 80° C. After compete by TLC, the solution was coled to room temperature, diluted with water (150 mL) and filtered through celite (washed with ether, 500 mL). After separation, the aqueous layer was extracted with ether (2×150 mL). The combined organic layers were washed with water, sat'd aq NaCl, dried over anhydrous MgSO₄, filtered and concentrated in vacuo. Purification by flash column chromatography (2-5% ethyl acetate in heptane) afforded 2-butyl-3-[4-(4,4,5,5-tetramethyl-[1,3,2]dioxaborolan-2-yl)-benzyl]-benzofuran as a pale yellow oil (11.2 g, 69%).

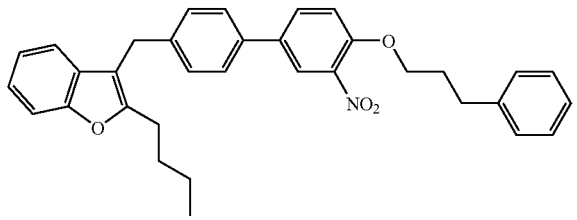

Step 4: 2-Butyl-3-[3'-nitro-4'-(3-phenyl-propoxy)-biphenyl-4-ylmethyl]-benzofuran A solution of 2-butyl-3-[4-(4,4,5,5-tetramethyl-[1,3,2]dioxaborolan-2-yl)-benzyl]-benzofuran (100 mg, 0.256 mmol), 4-bromo-2-nitro-1-(3-phenylpropylox)-benzene (95 mg, 1.1 equiv., 0.282 mmol) and K₂CO₃ (136 mg, 3.5 equiv., 0.987 mmol) in water (1 mL) and DMF (2 mL) was treated with PdCl₂(dppf).CH₂Cl₂ (23 mg, 0.1 equiv., 0.0282 mmol) and heated to 120° C. After complete (by TLC) the solution was cooled to room temperature, acidified to pH<4 with 10% aq HCl and diluted with water (20 mL). After separation, the aqueous layer was extracted with ether (3×20 mL) and the combined organic layers were washed with water, sat'd aq NaCl, dried over anhydrous MgSO₄, filtered and concentrated in vacuo. Purification by prep thin layer chromatography afforded 2-butyl-3-[3'-nitro-4'-(3-phenyl-propoxy)-biphenyl-4-ylmethyl]-benzofuran (53 mg, 41%).

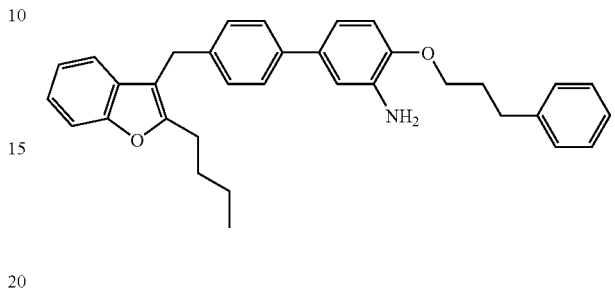

Step 5: 4'-(2-Butyl-benzofuran-3-ylmethyl)-4-(3-phenyl-propoxy)-biphenyl-3-ylamine A solution of 2-butyl-3-[3'-nitro-4'-(3-phenyl-propoxy)-biphenyl-4-ylmethyl]-benzofuran (53 mg, 0.105 mmol) in ethanol (1 mL) and acetic acid (1 mL) was treated with Fe (26.4 mg, 4.5 equiv., 0.472 mmol) and heated to 120° C. for 3 h. After cooling to room temperature, the solution was poured into a 20% aq NaOH/ice water solution (Ph>8) and extracted with ether (3×20 mL). The combined organic layers were washed with water, sat'd aq NaCl, dried over anhydrous MgSO₄, filtered and concentrated in vacuo. Purification by prep thin layer chromatography (25% ethyl acetate in heptane) afforded 4'-(2-butyl-benzofuran-3-ylmethyl)-4-(3-phenyl-propoxy)-biphenyl-3-ylamine (14.5 mg, 29%).

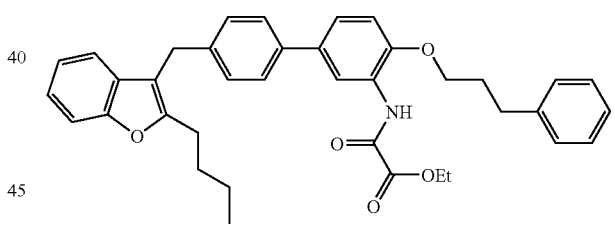

Step 6: N-[4'-(2-Butyl-benzofuran-3-ylmethyl)-4-(3-phenyl-propoxy)-biphenyl-3-yl]-oxalamic acid ethyl ester A solution of 4'-(2-butyl-benzofuran-3-ylmethyl)-4-(3-phenyl-propoxy)-biphenyl-3-ylamine (129 mg, 0.264 mmol) and diisopropylethylamine (0.115 mL, 2.5 equiv., 0.66 mmol) in dichloromethane (5 mL) was treated with a solution of ethyl chlorooxoacetate (44 mg, 1.2 equiv., 0.317 mmol) in dichloromethane (1 mL). After stirring for 2 h, the solution was diluted with water and extracted with dichloromethane (2×15 mL). The combined organic layers were washed with water, sat'd aq NaCl, dried over anhydrous MgSO₄, filtered and concentrated in vacuo. Purification by prep thin layer chromatography (25% ethyl acetate in heptane) afforded N-[4'-(2-butyl-benzofuran-3-ylmethyl)-4-(3-phenyl-propoxy)-biphenyl-3-yl]-oxalamic acid ethyl ester (120 mg, 77%).

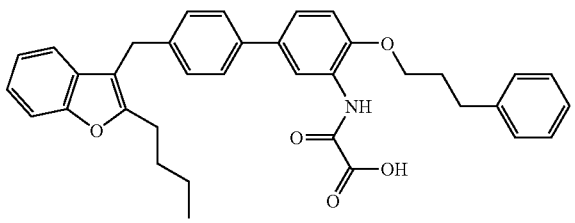

Step 7: N-[4'-(2-Butyl-benzofuran-3-ylmethyl)-4-(3-phenyl-propoxy)-biphenyl-3-yl]-oxalamic acid A solution of N-[4'-(2-butyl-benzofuran-3-ylmethyl)-4-(3-phenyl-propoxy)-biphenyl-3-yl]-oxalamic acid ethyl ester (120 mg, 0.204 mmol) in ethanol (3 mL) was treated with aq 1 N NaOH (0.3 mL, 1.5 equiv., 0.306 mmol) and stirred at room temperature. After stirring 1 h, the solution was acidified to pH<4 with 10% HCl, concentrated and purified by prep thin layer chromatography (10% methanol in dichloromethane) afforded N-[4'-(2-Butyl-benzofuran-3-ylmethyl)-4-(3-phenyl-propoxy)-biphenyl-3-yl]-oxalamic acid (32 mg, 28%). $R_f$ 0.39 (10% methanol in dichloromethane), $^1$H NMR (DMSO-$d_6$, 300 MHz) δ 10.26 (s, 1H), 8.58 (d, J=2.1 Hz, 1H), 7.43-7.05 (m, 16H), 4.07 (t, J=6.0 Hz, 2H), 3.95 (s, 2H), 2.82-2.77 (m, 4H), 2.13-1.97 (m, 2H), 1.67-1.59 (m, 2H), 1.37-1.24 (m, 2H), 0.86 (t, J=7.5 Hz, 3H).

Example 20

Preparation of 4-[4'-(2-benzylbenzofuran-3-yl)biphen-4-yl]-4-oxobutyric acid

Step 1. 5-[2-(4-Bromophenyl)-2-oxoethyl]-2,2-dimethyl-[1,3]dioxane-4,6-dione

A solution of Meldrum's acid (5.0 g, 35 mmol) in anhydrous THF (25 mL) was added cautiously to a stirred suspension of sodium hydride (95%, 960 mg, 38 mmol) in anhydrous THF (25 mL). The resulting solution was stirred at room temperature for 1 hr. A solution of 2,4'-dibromoacetophenone (11.6 g, 42 mmol) in anhydrous THF (25 mL) was added dropwise, and the resultant solution was stirred at room temperature for 16-24 hrs (TLC control). The reaction mixture was poured into water (50 mL), acidified to pH 2-3 with 0.5N hydrochloric acid and extracted with ethyl acetate (3×50 mL). The combined extract was washed with water, brine, dried over anhydrous MgSO$_4$, filtered and concentrated in vacuo. Trituration and filtration from MeOH afforded the title compound as a white solid (6.56 g).

Step 2. 2-Benzyl-3-[4-(4,4,5,5-tetramethyl-[1,3,2]-dioxaborolan-2-yl)phenyl]-benzofuran A solution of bis-(pinacolato)diboron (2.64 g, 10.41 mmol) in anhydrous DMSO (20 mL) was added to a stirred suspension of the known triflate, trifluoromethanesulfonic acid-4-(2-benzylbenzofuran-3 yl)phenyl ester, (4.09 g, 9.47 mmol) and potassium acetate (3.71 g, 37.9 mmol) in anhydrous DMSO (20 mL). [1,1'-bis-(Diphenylphosphino)-ferrocene]dichloropalladium(II)-DCM complex (770 mg, 0.95 mmol) was added as a solid, and the resulting suspension was heated to 80° C. for 4 hrs. The reaction mixture was cooled to room temperature, diluted with diethyl ether (150 mL), washed with water (2×50 mL), brine (3×50 mL), dried over anhydrous MgSO$_4$, filtered and concentrated in vacuo. Purification of the product by flash column chromatography, using 10% ethyl acetate/heptane as eluent, afforded the title compound as a white solid (2.96 g).

Step 3. 5-(2-[4'-(2-Benzylbenzofuran-3-yl)-biphen-4-yl]-2-oxoethyl)-2,2-dimethyl-[1,3]-dioxane-4,6-dione A solution of 2-benzyl-3-[4'-(4,4,5,5-tetramethyl-[1,3,2]-dioxaborolan-2-yl)phenyl]-benzofuran (500 mg, 1.22 mmol) in anhydrous DMSO (5 mL) was added to a stirred suspension of 5-[2-(4-bromophenyl)-2-oxoethyl]-2,2-dimethyl-[1,3]dioxane-4,6-dione (436 mg, 1.22 mmol) and tripotassium phosphate (1.04 g, 4.88 mmol) in anhydrous DMSO (5 mL). [1,1'-bis-(Diphenylphosphino)ferrocene]dichloropalladium (II)-DCM complex (100 mg, 0.12 mmol) was added as a solid, and the resulting suspension was heated to 80° C. for 2 hrs. The reaction mixture was cooled to room temperature, diluted with diethyl ether (150 mL), washed with water (2×50 mL), brine (3×50 mL), dried over anhydrous MgSO$_4$, filtered and concentrated in vacuo. Purification of the product by flash column chromatography, using 50-60% ethyl acetate/heptane as eluent, afforded the title compound as an off-white solid (502 mg): 1H-NMR (DMSO-d6, 300 MHz): δ 8.12 (2H, d, J=8 Hz, Ar-H), 7.92 (4H, d, J=6 Hz, Ar-H), 7.53-7.69 (4H, m, Ar-H), 7.26 (7H, m, Ar-H), 4.82 (1H, s, CH), 4.26 (2H, s, PhCH$_2$), 3.86 (2H, CH$_2$CO), 1.84 (3H, s, Me), 1.74 (3H, s, Me).

Step 4. 4-[4'-(2-benzylbenzofuran-3-yl)biphen-4-yl]-4-oxobutyric acid

2N Hydrochloric acid (1 mL) was added to a stirred solution of 5-{2-[4'-(2-benzyl-benzofuran-3-yl)-biphen-4-yl]-2-oxoethyl}-2,2-dimethyl-[1,3]-dioxane-4,6-dione (200 mg, 0.36 mmol) in THF (10 mL), and the resultant solution was heated at 70° C. for 6 hrs and then cooled to room temperature and concentrated in vacuo. The resulting solid was redissolved in DMSO (10 mL), and heated to 150° C. for 3 hrs before being cooled to room temperature, and diluted with water (20 mL), and extracted with ethyl acetate (3×20 mL). The combined extract was washed with water (2×10 mL), brine (3×10 mL), dried over anhydrous MgSO$_4$, filtered and concentrated in vacuo. Purification of the product by trituration and filtration from MeOH afforded the title compound as a white solid (105 mg, 62%). Rf: 0.20 (5% methanol in dichloromethane); 1H-NMR (CDCl$_3$, 300 MHz): δ 8.10 (2H, d, J=8 Hz, Ar-H), 7.80 (5H, m, Ar-H), 7.62 (1H, d, J=8 Hz, Ar-H), 7.48 (1H, d, J=8 Hz, Ar-H), 7.29 (6H, m, Ar-H), 4.26 (2H, s, PhCH$_2$), 3.86 (2H, t, J=6 Hz), 2.86 (2H, t, J=6 Hz); ESI-LCMS e/z calcd for $C_{31}H_{24}O_4$: 460.527, found 461 (M+H)$^+$.

Example 21

3-(4'-dibenzofuran-4-yl-biphen-4-ylmethylsulfanyl)-propanoic acid

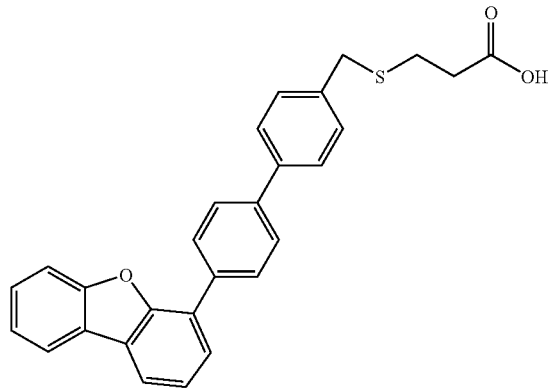

Step 1. 3-(4-bromophenylmethylsulfanyl)-propanoic acid methyl ester

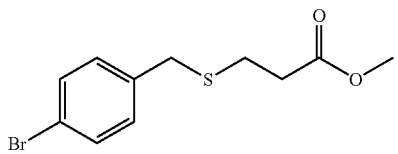

A solution of 3-thiolpropanoic acid methyl ester (1.2 g, 10 mmol) and 4-bromobenzyl-bromide (2.5 g, 10 mmol) in DMF (20 mL) was cooled to 0° C. and treated with $Cs_2CO_3$ (3.9 g, 12 mmol). After stirred for 2 h, the reaction was quenched with 5% HCl (25 mL) and diluted with ethyl acetate (50 mL). After seperation, the aqueous layer extracted with ethyl acetate (3×15 mL). The combined organic layers were washed with sat. aq NaCl, dried over $MgSO_4$ and concentrated. Purification by flash column chromatography (2-5% ethyl acetate in heptane) provided 3-(4-bromophenylmethylsulfanyl)-propanoic acid methyl ester (2.5 g, 87%) as white solid. $^1$H NMR (CDCl$_3$), 7.43 (d, J=8 Hz, 2H), 7.20 (d, J=8 Hz, 2H), 3.68 (s, 5H), 2.67 (m, 2H), 2.56 (t, J=6 Hz, 2H).

Step 2. 3-(4'-dibenzofuran-4-yl-biphen-4-ylmethylsulfanyl)-propanoic acid methyl ester

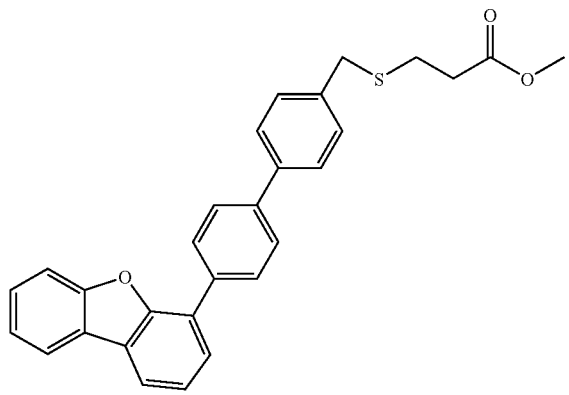

A solution of 3-(4-bromophenylmethylsulfanyl)-propanoic acid methyl ester (289 mg, 1 mmol), 4-(4-dibenzofuranyl)benzeneboronic acid (302 mg, 1.05 mmol) and Pd(PPh$_3$)$_4$ (52 mg, 5 mol %) in toluene (10 mL) and ethanol (3.0 mL) was treated with 2 M K$_2$CO$_3$ (1.5 mL). The reaction mixture was heated to reflux for 2 h, cooled to room temperature, diluted with ethyl acetate (100 mL). The organic layer was washed successively with 2% aq HCl and sat. aq NaCl, dried over MgSO$_4$ and concentrated. Purification by flash column chromatography (2-10% ethyl acetate in heptane) gave 3-(4'-dibenzofuran-4-yl-biphen-4-ylmethylsulfanyl)-propanoic acid methyl ester (330 mg, 72%) as white solid. $^1$H NMR (CDCl$_3$), 8.01 (d, J=8 Hz, 2H), 7.94 (d, J=8 Hz, 2H), 7.78 (d, J=8 Hz, 2H), 7.66 (m, 4H), 7.42 (m, 5H), 3.81 (s, 2H), 3.71 (s, 3H), 2.76 (t, J=6 Hz, 2H), 2.56 (t, J=6 Hz, 2H). LCMS 475 (M$^+$+23).

Step 3. 3-(4'-dibenzofuran-4-yl-biphen-4-ylmethylsulfanyl)-propanoic acid

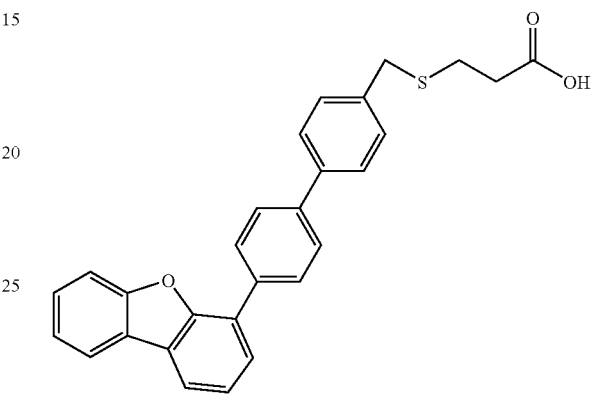

A solution of 3-(4'-dibenzofuran-4-yl-biphen-4-ylmethylsulfanyl)-propanoic acid methyl ester (210 mg, 0.46 mmol) in THF (2 mL) and methanol (2 mL) was cooled to 0° C. and treated with 2 N KOH (1.0 mL). After stirring at room temperature for 1 h the solution was acidified with 10% HCl to pH 2 and diluted with ethyl acetate (25 mL). After being seperated, the aqueous layer was extracted with ethyl acetate (3×15 mL) and the combined organic layers were dried over MgSO$_4$ and concentrated. Purification by flash column chromatography (2-5% methanol in dichloromethane) provided 3-(4'-dibenzofuran-4-yl-biphen-4-ylmethylsulfanyl)-propanoic acid (180 mg, 90%) as white solid. $^1$H NMR (CDCl$_3$), 8.01 (d, J=8 Hz, 2H), 7.94 (d, J=8 Hz, 2H), 7.78 (d, J=8 Hz, 2H), 7.66 (m, 4H), 7.42 (m, 5H), 3.82 (s, 2H), 3.82 (s, 2H), 2.76 (m, 2H), 2.56 (t, J=6 Hz, 2H). LCMS 462 (M$^+$+23).

Example 22

3-(4'-dibenzofuran-4-yl-biphen-4-ylmethylsulfanyl)-2-methylpropanoic acid 3-(4-bromophenylmethylsulfanyl)-2-methylpropanoic acid methyl ester A solution of 3-bromo-2-methylpropanoic acid methyl ester (0.366 g, 2 mmol) and 4-bromobenzylthiol (0.402 g, 2 mmol) in DMF (5 mL) was cooled to 0° C. and treated with K$_2$CO$_3$ (414 g, 3 mmol). After stirring for 2 h, the reaction was quenched with 5% HCl (15 mL) and diluted with ethyl acetate (50 mL). After seperation, the aqueous layer extracted with ethyl acetate (3×15 mL). The combined organic layers were washed with sat. aq NaCl, dried over MgSO$_4$ and concentrated. Purification by flash column chromatography (5% ethyl acetate in heptane) provided 3-(4-bromophenylmethylsulfanyl)-2-methylpropanoic acid methyl ester (430 mg, 71%) as white solid. $^1$H NMR (CDCl$_3$), 7.43 (d, J=8 Hz, 2H), 7.20 (d, J=8 Hz, 2H), 3.69 (s, 3H), 3.65 (s, 2H), 2.67 (m, 2H), 2.45 (q, J=6 Hz, 1H), 1.21 (d, J=7 Hz, 3H).

Step 1. 3-(4'-dibenzofuran-4-yl-biphen-4-ylmethylsulfanyl)-2-methylpropanoic acid methyl ester A solution of 3-(4-bromophenylmethylsulfanyl)-2-methylpropanoic acid methyl ester (0.427 g, 1 mmol), 4-(4-dibenzofuranyl)benzeneboronic acid (0.302 g, 1.05 mmol) and Pd(PPh$_3$)$_4$ (0.052 g, 5 mol %) in toluene (10 mL) and ethanol (3.0 mL) was treated with 2 M K$_2$CO$_3$ (1.5 mL). The reaction mixture was heated to reflux for 2 h, cooled to room temperature, diluted with ethyl acetate (100 mL). The organic layer was washed successively with 2% aq HCl and sat. aq NaCl, dried over MgSO$_4$ and concentrated. Purification by flash column chromatography (2-10% ethyl acetate in heptane) gave 3-(4'-dibenzofuran-4-yl-biphen-4-ylmethylsulfanyl)-propanoic acid methyl ester (312 mg, 67%) as an oil. $^1$H NMR (CDCl$_3$), 8.01 (d, J=8 Hz, 2H), 7.94 (d, J=8 Hz, 2H), 7.78 (d, J=8 Hz, 2H), 7.66 (m, 4H), 7.42 (m, 5H), 3.79 (s, 2H), 3.71 (s, 3H), 2.76 (m, 2H), 2.56 (q, J=6 Hz, 1H). LCMS 480 (M$^+$+23).

Step 2. 3-(4'-dibenzofuran-4-yl-biphen-4-ylmethylsulfanyl)-2-methylpropanoic acid A solution of 2-tert-butoxycarbonylamino-3-(4'-dibenzofuran-4-yl-biphen-4-yl)-propanoic acid methyl ester (0.28 g, 0.6 mmol) in THF (2 mL) and methanol (2 mL) was cooled to 0° C. and treated with 2 N KOH (1.0 mL). After stirring at room temperature for 1 h the solution was acidified with 10% HCl to pH 2 and diluted with ethyl acetate (25 mL). After being seperated, the aqueous layer was extracted with ethyl acetate (3×15 mL) and the combined organic layers were dried over MgSO$_4$ and concentrated. Purification by flash column chromatography (2-5% methanol in dichloromethane) provided 3-(4'-dibenzofuran-4-yl-biphen-4-ylmethylsulfanyl)-propanoic acid (245 mg, 91%) as white solid. $^1$H NMR (CDCl$_3$), 8.01 (d, J=8 Hz, 2H), 7.94 (d, J=8 Hz, 2H), 7.78 (d, J=8 Hz, 2H), 7.66 (m, 4H), 7.42 (m, 5H), 3.81 (s, 2H), 2.76 (m, 2H), 2.56 (q, J=6 Hz, 1H). LCMS 476 (M$^+$+23).

Example 23

3-(4'-dibenzofuran-4-yl-biphen-4-ylmethylsulfanyl)-2,2-dimethylpropanoic acid

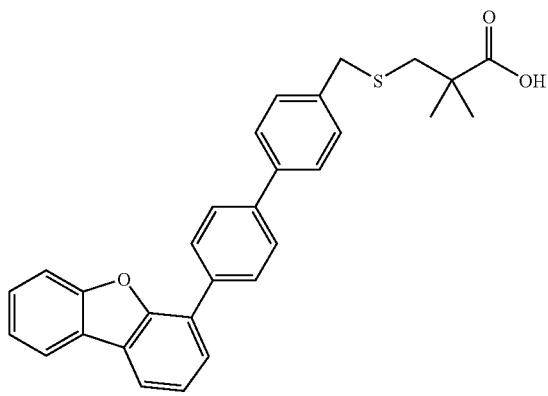

Step 1. 3-(4-bromophenylmethylsulfanyl)-2,2-dimethylpropanoic acid methyl ester

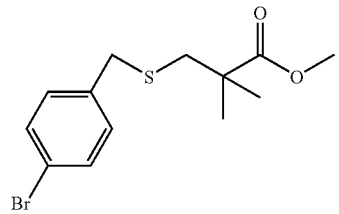

A solution of 3-bromo-2,2-dimethyllpropanoic acid methyl ester (0.39 g, 2 mmol) and 4-bromobenzylthiol (0.402 g, 2 mmol) in DMF (5 mL) was cooled to 0° C. and treated with K$_2$CO$_3$ (0.414 g, 3 mmol). After stirring for 2 h, the reaction was quenched with 5% HCl (15 mL) and diluted with ethyl acetate (50 mL). After seperation, the aqueous layer extracted with ethyl acetate (3×15 mL). The combined organic layers were washed with sat. aq NaCl, dried over MgSO$_4$ and concentrated. Purification by flash column chromatography (5% ethyl acetate in heptane) provided 3-(4-bromophenylmethylsulfanyl)-2,2-dimethylpropanoic acid methyl ester (260 mg, 35%) as white solid. $^1$H NMR (CDCl$_3$), 7.43 (d, J=8 Hz, 2H), 7.18 (d, J=8 Hz, 2H), 3.69 (s, 5H), 2.63 (s, 2H), 1.21 (s, 6H).

Step 2. 3-(4'-dibenzofuran-4-yl-biphen-4-ylmethylsulfanyl)-2-dimethylpropanoic acid methyl ester

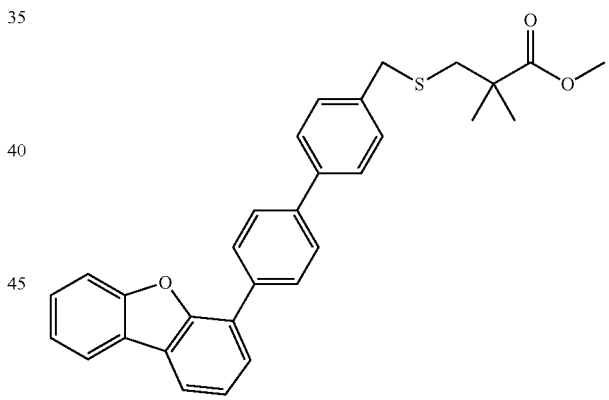

A solution of 3-(4-bromophenylmethylsulfanyl)-2-methylpropanoic acid methyl ester (0.260 g, 0.82 mmol), 4-(4-dibenzofuranyl)benzeneboronic acid (0.236 g, 086 mmol) and Pd(PPh$_3$)$_4$ (0.052 g, 5 mol %) in toluene (10 mL) and ethanol (3.0 mL) was treated with 2 M K$_2$CO$_3$ (1.5 mL). The reaction mixture was heated to reflux for 2 h, cooled to room temperature, diluted with ethyl acetate (100 mL). The organic layer was washed successively with 2% aq HCl and sat. aq NaCl, dried over MgSO$_4$ and concentrated. Purification by flash column chromatography (2-10% ethyl acetate in heptane) gave 3-(4'-dibenzofuran-4-yl-biphen-4-ylmethylsulfanyl)-propanoic acid methyl ester (280 mg, 67%) as an oil. $^1$H NMR (CDCl$_3$), 8.01 (d, J=8 Hz, 2H), 7.94 (d, J=8 Hz, 2H), 7.78 (d, J=8 Hz, 2H), 7.66 (m, 4H), 7.42 (m, 5H), 3.79 (s, 2H), 3.71 (s, 3H), 2.73 (s, 2H), 1.27 (s, 6H). LCMS 504 (M$^+$+23).

Step 3. 3-(4'-dibenzofuran-4-yl-biphen-4-ylmethylsulfanyl)-2-dimethylpropanoic acid

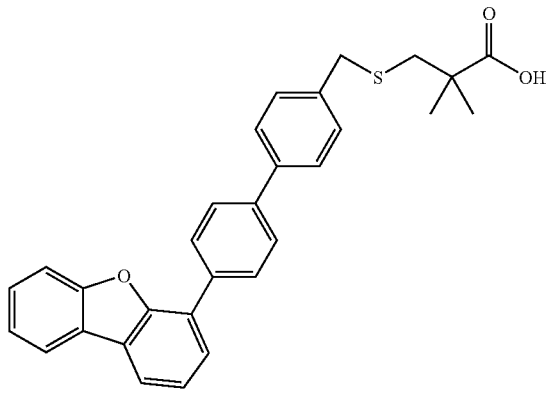

A solution of 2-tert-butoxycarbonylamino-3-(4'-dibenzofuran-4-yl-biphen-4-yl)-propanoic acid methyl ester (0.125 g, 0.26 mmol) in THF (2 mL) and methanol (2 mL) was cooled to 0° C. and treated with 2 N KOH (1.0 mL). After stirring at room temperature for 1 h the solution was acidified with 10% HCl to pH 2 and diluted with ethyl acetate (25 mL). After being seperated, the aqueous layer was extracted with ethyl acetate (3×15 mL) and the combined organic layers were dried over MgSO₄ and concentrated. Purification by flash column chromatography (2-5% methanol in dichloromethane) provided 3-(4'-dibenzofuran-4-yl-biphen-4-ylmethylsulfanyl)-propanoic acid (80 mg, 67%) as white solid. $^1$H NMR (CDCl₃), 8.01 (d, J=8 Hz, 2H), 7.94 (d, J=8 Hz, 2H), 7.78 (d, J=8 Hz, 2H), 7.66 (m, 4H), 7.42 (m, 5H), 3.82 (s, 2H), 2.76 (s, 2H), 1.32 (s, 6H). LCMS 490 (M⁺+23).

Example 24

2-(4'-dibenzofuran-4-yl-biphen-4-ylmethylsulfanyl)-3-methylbutanoic acid (4-bromophen-yl-4-methylsulfanyl)-3-methylbutanoic acid ethyl ester A solution of 2-bromo-3-methyllpropanoic acid ethyl ester (0.418 g, 2 mmol) and 4-bromobenzylthiol (0.402 g, 2 mmol) in DMF (5 mL) was cooled to 0° C. and treated with K₂CO₃ (0.414 g, 3 mmol). After stirring for 2 h, the reaction was quenched with 5% HCl (15 mL) and diluted with ethyl acetate (50 mL). After seperation, the aqueous layer extracted with ethyl acetate (3×15 mL). The combined organic layers were washed with sat. aq NaCl, dried over MgSO₄ and concentrated. Purification by flash column chromatography (5% ethyl acetate in heptane) provided (4-bromophen-yl-4-methylsulfanyl)-3-methylbutanoic acid ethyl ester (660 mg, 90%) as white solid. $^1$H NMR (CDCl₃), 7.43 (d, J=8 Hz, 2H), 7.18 (d, J=8 Hz, 2H), 4.17 (q, J=6 Hz, 2H), 3.75 (s, 2H), 2.85 (d, J=9 Hz, 1H), 2.04 (m, 1H), 1.29 (t, J=6 Hz, 3H), 1.02 (d, J=6 Hz, 3H), 0.98 (d. J=6 Hz, 3H).

Step 1. 2-(4'-dibenzofuran-4-yl-biphen-4-ylmethylsulfanyl)-3-methylbutanoic acid methyl ester A solution of (4-bromophen-yl-4-methylsulfanyl)-3-methylbutanoic acid methyl ester (0.331 g, 1 mmol), 4-(4-dibenzofuranyl)benzeneboronic acid (0.305 g, 1.05 mmol) and Pd(PPh₃)₄ (0.052 g, 5% mol) in toluene (10 mL) and ethanol (3.0 mL) was treated with 2 M K₂CO₃ (1.5 mL). The reaction mixture was heated to reflux for 2 h, cooled to room temperature, diluted with ethyl acetate (100 mL). The organic layer was washed successively with 2% aq HCl and sat. aq NaCl, dried over MgSO₄ and concentrated. Purification by flash column chromatography (2-10% ethyl acetate in heptane) gave 2-(4'-dibenzofuran-4-yl-biphen-4-ylmethylsulfanyl)-3-methylbutanoic acid methyl ester (336 mg, 70%) as an oil. $^1$H NMR (CDCl₃), 8.01 (d, J=8 Hz, 2H), 7.94 (d, J=8 Hz, 2H), 7.78 (d, J=8 Hz, 2H), 7.66 (m, 4H), 7.42 (m, 5H), 4.17 (q, J=6 Hz, 2H), 3.85 (s, 2H), 2.95 (d, J=9 Hz, 1H), 2.04 (m, 1H), 1.29 (t, J=6 Hz, 3H), 1.05 (d, J=6 Hz, 3H), 0.99 (d. J=6 Hz, 3H). LCMS 517 (M⁺+23).

Step 2. 2-(4'-dibenzofuran-4-yl-biphen-4-ylmethylsulfanyl)-3-methylbutanoic acid A solution of 2-tert-butoxycarbonylamino-3-(4'-dibenzofuran-4-yl-biphen-4-yl)-propanoic acid methyl ester (0.28 g, 0.566 mmol) in THF (2 mL) and methanol (2 mL) was cooled to 0° C. and treated with 2 N KOH (1.0 mL). After stirring at room temperature for 1 h the solution was acidified with 10% HCl to pH 2 and diluted with ethyl acetate (25 mL). After being seperated, the aqueous layer was extracted with ethyl acetate (3×15 mL) and the combined organic layers were dried over MgSO₄ and concentrated. Purification by flash column chromatography (2-5% methanol in dichloromethane) provided 2-(4'-dibenzofuran-4-yl-biphen-4-ylmethylsulfanyl)-3-methylbutanoic acid (195 mg, 74%) as white solid. 0.195 g (yield 73.8%). $^1$H NMR (CDCl₃), 8.01 (d, J=8 Hz, 2H), 7.94 (d, J=8 Hz, 2H), 7.78 (d, J=8 Hz, 2H), 7.66 (m, 4H), 7.42 (m, 5H), 3.85 (s, 2H), 2.95 (d, J=9 Hz, 1H), 2.12 (m, 1H), 1.05 (t, J=6 Hz, 6H). LCMS 489 (M⁺+23).

The following compounds are prepared essentially according to the procedures described in the schemes, charts, examples and preparations set forth herein.

Example 25

N-[3-Benzyloxy-4'-(2-butyl-benzofuran-3-ylmethyl)-biphenyl-4-yl]-oxalamic acid $R_f$ 0.19 (10% methanol in dichloromethane), $^1$H NMR (DMSO-d₆, 300 MHz) δ 9.78 (s, 1H), 8.31 (s, 1H), 7.48-7.08 (m, 16 H), 5.25 (s, 2H), 4.01 (s, 2H), 2.83 (t, J=7.5 Hz, 2H), 1.68-1.58 (m 2H), 1.37-1.27 (m, 2H), 0.87 (t, J=7.2 Hz, 3H); ESI-LCMS m/z calcd for C₃₄H₃₁NO₅: 533; found 532 (M−1)⁺.

Example 26

N-[3-Benzyloxy-4'-(2-butyl-benzofuran-3-ylmethyl)-biphenyl-4-yl]-malonamic acid $R_f$ 0.32 (10% methanol in dichloromethane), $^1$H NMR (CDCl₃, 300 MHz) δ 8.54 (s, 1H), 8.41 (s, 1H), 7.48-7.01 (m, 16H), 5.16 (s, 1H), 4.02 (s, 1H), 3.47 (s, 1H), 1.77-1.67 (m, 2H), 1.45-1.33 (m, 2H), 0.93 (t, J=7.2 Hz, 3H); ESI-LCMS m/z calcd for C₃₅H₃₃NO₅: 547; found 548 (M+1)⁺.

Example 27

N-[4-Benzyloxy-4'-(2-butyl-benzofuran-3-ylmethyl)-biphenyl-3-yl]-malonamic acid $R_f$ 0.34 (10% methanol in dichloromethane), $^1$H NMR (CDCl₃, 300 MHz) δ 8.54 (s, 1H), 8.34 (s, 1H), 7.48-7.01 (m, 16H), 5.16 (s, 2H), 4.02 (s, 2H), 3.50 (s, 2H), 2.79 (t, J=7.5 Hz, 2H), 1.75-1.67 (m, 2H), 1.45-1.37 (m, 2H), 0.93 (t, J=6.9 Hz, 3H); ESI-LCMS m/z calcd for C₃₅H₃₃NO₅: 547; found 548 (M+1)⁺.

Example 28

N-[4'-(2-Butyl-benzofuran-3-ylmethyl)-3-hydroxy-biphenyl-4-yl]-malonamic acid $R_f$ 0.53 (20% methanol in dichloromethane), $^1$H NMR (CDCl$_3$, 300 MHz) δ 9.22 (br s, 1H), 7.87 (br s, 1H) 7.40-6.99 (m, 11H), 3.95 (s, 2H), 3.56 (s, 2H), 2.72 (t, J=7.5 Hz, 2H), 1.68-1.49 (m, 2H), 1.36-1.28 (m, 2H), 0.86 (t, J=6.9 Hz, 3H); ESI-LCMS m/z calcd for C$_{28}$H$_{27}$NO$_5$: 457; found 458 (M+1)$^+$.

Example 29

N-[4'-(2-Butyl-benzofuran-3-ylmethyl)-4-hydroxy-biphenyl-3-yl]-malonamic acid

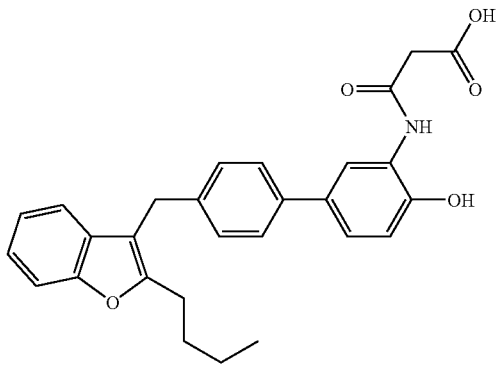

$R_f$ 0.53 (20% methanol in dichloromethane), $^1$H NMR (CDCl$_3$, 300 MHz) δ 9.22 (br s, 1H), 7.39-6.99 (m, 11H), 3.95 (s, 2H), 3.56 (s, 2H), 2.72 (t, J=7.5 Hz, 2H), 1.68-1.49 (m, 2H), 1.36-1.28 (m, 2H), 0.86 (t, J=6.9 Hz, 3H); ESI-LCMS m/z calcd for C$_{28}$H$_{27}$NO$_5$: 457; found 458 (M+1)$^+$.

Example 30

[4'-(2-Benzyl-benzofuran-3-yl)-3-fluoro-biphenyl-4-sulfonylamino]-acetic acid

Isolated as a white solid. $R_f$ 0.42 (20% Methanol-80% Methylene Chloride); $^1$H NMR (DMSO-d$_6$) 8.35 (br. s, 1H), 7.95-7.54 (m, 9H), 7.31-7.21 (m, 6H), 4.27 (s, 2H), 3.73 (s, 2H); LCMS m/z calcd for C$_{29}$H$_{22}$FNO$_5$S: 515.5 found 516.3 (M+1).

Example 31

{[4'-(2-Benzyl-benzofuran-3-yl)-3-fluoro-biphenyl-4-sulfonyl]-methyl-amino}-acetic acid

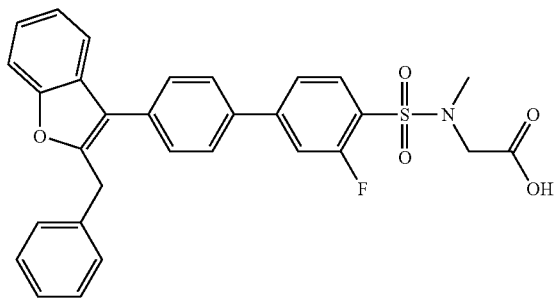

Isolated as an off-white solid. $R_f$ 0.32 (10% Methanol-90% Methylene Chloride); $^1$H NMR (CDCl$_3$) 7.98-7.24 (m, 15H), 4.26 (s, 2H), 4.21 (s, 2H), 3.04 (s, 3H); LCMS m/z calcd for C$_{30}$H$_{24}$FNO$_5$S: 529.57 found 530.3 (M+1).

Example 32

[[4'-(2-Benzyl-benzofuran-3-yl)-biphenyl-4-sulfonyl]-(3-nitro-benzyl)-amino]-acetic acid Isolated as a beige solid. $R_f$ 0.50 (10% Methanol-90% Methylene Chloride); $^1$H NMR (DMSO-d$_6$) 8.10-7.00 (m, 21H), 4.63 (s, 2H), 4.27 (s, 2H), 3.64 (s, 2H).

Example 33

[[4'-(2-Benzyl-benzofuran-3-yl)-biphenyl-4-sulfonyl]-(3-trifluoromethyl-benzyl)-amino]-acetic acid

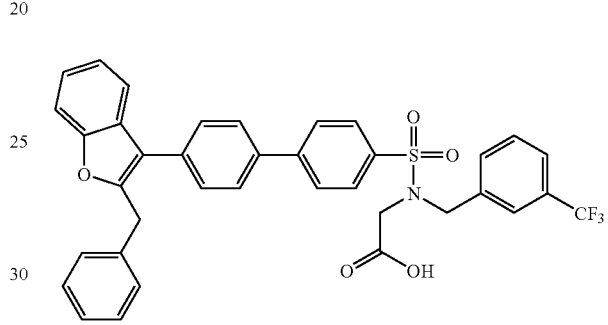

Isolated as a white foam., $R_f$ 0.61 (50% Ethyl Acetate-50% Heptane); $^1$H NMR (CDCl$_3$) 7.94 (d, J=7.5 Hz, 2H), 7.75-7.02 (m, 19H), 4.57 (s, 2H), 4.23 (s, 2H), 4.02 (s, 2H).

Example 34

[[4'-(2-Benzyl-benzofuran-3-yl)-biphenyl-4-sulfonyl]-(3-methoxy-benzyl)-amino]-acetic acid Isolated as a white foam. $R_f$ 0.62 (20% Methanol-80% Ethyl Acetate); $^1$H NMR (DMSO-d$_6$) 8.00-7.87 (m, 6H), 7.70-7.55 (4H), 7.36-7.17 (7H), 6.81-6.71 (m, 4H), 4.53 (s, 2H), 4.28 (s, 2H), 3.65 (s, 3H), 3.58 (s, 2H).

Example 35

[[4'-(2-Benzyl-benzofuran-3-yl)-biphenyl-4-sulfonyl]-(3-fluoro-benzyl)-amino]-acetic acid Isolated as an off-white solid. $R_f$ 0.38 (10% Methanol-90% Methylene Chloride); $^1$H NMR (DMSO-d$_6$) 7.92-7.90 (m, 6H), 7.70-7.56 (m, 4H), 7.35-7.23 (m, 8H), 7.07 (t, J=9.0 Hz, 3H), 4.52 (s, 2H), 4.29 (s, 2H), 3.75 (s, 2H).

Example 36

[[4'-(2-Benzyl-benzofuran-3-yl)-biphenyl-4-sulfonyl]-(3-trifluoromethyl-benzyl)-amino]-acetic acid Isolated as an off-white solid. $R_f$ 0.43 (10% Methanol-90% Methylene Chloride); $^1$H NMR (DMSO-d$_6$) 7.94-7.90 (m, 6H), 7.71-7.57 (m, 8H), 7.35-7.26 (m, 7H), 4.58 (s, 2H), 4.30 (s, 2H), 3.88 (s, 2H).

Example 37

2-[[4'-(2-Benzyl-benzofuran-3-yl)-biphenyl-4-sulfonyl]-(3-trifluoromethyl-benzyl)-amino]-4-methyl-pentanoic acid

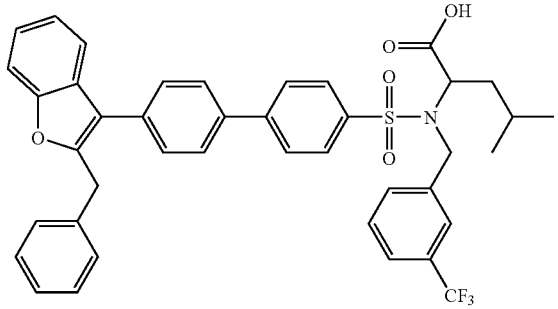

Isolated as white foam. $R_f$ 0.31 (10% Methanol-90% Methylene Chloride); $^1$H NMR (DMSO-$d_6$) 7.96-7.88 (m, 6H), 7.78-7.57 (m, 8H), 7.34-7.23 (m, 7H), 4.85 (d, J=17.1 Hz, 1H), 4.53 (d, J=16.8 Hz, 1H), 4.47-4.42 (m, 1H), 4.29 (s, 2H), 1.43-1.24 (m, 3H), 0.83 (d, J=6.0 Hz, 3H), 0.46 (d, J=6.3 Hz, 3H).

Example 38

2-[[4'-(2-Benzyl-benzofuran-3-yl)-biphenyl-4-sulfonyl]-(3-trifluoromethyl-benzyl)-amino]-butyric acid Isolated as a white foam. $R_f$ 0.37 (10% Methanol-90% Methylene Chloride); $^1$H NMR (DMSO-$d_6$) 7.93-7.85 (m, 6H), 7.74-7.54 (m, 7H), 7.34-7.23 (m, 7H), 4.76 (d, J=17.1 Hz, 1H), 4.53 (d, J=16.8 Hz, 1H), 4.34 (m, 1H), 4.32 (s, 2H), 1.78 (m, 1H), 1.47 (m, 1H), 0.75 (t, J=6.9 Hz, 3H).

Example 39

[(4'-Dibenzofuran-4-yl-biphenyl-4-sulfonyl)-(3-trifluoromethyl-benzyl)-amino]-acetic acid

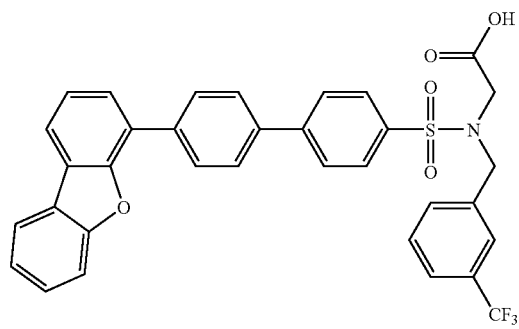

Isolated as a white foam. $R_f$ 0.24 (10% Methanol-90% Methylene Chloride); $^1$H NMR (DMSO-$d_6$) 12.8 (br s, 1H), 8.29 (s, 1H), 8.21-7.40 (m, 18H), 4.57 (s, 2H), 3.99 (s, 2H); LCMS m/z calcd for $C_{34}H_{24}F_3NO_5S$: 615.6 found 616.3 (M+1).

Example 40

2-[[4'-(2-Benzyl-benzofuran-3-yl)-biphenyl-4-sulfonyl]-(3-trifluoromethyl-benzyl)-amino]-propionic acid Isolated as a white foam. $R_f$ 0.24 (10% Methanol-90% Methylene Chloride); $^1$H NMR (DMSO-$d_6$) 7.01-6.91 (m, 6H), 6.79-8.71 (m, 8H), 6.41-6.31 (m, 7H), 4.00 (s, 2H), 3.94-3.83 (m, 2H), 3.69 (d, J=16.8 Hz, 1H), 0.46 (d, J=7.5 Hz, 3H); LCMS m/z calcd for $C_{38}H_{30}F_3NO_5S$: 669.7 found 670.3 (M+1).

Example 41

[(2-Phenoxy-[1,1';4',1"]terphenyl-4"-sulfonyl)-(3-trifluoromethyl-benzyl)-amino]-acetic acid

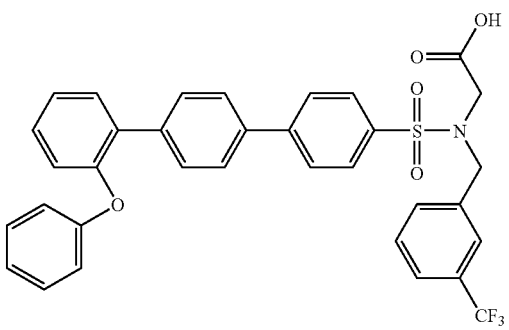

Isolated as a white foam. $R_f$ 0.22 (10% Methanol-90% Methylene Chloride); $^1$H NMR (DMSO-$d_6$ with TFA) 7.77-7.83 (m, 21H), 4.43 (s, 2H), 3.86 (s, 2H); LCMS m/z calcd for $C_{34}H_{26}F_3NO_5S$: 617.6 found 618.3 (M+1).

Example 42

[(4-Propyl-[1,1';4',1"]terphenyl-4"-sulfonyl)-(3-trifluoromethyl-benzyl)-amino]-acetic acid Isolated as a white foam. $R_f$ 0.30 (10% Methanol-90% Methylene Chloride); $^1$H NMR (DMSO-$d_6$) 7.93 (d, J=8.1 Hz, 2H), 7.76-7.63 (m, 6H), 7.55 (d, J=8.4 Hz, 2H), 7.49-7.41 (m, 4H), 7.28 (d, J=8.1 Hz, 2H), 4.58 (s, 2H), 3.98 (s, 2H), 2.66 (t, J=7.5 Hz, 2H), 1.70 (m, 2H), 0.99 (t, J=7.5 Hz, 3H); LCMS m/z calcd for $C_{31}H_{28}F_3NO_4S$: 567.62 found 566.3 (M+1)

Example 43
[(4'-Dibenzofuran-4-yl-biphenyl-4-sulfonyl)-(3-fluoro-benzyl)-amino]-acetic acid

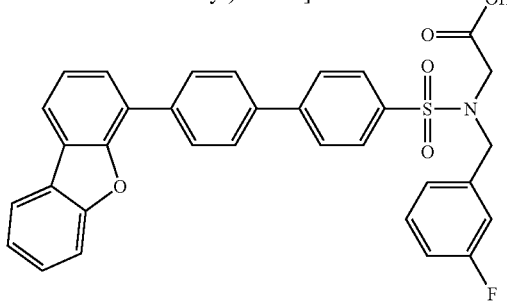

Isolated as an off-white solid. $R_f$ 0.48 (20% Methanol-80% Methylene Chloride); $^1$H NMR (DMSO-$d_6$) 12.80 (br s, 1H), 8.19-7.09 (m, 19H), 4.49 (s, 2H), 3.95 (s, 2H).

The following compounds are prepared essentially according to the procedures described in the schemes, charts, examples and preparations set forth herein.

| Ex. No. | Structure and/or Name |
|---|---|
| 44 | 4-({[10-(ethoxycarbonyl)pyrido[1,2-a]indol-3-yl]oxy}methyl)benzoic acid; |
| 45 | {[4'-(1-butylindolizin-2-yl)biphenyl-4-yl]oxy}acetic acid; |
| 46 | 4-{[4'-(1-butylindolizin-2-yl)biphenyl-4-yl]oxy}butanoic acid; |
| 47 | 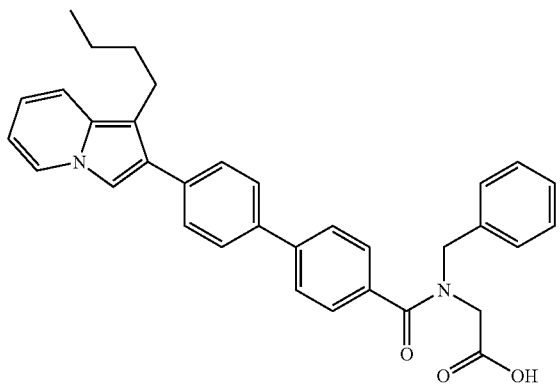<br>N-benzyl-N-{[4'-(1-butylindolizin-2-yl)biphenyl-4-yl]carbonyl}glycine; |
| 48 | N-[4'-(1-butylindolizin-2-yl)-4-(2-phenylethoxy)biphenyl-3-yl]glycine; |
| 49 | 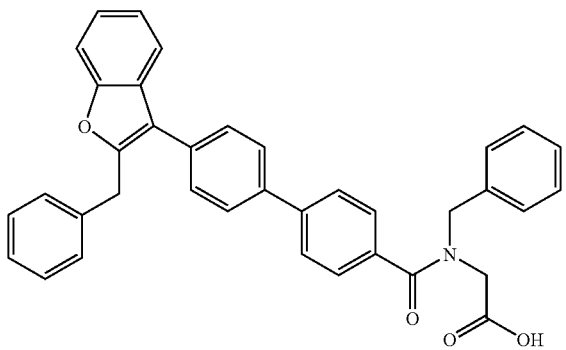<br>N-benzyl-N-{[4'-(2-benzyl-1-benzofuran-3-yl)biphenyl-4-yl]carbonyl}glycine; |
| 50 | {[4'-(2-benzyl-1-benzofuran-3-yl)biphenyl-4-yl]oxy}acetic acid; |

| Ex. No. | Structure and/or Name |
|---|---|
| 51 | 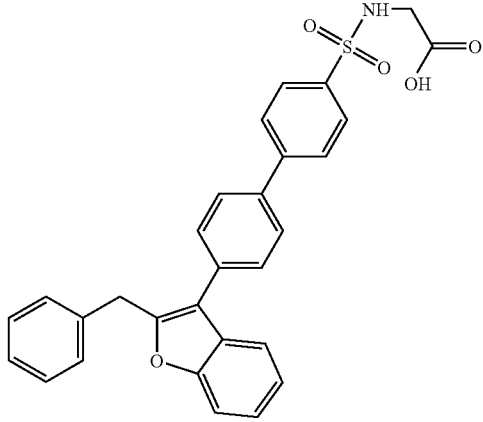<br>N-{[4'-(2-benzyl-1-benzofuran-3-yl)biphenyl-4-yl]sulfonyl}glycine; |
| 52 | 4-{[4'-(2-benzyl-1-benzofuran-3-yl)biphenyl-4-yl]oxy}butanoic acid; |
| 53 | 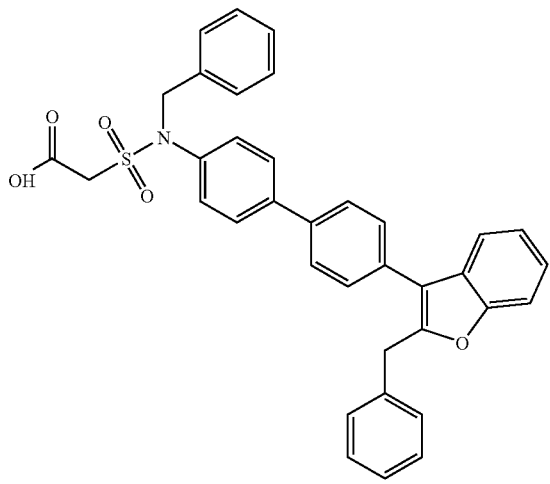<br>({benzyl[4'-(2-benzyl-1-benzofuran-3-yl)biphenyl-4-yl]amino}sulfonyl)acetic acid; |
| 54 | 3-{[4'-(2-Benzyl-benzofuran-3-yl)-biphenyl-4-carbonyl]-furan-2-ylmethyl-amino}-propionic acid; |
| 55 | 3-[4'-(2-benzyl-1-benzofuran-3-yl)biphenyl-4-yl]propanoic acid; |
| 56 | 4'-(2-benzyl-1-benzofuran-3-yl)biphenyl-4-carboxylic acid; |
| 57 | 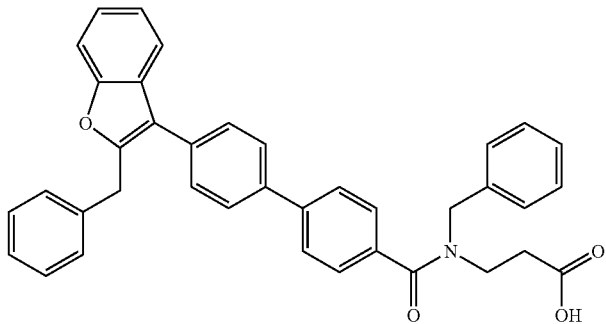<br>3-{Benzyl-[4'-(2-benzyl-benzofuran-3-yl)-biphenyl-4-carbonyl]-amino}-propionic acid; |
| 58 | {[4'-[(2-butyl-1-benzofuran-3-yl)methyl]-4-(3-phenylpropoxy)biphenyl-3-yl]amino}(oxo)acetic acid; |

| Ex. No. | Structure and/or Name |
|---|---|
| 59 | 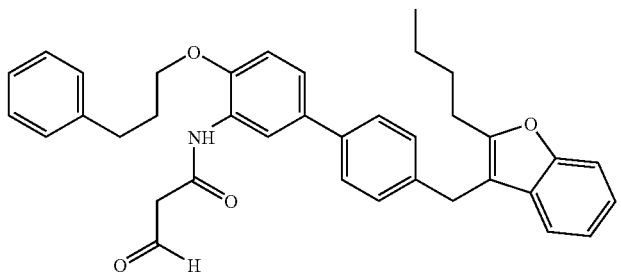<br>3-{[4'-[(2-butyl-1-benzofuran-3-yl)methyl]-4-(3-phenylpropoxy)biphenyl-3-yl]amino}-3-oxopropanoic acid; |
| 60 | N-benzyl-N-{[4'-(2-benzyl-1-benzofuran-3-yl)biphenyl-4-yl]methyl}glycine; |
| 61 | 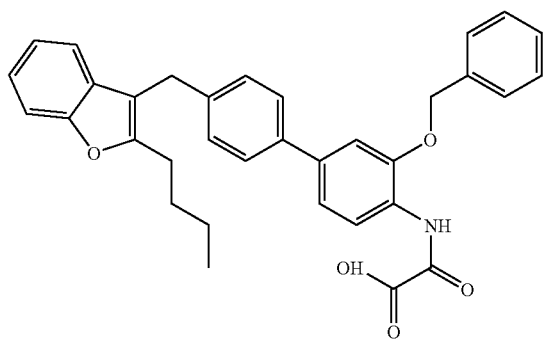<br>({3-(benzyloxy)-4'-[(2-butyl-1-benzofuran-3-yl)methyl]biphenyl-4-yl}amino)(oxo)acetic acid; |
| 62 | 3-({3-(benzyloxy)-4'-[(2-butyl-1-benzofuran-3-yl)methyl]biphenyl-4-yl}amino)-3-oxopropanoic acid; |
| 63 | 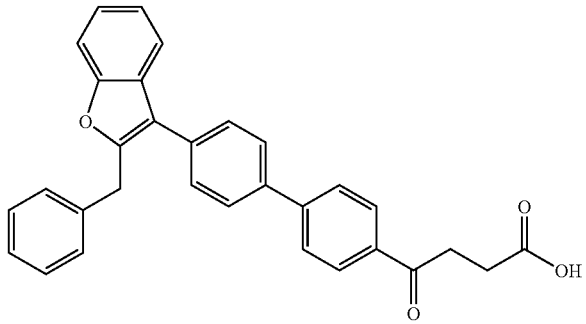<br>4-[4'-(2-benzyl-1-benzofuran-3-yl)biphenyl-4-yl]-4-oxobutanoic acid; |
| 64 | ({benzyl[4'-(1H-indol-1-yl)biphenyl-4-yl]amino}sulfonyl)acetic acid; |
| 65 | 3-({[4'-(1H-indol-1-yl)-3-nitrobiphenyl-4-yl]amino}sulfonyl)benzoic acid; |
| 66 | 4-{[4'-[(2-butyl-1-benzofuran-3-yl)methyl]-4-(3-phenylpropoxy)biphenyl-3-yl]amino}-4-oxobutanoic acid; |

| Ex. No. | Structure and/or Name |
|---|---|
| 67 | 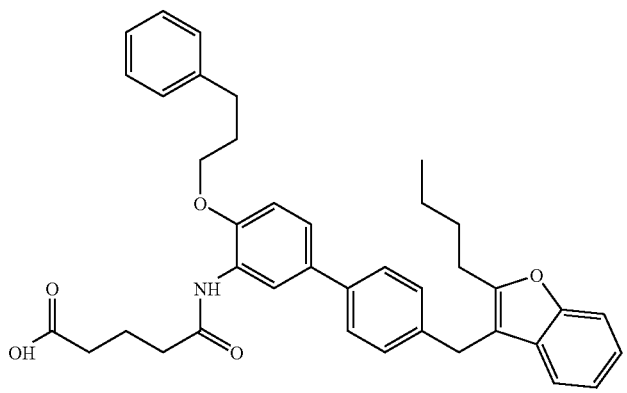<br>5-{[4'-[(2-butyl-1-benzofuran-3-yl)methyl]-4-(3-phenylpropoxy)biphenyl-3-yl]amino}-5-oxopentanoic acid; |
| 68 | 4-({[4'-(1H-indol-1-yl)-3-nitrobiphenyl-4-yl]amino}sulfonyl)benzoic acid; |
| 69 | 3-({4-(benzyloxy)-4'-[(2-butyl-1-benzofuran-3-yl)methyl]biphenyl-3-yl}amino)-3-oxopropanoic acid; |
| 70 | 4-({3-(benzyloxy)-4'-[(2-butyl-1-benzofuran-3-yl)methyl]biphenyl-4-yl}amino)-4-oxobutanoic acid; |
| 71 | 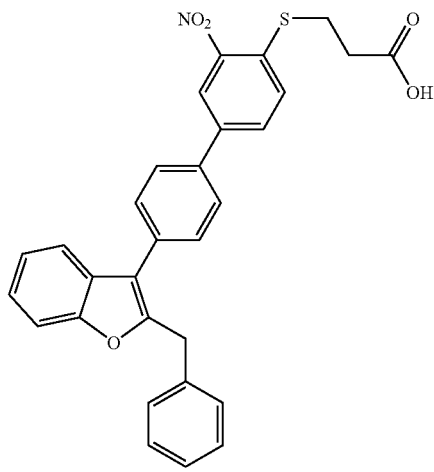<br>3-{[4'-(2-benzyl-1-benzofuran-3-yl)-3-nitrobiphenyl-4-yl]thio}propanoic acid; |
| 72 | N-{[4'-(2-benzyl-1-benzofuran-3-yl)-3-fluorobiphenyl-4-yl]sulfonyl}-N-methylglycine; |
| 73 | 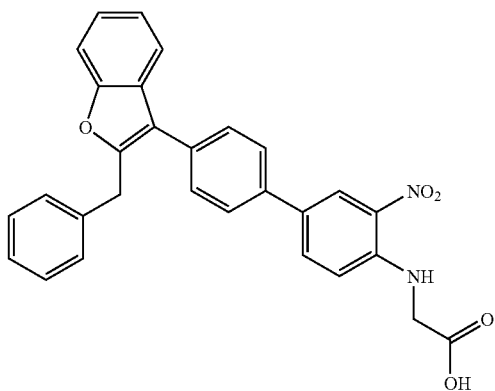<br>N-[4'-(2-benzyl-1-benzofuran-3-yl)-3-nitrobiphenyl-4-yl]glycine; |
| 74 | 2-[4'-(2-Benzyl-benzofuran-3-yl)-3-nitro-biphenyl-4-ylamino]-3-phenyl-propionic acid; |

| Ex. No. | Structure and/or Name |
|---|---|
| 75 | 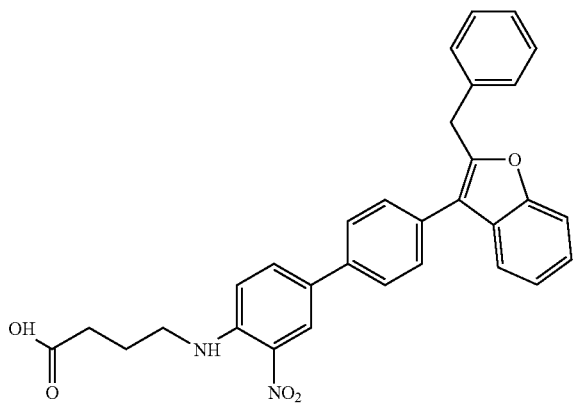
4-{[4'-(2-benzyl-1-benzofuran-3-yl)-3-nitrobiphenyl-4-yl]amino}butanoic acid; |
| 76 | 6-{[4'-(2-benzyl-1-benzofuran-3-yl)-3-nitrobiphenyl-4-yl]amino}hexanoic acid; |
| 77 | 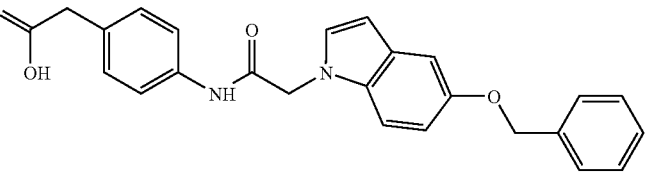
[4-({[5-(benzyloxy)-1H-indol-1-yl]acetyl}amino)phenyl]acetic acid; |
| 78 | N-{[4'-(2-benzyl-1-benzofuran-3-yl)biphenyl-4-yl]sulfonyl}-N-(3-nitrobenzyl)glycine; |
| 79 | 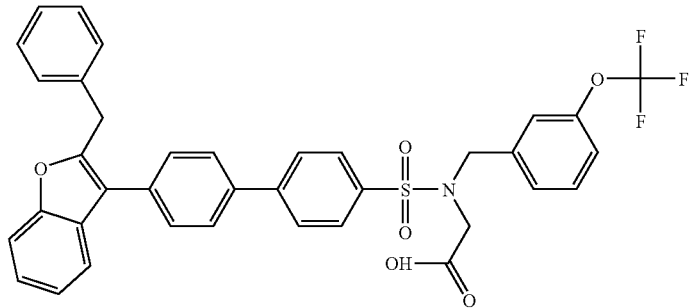
N-{[4'-(2-benzyl-1-benzofuran-3-yl)biphenyl-4-yl]sulfonyl}-N-[3-(trifluoromethoxy)benzyl]glycine; |
| 80 | N-{[4'-(2-benzyl-1-benzofuran-3-yl)biphenyl-4-yl]sulfonyl}-N-(3-methoxybenzyl)glycine; |
| 81 | 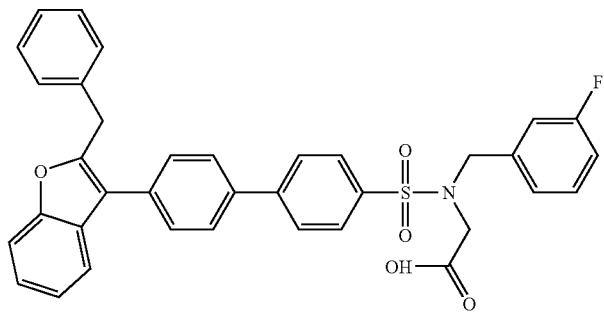
N-{[4'-(2-benzyl-1-benzofuran-3-yl)biphenyl-4-yl]sulfonyl}-N-(3-fluorobenzyl)glycine; |
| 82 | N-{[4'-(2-benzyl-1-benzofuran-3-yl)biphenyl-4-yl]sulfonyl}-N-[3-(trifluoromethyl)benzyl]glycine; |

| Ex. No. | Structure and/or Name |
|---|---|
| 83 | 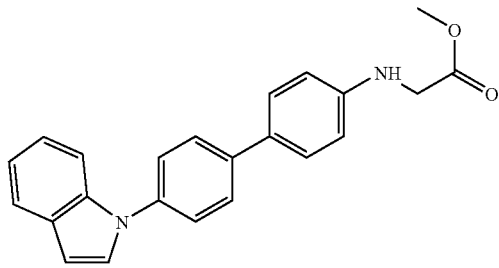<br>methyl N-[4'-(1H-indol-1-yl)biphenyl-4-yl]glycinate; |
| 84 | N-[4'-(1H-indol-1-yl)biphenyl-4-yl]-N-(phenylsulfonyl)glycine; |
| 85 | 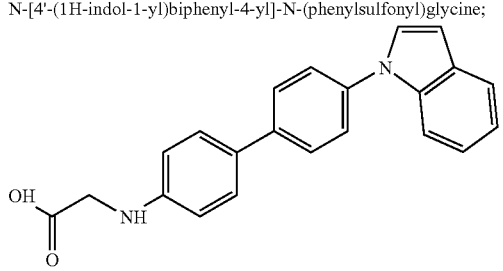<br>N-[4'-(1H-indol-1-yl)biphenyl-4-yl]glycine; |
| 86 | methyl {(4'-(1-butylindolizin-2-yl)biphenyl-4-yl]oxy}acetate; |
| 87 | 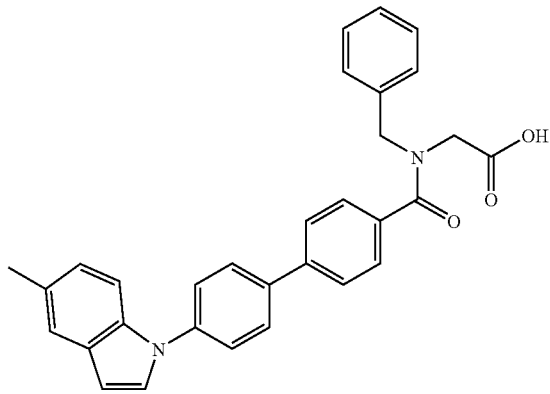<br>N-benzyl-N-{(4'-(5-methyl-1H-indol-1-yl)biphenyl-4-yl]carbonyl}glycine; |
| 88 | N-{[4'-(1H-indol-1-yl)biphenyl-4-yl]carbonyl}-L-phenylalanine; |
| 89 | 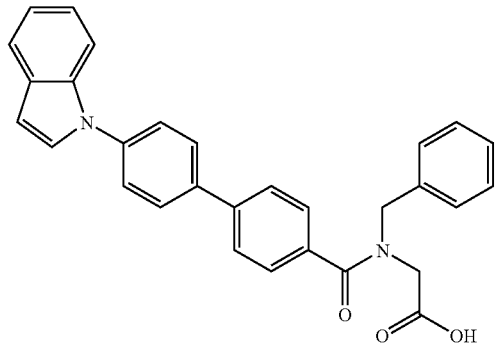<br>N-benzyl-N-{[4'-(1H-indol-1-yl)biphenyl-4-yl]carbonyl}glycine; |
| 90 | ({benzyl[4-(9H-carbazol-9-yl)phenyl]amino}sulfonyl)acetic acid; |

| Ex. No. | Structure and/or Name |
|---|---|
| 91 | 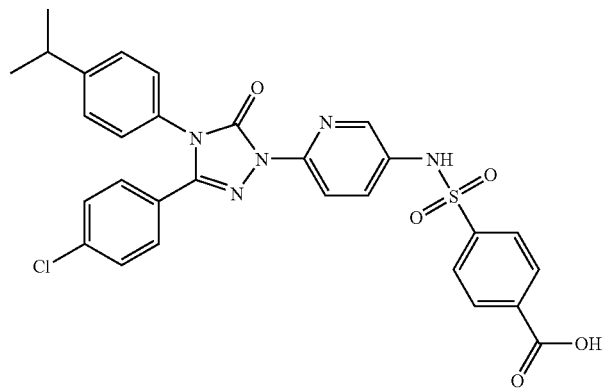 |
| | 4-[({6-[3-(4-chlorophenyl)-4-(4-isopropylphenyl)-5-oxo-4,5-dihydro-1H-1,2,4-triazol-1-yl]pyridin-3-yl}amino)sulfonyl]benzoic acid; |
| 92 | 3-[({6-[3-(4-chlorophenyl)-4-(4-isopropylphenyl)-5-oxo-4,5-dihydro-1H-1,2,4-triazol-1-yl]pyridin-3-yl}amino)sulfonyl]benzoic acid; |
| 93 | [(4-Propyl-[1,1'; 4',1'']terphenyl-4''-sulfonyl)-(3-trifluoromethyl-benzyl)-amino]-acetic acid; |
| 94 | tert-butyl N-{[4-({[4-(4-chlorophenyl)-5-(4-ethylphenyl)-1,3-thiazol-2-yl]amino}carbonyl)phenyl]sulfonyl}-N-(2H-tetrazol-5-ylmethyl)glycinate; and |
| 95 | N-[(4'-dibenzo[b,d]furan-4-ylbiphenyl-4-yl)sulfonyl]-N-[3-(trifluoromethyl)benzyl]glycine. |
| 96 | 4-{[4'-(1-butylindolizin-2-yl)biphenyl-4-yl]oxy}butanoic acid |
| 97 | 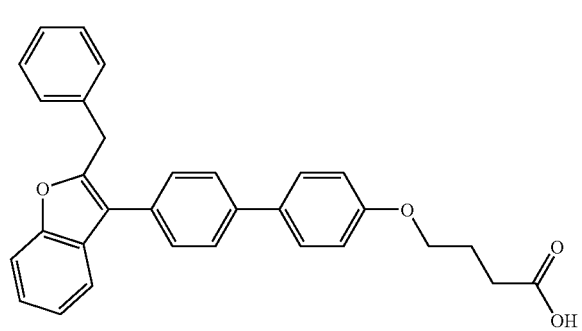 |
| | 4-{[4'-(2-benzyl-1-benzofuran-3-yl)biphenyl-4-yl]oxy}butanoic acid |
| 98 | 3-{[4'-[(2-butyl-1-benzofuran-3-yl)methyl]-4-(3-phenylpropoxy)biphenyl-3-yl]amino}-3-oxopropanoic acid |
| 99 | ({benzyl[4'-(1H-indol-1-yl)biphenyl-4-yl]amino}sulfonyl)acetic acid |
| 100 | N-[(4'-dibenzo[b,d]furan-4-ylbiphenyl-4-yl)sulfonyl]-N-[3-(trifluoromethyl)benzyl]glycine |
| 101 | 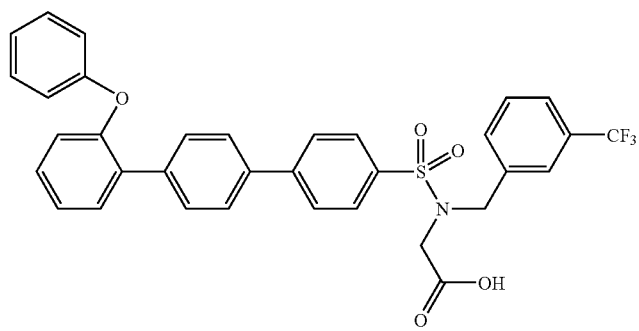 |
| | [(2-Phenoxy-[1,1'; 4',1'']terphenyl-4''-sulfonyl)-(3-trifluoromethyl-benzyl)-amino]-acetic acid |
| 102 | [(4-Propyl-[1,1'; 4', 1'']terphenyl-4''-sulfonyl)-(3-trifluoromethyl-benzyl)-amino]-acetic acid |

| Ex. No. | Structure and/or Name |
|---|---|
| 103 | 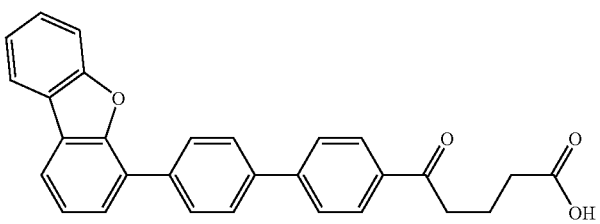<br>5-(4'-Dibenzofuran-4-yl-biphenyl-4-yl)-5-oxo-pentanoic acid |
| 104 | [(4'-Dibenzofuran-4-yl-biphenyl-4-sulfonyl)-(3-fluoro-benzyl)-amino]-acetic acid |
| 105 | 2-(4'-Dibenzofuran-4-yl-3-nitro-biphenyl-4-ylamino)-3-phenyl-propionic acid |
| 106 | 3-(3-Cyano-4'-dibenzofuran-4-yl-biphenyl-4-ylamino)-propionic acid |
| 107 | 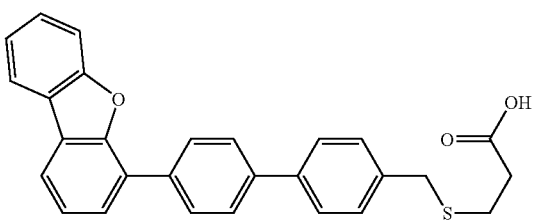<br>3-(4'-Dibenzofuran-4-yl-biphenyl-4-ylmethylsulfanyl)-propionic acid |
| 108 | 3-(4'-Dibenzofuran-4-yl-biphenyl-4-ylmethylsulfanyl)-2,2-dimethyl-propionic acid |
| 109 | 3-(4'-Dibenzofuran-4-yl-biphenyl-4-ylmethylsulfanyl)-2-methyl-propionic acid |
| 110 | 2-(4'-Dibenzofuran-4-yl-biphenyl-4-ylmethylsulfanyl)-3-methyl-butyric acid |
| 111 | 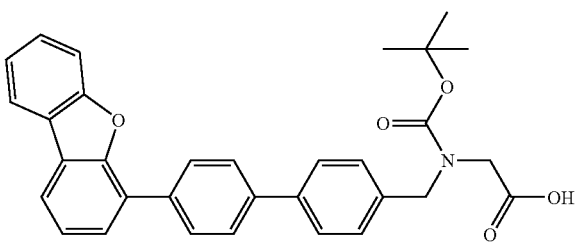<br>[tert-Butoxycarbonyl-(4'-dibenzofuran-4-yl-biphenyl-4-ylmethyl)-amino]-acetic acid |
| 112 | 3-{[(4'-dibenzo[b,d]furan-4-ylbiphenyl-4-yl)methyl]thio}propanoic acid |

BIOLOGY EXAMPLES

Example 1

Method for Measuring PTP-1B Activity

The test compounds are evaluated for their in vitro inhibitory activity against recombinant human PTP1B with phosphotyrosyl dodecapeptide TRDI(P)YETD(P)Y(P)YRK. This corresponds to the 1142-1153 insulin receptor kinase regulatory domain, phosphorylated on the 1146, 1150 and 1151 tyrosine residues; IR-triphosphopeptide as a source of substrate. Enzyme reaction progression is monitored via the release of inorganic phosphate as detected by the malachite green-ammonium molybdate method for the phosphopeptide.

Preferred compounds of the invention exhibit $IC_{50}$ values of less than 10 µM; more preferred compounds of the invention exhibit $IC_{50}$ values of less than 1 µM. Particularly preferred compounds exhibit $IC_{50}$ values of less than 300 nM.

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

What is claimed is:

1. A compound of the formula:

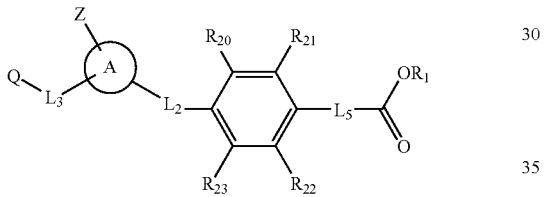

or a pharmaceutically acceptable salt thereof, wherein, $R_1$ is H, $C_1$-$C_6$ alkyl, phenyl($C_1$-$C_6$)alkyl, or $C_2$-$C_6$ alkenyl;

$L_2$ is a bond;

$L_3$ is a bond, —($C_1$-$C_4$)alkyl-O—, —O—($C_1$-$C_4$)alkyl, —($C_1$-$C_4$) alkyl-, -alkenyl-, or -phenyl-;

$L_5$ is —N($R_9$)C(O)—($C_1$-$C_4$) alkyl- or —N($R_9$)SO$_2$—($C_1$-$C_4$)alkyl-, wherein $R_9$ is H, $C_1$-$C_6$ alkyl, $C_1$-$C_6$ alkoxycarbonyl, —SO$_2$-aryl, heteroarylalkyl, or arylalkyl, wherein the aryl or heteroaryl groups are optionally substituted with 1, 2, 3, or 4 groups that are independently $C_1$-$C_4$ alkyl, $C_1$-$C_4$ alkoxy, halogen, OH, NO$_2$, NH$_2$, NH($C_1$-$C_6$) alkyl, N($C_1$-$C_6$)alkyl($C_1$-$C_6$)alkyl, haloalkyl, or haloalkoxy;

$R_{20}$, $R_{21}$, $R_{22}$, and $R_{23}$ are independently selected from H, arylalkoxy, arylalkyl, halogen, alkyl, alkoxy, NO$_2$, NH$_2$, CN, NH($C_1$-$C_6$)alkyl, N($C_1$-$C_6$)alkyl ($C_1$-$C_6$)alkyl, NH-aryl, NHC(O)—($C_1$-$C_4$) alkyl-aryl, N($C_1$-$C_4$ alkyl)C(O)—($C_1$-$C_4$) alkyl-aryl, N($C_1$-$C_4$)alkyl-aryl, —NHSO$_2$-aryl, and —N($C_1$-$C_4$alkyl)SO$_2$-aryl, wherein the aryl group is optionally substituted with 1, 2, 3, 4, or 5 groups that are independently $C_1$-$C_6$ alkyl, $C_1$-$C_6$ alkoxy, halogen, OH, NO$_2$, haloalkyl, or haloalkoxy;

the A ring is phenyl, which is optionally substituted with 1, 2, or 3 groups that are independently, halogen, $C_1$-$C_6$ alkyl, $C_1$-$C_6$ alkoxy, $C_1$-$C_4$ haloalkyl, $C_1$-$C_4$ haloalkoxy, NO$_2$, NH$_2$, NH($C_1$-$C_6$)alkyl, or N($C_1$-$C_6$)alkyl($C_1$-$C_6$) alkyl;

Q is aryl, aryl-carbonyl-aryl, -aryl-O-aryl, -aryl-alkyl-aryl, -aryl-heteroaryl, -aryl-heterocycloalkyl, heteroaryl, or -heteroaryl-alkyl-aryl, wherein the aforementioned cyclic groups are optionally substituted with 1, 2, 3, 4, or 5 groups that are independently alkoxycarbonyl, $C_1$-$C_6$ alkyl, $C_1$-$C_6$ alkoxy, halogen, haloalkyl, haloalkoxy, NR$_6$R$_7$, phenyl, phenyl-$C_1$-$C_6$ alkyl-, or phenyloxy-; wherein $R_6$ and $R_7$ are independently H, $C_1$-$C_6$ alkyl, aryl($C_1$-$C_6$) alkyl, $C_2$-$C_6$ alkanoyl, aryl $C_2$-$C_6$ alkanoyl, $C_1$-$C_6$ alkoxycarbonyl, aryl $C_1$-$C_6$ alkoxycarbonyl, heteroarylcarbonyl, heteroaryl, heterocycloalkylcarbonyl, —C(O)NH$_2$, —C(O)NH($C_1$-$C_6$)alkyl, —C(O)N($C_1$-$C_6$)alkyl ($C_1$-$C_6$)alkyl, or —SO$_2$-aryl, wherein the cyclic groups are optionally substituted with 1, 2, 3, or 4 groups that are independently halogen, $C_1$-$C_4$ alkyl, $C_1$-$C_4$ alkoxy, NO$_2$, OH, NH$_2$, NH($C_1$-$C_6$)alkyl, N($C_1$-$C_6$)alkyl($C_1$-$C_6$)alkyl, haloalkyl or haloalkoxy; and Z is absent, H, —NHC(O)aryl, —N($C_1$-$C_4$ alkyl)C(O)aryl, or aryl, wherein the aryl groups are optionally substituted with 1, 2, 3, 4, or 5 groups that are independently $C_1$-$C_6$ alkyl, $C_1$-$C_6$ alkoxy, halogen, haloalkyl, haloalkoxy, or NO$_2$, or Z is —NHC(O)—($C_1$-$C_4$)alkyl-($C_3$-$C_7$)cycloalkyl, or —N($C_1$-$C_4$)alkyl-C(O)—($C_1$-$C_4$)alkyl-($C_3$-$C_7$)cycloalkyl.

2. A compound according to claim 1, wherein

Q is phenyl, phenyl-O-phenyl, -phenyl-carbonyl-phenyl, phenyl-($C_1$-$C_4$)alkyl-phenyl, phenyl-pyridyl, -phenyl-pyrimidyl, -phenyl-benzoturanyl, phenylindolyl, -phenyl-piperidinyl, -phenyl-pyrrolidinyl, -phenyl-piperazinyl, indolizinyl, benzofuranyl, indolyl, dibenzofuranyl, -benzothienyl-($C_1$-$C_4$)alkyl-phenyl, -indolyl-($C_1$-$C_4$) alkyl-phenyl, benzofuranyl-($C_1$-$C_4$) alkyl-phenyl, or imidazo[2,1-b]thiazol-3-one, wherein the aforementioned cyclic groups are optionally substituted with 1, 2, 3, 4, or 5 groups that are independently alkoxycarbonyl, $C_1$-$C_6$ alkyl, $C_1$-$C_6$ alkoxy, halogen, haloalkyl, haloalkoxy, NR$_6$ R$_7$, phenyl, or phenyl-($C_1$-$C_6$)alkyl-; wherein $R_6$ and $R_7$ are independently H, $C_1$-$C_6$ alkyl, phenyl($C_1$-$C_6$)alkyl, $C_2$-$C_6$ alkanoyl, phenyl($C_2$-$C_6$)alkanoyl, $C_1$-$C_6$ alkoxycarbonyl, phenyl($C_1$-$C_6$)alkoxycarbonyl, heteroarylcarbonyl, heteroaryl, heterocycloalkylcarbonyl, —C(O)NH$_2$, —C(O)NH($C_1$-$C_6$)alkyl, —C(O)N($C_1$-$C_6$)alkyl($C_1$-$C_6$)alkyl, or —SO$_2$-aryl, wherein the cyclic groups are optionally substituted with 1, 2, 3, or 4 groups that are independently halogen, $C_1$-$C_4$ alkyl, $C_1$-$C_4$ alkoxy, NO$_2$, OH, NH$_2$, NH($C_1$-$C_6$)alkyl, N($C_1$-$C_6$)alkyl($C_1$-$C_6$)alkyl, haloalkyl or haloalkoxy; and Z is absent, H, or phenyl, wherein the phenyl group is optionally substituted with 1, 2, 3, 4, or 5 groups that are independently $C_1$-$C_6$ alkyl, $C_1$-$C_6$ alkoxy, halogen, $C_1$-$C_4$ haloalkyl, $C_1$-$C_4$ haloalkoxy, or NO$_2$.

3. A compound according to claim 2, wherein the A ring is phenyl, which is optionally substituted with 1, 2, or 3 groups that are independently, halogen, $C_1$-$C_6$ alkyl, $C_1$-$C_6$ alkoxy, $C_1$-$C_4$ haloalkyl, $C_1$-$C_4$ haloalkoxy, NO$_2$, NH$_2$, NH($C_1$-$C_6$)alkyl, or N($C_1$-$C_6$)alkyl($C_1$-$C_6$)alkyl; and $R_{20}$, $R_{21}$, $R_{22}$, and $R_{23}$ are independently selected from H, phenyl($C_1$-$C_5$)alkoxy, phenyl($C_1$-$C_6$)alkyl, halogen, ($C_1$-$C_6$)alkyl, alkoxy, NO$_2$, NH$_2$, NH($C_1$-$C_6$)alkyl, N($C_1$-$C_6$)alkyl($C_1$-$C_6$)alkyl, NH-phenyl, NHC(O)—($C_1$-$C_4$) alkyl- phenyl, N($C_1$-$C_4$ alkyl)C(O)—($C_1$-$C_4$) alkyl- phenyl, N($C_1$-$C_4$)alkyl-phenyl, —NHSO$_2$-phenyl, and —N($C_1$-$C_4$ alkyl)SO$_2$-phenyl, wherein the phenyl group is optionally substituted with 1, 2, 3, 4, or 5 groups that are independently $C_1$-$C_6$ alkyl, $C_1$-$C_6$ alkoxy, halogen, OH, NO$_2$, $C_1$-$C_4$ haloalkyl, $C_1$-$C_4$ haloalkoxy.

4. A compound according to claim 3, wherein $R_1$ is H, $C_1$-$C_6$ alkyl, benzyl, or allyl;

$L_3$ is a bond, —($C_1$-$C_4$)alkyl-O—, —O—($C_1$-$C_4$)alkyl, —($C_1$-$C_4$) alkyl-, -alkenyl-, or -phenyl-;

$L_5$ is —N($R_9$)C(O)—($C_1$-$C_4$) alkyl- or —N($R_9$)SO$_2$—($C_1$-$C_4$)alkyl-, wherein $R_9$ independently is H, $C_1$-$C_6$ alkyl, —SO$_2$-phenyl, —$C_1$-$C_6$ alkyl-furanyl, —$C_1$-$C_6$- alkyl-tetrazolyl, —$C_1$-$C_6$- alkyl thienyl, —$C_1$-$C_6$- alkyl pyrrolyl, —$C_1$-$C_6$- alkyl pyridyl, or benzyl, wherein the aryl and heteroaryl groups are optionally substituted with 1, 2, 3, or 4 groups that are independently $C_1$-$C_4$ alkyl, $C_1$-$C_4$ alkoxy, halogen, OH, NO$_2$, NH$_2$, NH($C_1$-$C_6$)alkyl, N($C_1$-$C_6$)alkyl($C_1$-$C_6$)alkyl, $C_1$-$C_4$ haloalkyl, or $C_1$-$C_4$ haloalkoxy.

5. A compound according to claim 1, wherein the A ring is phenyl, which is optionally substituted with 1, 2, or 3 groups that are independently, halogen, $C_1$-$C_6$ alkyl, $C_1$-$C_6$ alkoxy, $C_1$-$C_2$ haloalkyl, $C_1$-$C_2$ haloalkoxy, NO$_2$, NH$_2$, NH($C_1$-$C_6$)alkyl, or N($C_1$-$C_6$)alkyl($C_1$-$C_2$) alkyl;

Z is phenyl, optionally substituted with 1, 2, 3, 4, or 5 groups that are independently $C_1$-$C_6$ alkyl, $C_1$-$C_6$ alkoxy, halogen, $C_1$-$C_4$ haloalkyl, $C_1$-$C_4$ haloalkoxy, or NO$_2$.

6. A compound according to claim 1, wherein $R_{22}$ and $R_{23}$ are both H;

$L_5$ is —N($R_9$)SO$_2$—($C_1$-$C_4$)alkyl-; and

Q is phenyl, -phenyl-O-phenyl, indolizinyl, benzofuranyl, indolyl, dibenzofuranyl, -benzothienyl-($C_1$-$C_4$) alkyl-phenyl, -indolyl-($C_1$-$C_4$)alkyl-phenyl, or benzofuranyl-($C_1$-$C_4$) alkyl-phenyl, wherein the aforementioned cyclic groups are optionally substituted with 1, 2, 3, 4, or 5 groups that are independently alkoxycarbonyl, $C_1$-$C_6$ alkyl, $C_1$-$C_6$ alkoxy, halogen, haloalkyl, haloalkoxy, NR$_6$R$_7$, phenyl, or phenyl-($C_1$-$C_6$)alkyl-.

7. A compound according to claim 1, wherein $R_9$ is H, $C_1$-$C_6$ alkyl, —SO$_2$-phenyl, —$C_1$-$C_6$ alkyl-furanyl, —$C_1$-$C_6$ alkyl-tetrazolyl, —$C_1$-$C_6$- alkyl thienyl, —$C_1$-$C_6$- alkyl pyrrolyl, —$C_1$-$C_6$- alkyl pyridyl, or benzyl, wherein the aryl and heteroaryl groups are optionally substituted with 1, 2, 3, or 4 groups that are independently $C_1$-$C_4$ alkyl, $C_1$-$C_4$ alkoxy, halogen, OH, NO$_2$, NH$_2$, NH($C_1$-$C_6$)alkyl, N($C_1$-$C_6$)alkyl($C_1$-$C_6$) alkyl, $C_1$-$C_2$ haloalkyl, or $C_1$-$C_4$ haloalkoxy; and $L_3$ is a bond, —($C_1$-$C_4$)alkyl-O—, —O—($C_1$-$C_4$)alkyl, —($C_1$-$C_4$)alkyl-, -alkenyl-, or -phenyl-.

8. A compound according to claim 1, wherein the A ring is phenyl, which is optionally substituted with 1, 2, or 3 groups that are independently, halogen, $C_1$-$C_6$ alkyl, $C_1$-$C_6$ alkoxy, $C_1$-$C_2$ haloalkyl, $C_1$-$C_2$ haloalkoxy, NO$_2$, NH$_2$, NH($C_1$-$C_6$)alkyl, or N($C_1$-$C_6$)alkyl($C_1$-$C_6$) alkyl;

Q is phenyl, -phenyl-O-phenyl, benzofuranyl, indolyl, dibenzofuranyl, or benzofuranyl-CH$_2$-phenyl, wherein the aforementioned cyclic groups are optionally substituted with 1, 2, 3, 4, or 5 groups that are independently $C_1$-$C_6$ alkoxycarbonyl, $C_1$-$C_6$ alkyl, $C_1$-$C_6$ alkoxy, halogen, CF$_3$, OCF$_3$, NR$_6$R$_7$, phenyl, or phenyl-($C_1$-$C_6$) alkyl-; wherein $R_6$ and $R_7$ are independently H, $C_1$-$C_6$ alkyl, benzyl, $C_2$-$C_6$ alkanoyl, phenyl($C_1$-$C_6$)alkanoyl, $C_1$-$C_6$ alkoxycarbonyl, or —SO$_2$-phenyl, wherein the cyclic groups are optionally substituted with 1, 2, 3, or 4 groups that are independently halogen, $C_1$-$C_4$ alkyl, $C_1$-$C_4$ alkoxy, NO$_2$, OH, NH$_2$, NH($C_1$-$C_6$)alkyl, N($C_1$-$C_6$)alkyl($C_1$-$C_6$)alkyl, CF$_3$, or OCF$_3$; and Z is phenyl, optionally substituted with 1, 2, or 3 groups that are independently $C_1$-$C_6$ alkyl, $C_1$-$C_6$ alkoxy, halogen, CF$_3$, OCF$_3$, or NO$_2$.

9. A compound according to claim 1, wherein $L_3$ is a bond, —($C_1$-$C_4$)alkyl-O—, —O—($C_1$-$C_4$)alkyl, or —($C_1$-$C_4$)alkyl-;

$L_5$ is —N($R_9$)SO$_2$—($C_1$-$C_4$)alkyl-;

$R_1$ is H or $C_1$-$C_6$ alkyl;

$R_{21}$ is H; and $R_{22}$ is H, phenyl($C_1$-$C_6$)alkoxy, benzyl, halogen, ($C_1$-$C_6$) alkyl, $C_1$-$C_6$ alkoxy, NO$_2$, NH$_2$, NH($C_1$-$C_6$)alkyl, or N($C_1$-$C_6$)alkyl($C_1$-$C_6$)alkyl, wherein the phenyl group is optionally substituted with 1, 2, 3, 4, or 5 groups that are independently $C_1$-$C_6$alkyl, $C_1$-$C_6$ alkoxy, halogen, OH, NO$_2$, CF$_3$ or OCF$_3$.

10. A compound according to claim 1, wherein the A ring is phenyl, which is optionally substituted with 1, or 2 groups that are independently, halogen, $C_1$-$C_6$ alkyl, $C_1$-$C_6$ alkoxy, CF$_3$, OCF$_3$, NO$_2$, NH$_2$, NH($C_1$-$C_6$)alkyl, or N($C_1$-$C_6$)alkyl($C_1$-$C_6$)alkyl;

Q is phenyl, -phenyl-O-phenyl, benzofuranyl, dibenzofuranyl, or benzofuranyl-CH$_2$-phenyl, wherein the aforementioned cyclic groups are optionally substituted with 1, 2, or 3 groups that are independently $C_1$-$C_6$ alkoxycarbonyl, $C_1$-$C_6$ alkyl, $C_1$-$C_6$ alkoxy, halogen, CF$_3$, OCF$_3$, NH$_2$, NH($C_1$-$C_6$)alkyl, or N($C_1$-$C_6$)alkyl($C_1$-$C_6$)alkyl.

11. A compound according to claim 4, of the formula:

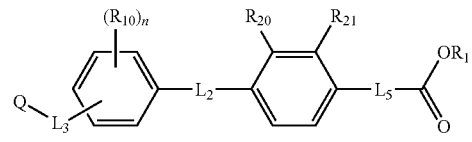

wherein n is 0, 1, 2, or 3;

each $R_{10}$ is independently, halogen, $C_1$-$C_6$ alkyl, $C_1$-$C_6$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl;

$R_1$ is H, $C_1$-$C_6$ alkyl, or benzyl; and

Q is phenyl, -phenyl-O-phenyl, -phenyl-$(C_1$-$C_4)$alkyl-phenyl, -phenyl -pyridyl, -phenyl-pyrimidyl, -phenyl-benzofuranyl, -phenyl-indolyl, -phenyl-piperidinyl, -phenyl-pyrrolidinyl, -phenyl-piperazinyl, indolizinyl, benzofuranyl, indolyl, dibenzofuranyl, -benzothienyl-$(C_1$-$C_4)$ alkyl-phenyl, -indolyl-$(C_1$-$C_4)$alkyl-phenyl, benzofuranyl-$(C_1$-$C_4)$alkyl-phenyl, or imidazo[2,1b]thiazol-3-one, wherein the aforementioned cyclic groups are optionally substituted with 1, 2, 3, 4, or 5 groups that are independently alkoxycarbonyl, $C_1$-$C_6$ alkyl, $C_1$-$C_6$ alkoxy, halogen, haloalkyl, haloalkoxy, $NR_6R_7$, phenyl, or phenyl-$(C_1$-$C_6)$alkyl-.

12. A compound according to claim 11, wherein $L_3$ is a bond, —$(C_1$-$C_4)$alkyl-O—, —O—$(C_1$-$C_4)$alkyl, or —$(C_1$-$C_4)$alkyl-; and $R_{20}$ and $R_{21}$ are independently selected from H, phenyl$(C_1$-$C_6)$alkoxy, phenyl$(C_1$-$C_6)$alkyl, halogen, $(C_1$-$C_6)$alkyl, $C_1$-$C_6$ alkoxy, $NO_2$, $NH_2$, $NH(C_1$-$C_6)$alkyl, and $N(C_1$-$C_6)$alkyl$(C_1$-$C_6)$alkyl, wherein the phenyl group is optionally substituted with 1, 2, 3, 4, or 5 groups that are independently $C_1$-$C_4$ alkyl, $C_1$-$C_6$ alkoxy, halogen, OH, $NO_2$, $C_1$-$C_2$ haloalkyl, or $C_1$-$C_2$ haloalkoxy.

13. A compound according to claim 12, wherein $R_1$ is H, or $C_1$-$C_6$ alkyl, and Q is phenyl, -phenyl-O-phenyl, indolizinyl, benzofuranyl, indolyl, dibenzofuranyl, -benzothienyl-$(C_1$-$C_4)$alkyl-phenyl, -indolyl-$(C_1$-$C_4)$alkyl-phenyl, benzofuranyl-$(C_1$-$C_4)$alkyl-phenyl, or imidazo[2,1-b]thiazol-3-one, wherein the aforementioned cyclic groups are optionally substituted with 1, 2, 3, 4, or 5 groups that are independently alkoxycarbonyl, $C_1$-$C_6$ alkyl, $C_1$-$C_6$ alkoxy, halogen, haloalkyl, haloalkoxy, $NR_6R_7$, phenyl, or phenyl-$(C_1$-$C_6)$alkyl-.

14. A compound according to claim 13 of the formula:

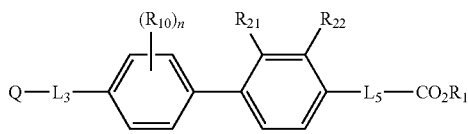

wherein n is 0, 1, 2, or 3;

each $R_{10}$ is independently, halogen, $C_1$-$C_6$ alkyl, $C_1$-$C_6$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl.

15. A compound according to claim 12, wherein $L_3$ is a bond or —$(C_1$-$C_4)$ alkyl-.

16. A compound according to claim 1, wherein $R_1$ and $R_{21}$ are both H; and $R_{22}$ is H, phenyl$(C_1$-$C_6)$alkoxy, benzyl, halogen, $(C_1$-$C_6)$ alkyl, $C_1$-$C_6$ alkoxy, $NO_2$, $NH_2$, $NH(C_1$-$C_6)$alkyl, or $N(C_1$-$C_6)$alkyl$(C_1$-$C_6)$alkyl, wherein the phenyl group is optionally substituted with 1, 2, 3, 4, or 5 groups that are independently $C_1$-$C_6$ alkyl, $C_1$-$C_6$ alkoxy, halogen, OH, $NO_2$, $C_1$-$C_2$ haloalkyl, or $C_1$-$C_2$ haloalkoxy.

17. A compound according to claim 16, wherein $R_9$ is H, $C_1$-$C_6$ alkyl, —$SO_2$-phenyl, —$C_1$-$C_4$ alkyl-furanyl, —$C_1$-$C_4$ alkyl-tetrazolyl, —$C_1$-$C_4$- alkyl thienyl, —$C_1$-$C_4$- alkyl pyrrolyl, —$C_1$-$C_4$- alkyl pyridyl, or benzyl, wherein the aryl and heteroaryl groups are optionally substituted with 1, 2, 3, or 4 groups that are independently $C_1$-$C_4$ alkyl, $C_1$-$C_4$ alkoxy, halogen, OH, $NO_2$, $NH_2$, $NH(C_1$-$C_6)$alkyl, $N(C_1$-$C_6)$alkyl$(C_1$-$C_6)$ alkyl, $CF_3$, or $OCF_3$.

18. A compound according to claim 17, wherein $L_5$ is —$N(R_9)C(O)$—$(C_1$-$C_4)$ alkyl.

19. A compound according to claim 18, wherein $R_9$ is H, $C_1$-$C_6$ alkyl, or benzyl, wherein phenyl group is optionally substituted with 1, 2, 3, or 4 groups that are independently $C_1$-$C_4$ alkyl, $C_1$-$C_4$ alkoxy, halogen, OH, $NO_2$, $NH_2$, $NH(C_1$-$C_6)$alkyl, $N(C_1$-$C_6)$alkyl$(C_1$-$C_6)$ alkyl, $CF_3$, or $OCF_3$.

20. A compound according to claim 18, wherein $R_9$ is H, —$SO_2$-phenyl, —$C_1$-$C_4$ alkyl-furanyl, -$C_1$-$C_4$ alkyl-tetrazolyl, —$C_1$-$C_4$- alkyl thienyl, -$C_1$-$C_4$- alkyl pyrrolyl, or —$C_1$-$C_4$- alkyl pyridyl, wherein the aryl and heteroaryl groups are optionally substituted with 1, 2, 3, or 4 groups that are independently $C_1$-$C_4$ alkyl, $C_1$-$C_4$ alkoxy, halogen, OH, $NO_2$, $NH_2$, $NH(C_1$-$C_6)$alkyl, $N(C_1$-$C_6)$alkyl$(C_1$-$C_6)$alkyl, $CF_3$, or $OCF_3$.

21. A compound according to claim 17, wherein $L_5$ is —$N(R_9)SO_2$—$(C_1$-$C_4)$alkyl-.

22. A compound according to claim 21, wherein $R_9$ is H, $C_1$-$C_6$ alkyl, or benzyl, wherein phenyl group is optionally substituted with 1, 2, 3, or 4 groups that are independently $C_1$-$C_4$ alkyl, $C_1$-$C_4$ alkoxy, halogen, OH, $NO_2$, $NH_2$, $NH(C_1$-$C_6)$alkyl, $N(C_1$-$C_6)$alkyl$(C_1$-$C_6)$alkyl, $CF_3$, or $OCF_3$.

23. A compound according to claim 21, wherein $R_9$ is H, —$SO_2$-phenyl, —$C_1$-$C_4$ alkyl-furanyl, —$C_1$-$C_4$ alkyl-tetrazolyl, —$C_1$-$C_4$- alkyl thienyl, —$C_1$-$C_4$- alkyl pyrrolyl, or —$C_1$-$C_4$- alkyl pyridyl, wherein the aryl and heteroaryl groups are optionally substituted with 1, 2, 3, or 4 groups that are independently $C_1$-$C_4$ alkyl, $C_1$-$C_4$ alkoxy, halogen, OH, $NO_2$, $NH_2$, $NH(C_1$-$C_6)$alkyl, $N(C_1$-$C_6)$alkyl$(C_1$-$C_6)$alkyl, $CF_3$, or $OCF_3$.

24. A pharmaceutical composition comprising a compound of claim 1 and at least one pharmaceutically acceptable solvent, carrier, adjuvant or excipient.

25. A compound according to claim 1 that is selected from the group consisting of ({benzyl [4'-(2benzyl-1-benzofuran-3-yl)biphenyl-4-yl] amino}sulfonyl)acetic acid;

3-({3-(benzyloxy)-4'-[(2-butyl--benzofuran-3-yl)methyl] biphenyl-4-yl}amino)-3-oxopropanoic acid;

({benzyl [4'-(1H-indol-1-yl)biphenyl-4-yl] amino}sulfonyl)acetic acid;

4-({3-(benzyloxy)-4'-[(2-butyl-1-benzofuran-3-yl)methyl]biphenyl-4-yl}amino)-4-oxobutanoic acid;

N-[3-Benzyloxy-4'-(2-butyl-benzofuran-3-ylmethyl)-biphenyl-4-yl]-malonamic acid.

26. A compound of the formula:

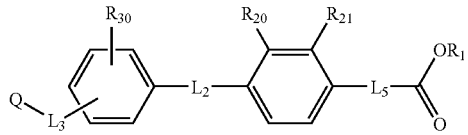

wherein each $R_{30}$ independently represents hydroxy, amino, halogen, $C_1$-$C_6$ alkyl, $C_1$-$C_6$ alkoxy, CF3, amino, or mono- or di$(C_1$-$C_6)$alkylamino;

$L_3$ is a bond, —$(C_1-C_4)$alkyl-O—, —O—$(C_1-C_4)$alkyl, —$(C_1-C_4)$ alkyl-, -alkenyl-, or -phenyl-;

$L_5$ is —$N(R_9)C(O)$—$(C_1-C_4)$ alkyl-, or —$N(R_9)SO_2$—$(C_1-C_4)$alkyl-;

$R_1$ is H, $C_1-C_6$ alkyl, or benzyl;

$R_{20}$ and $R_{21}$ are independently selected from H, arylalkoxy, arylalkyl, halogen, alkyl, alkoxy, $NO_2$, $NH_2$, CN, $NH(C_1-C_6)$alkyl, $N(C_1-C_6)$alkyl$(C_1-C_6)$alkyl, NH-aryl, NHC(O)—$(C_1-C_4)$ alkyl-aryl, $N(C_1-C_4$ alkyl)C(O)—$(C_1-C_4)$ alkyl-aryl, $N(C_1-C_4)$alkyl-aryl, —$NHSO_2$-aryl, and —$N(C_1-C_4$alkyl$)SO_2$-aryl, wherein the aryl group is optionally substituted with 1, 2, 3, 4, or 5 groups that are independently $C_1-C_6$ alkyl, $C_1-C_6$ alkoxy, halogen, OH, $NO_2$, haloalkyl, or haloalkoxy;

Q is phenyl, indolizinyl, benzofuranyl, indolyl, dibenzofuranyl, -benzothienyl-$(C_1-C_4)$alkyl-phenyl, -indolyl-$(C_1-C_4)$alkyl-phenyl, or benzofuranyl-$(C_1-C_4)$alkyl-phenyl, wherein the cyclic portion of each is optionally substituted with 1, 2, 3, 4, or 5 groups that are independently alkoxycarbonyl, $C_1-C_6$ alkyl, $C_1-C_6$ alkoxy, halogen, haloalkyl, haloalkoxy, $NR_6R_7$, or phenyl $R_6$ and $R_7$ are independently H, $C_1-C_6$ alkyl, phenyl$(C_1-C_6)$alkyl, $C_2-C_6$ alkanoyl, $C_1-C_6$ alkoxycarbonyl, phenyl$(C_1-C_6)$alkoxycarbonyl, or —$SO_2$-aryl, wherein each phenyl is optionally substituted with 1, 2, 3, or 4 groups that are independently halogen, $C_1-C_4$ alkyl, $C_1-C_4$ alkoxy, $NO_2$, OH, $NH_2$, $NH(C_1-C_6)$alkyl, $N(C_1-C_6)$alkyl$(C_1-C_6)$alkyl, haloalkyl or haloalkoxy; and $L_2$ is a bond;

where $R_9$ is H, $C_1-C_6$ alkyl, —$SO_2$-phenyl, —$CH_2$-furanyl, —$CH_2$-tetrazolyl, or benzyl, wherein the aromatic portion of each is optionally substituted with 1, 2, 3, or 4 groups that are independently $C_1-C_4$ alkyl, $C_1-C_4$ alkoxy, halogen, OH, $NO_2$, $NH_2$, $NH(C_1-C_5)$alkyl, $N(C_1-C_6)$alkyl$(C_1-C_6)$alkyl, $C_1-C_4$ haloalkyl, or $C_1-C_4$ haloalkoxy.

27. A compound according to claim 26, wherein $L_3$ is a bond, —$(C_1-C_4)$alkyl-O—, —O—$(C_1-C_4)$alkyl, or —$(C_1-C_4)$alkyl-; and $R_{20}$ and $R_{21}$ are independently selected from H, phenyl$(C_1-C_6)$alkoxy, phenyl$(C_1-C_6)$alkyl, halogen, $(C_1-C_6)$alkyl, $C_1-C_6$ alkoxy, $NO_2$, $NH_2$, $NH(C_1-C_6)$alkyl, and $N(C_1-C_6)$alkyl$(C_1-C_6)$alkyl, wherein the phenyl group is optionally substituted with 1, 2, 3, 4, or 5 groups that are independently $C_1-C_6$ alkyl, $C_1-C_6$ alkoxy, halogen, OH, $NO_2$, $C_1-C_2$ haloalkyl, or $C_1-C_2$ haloalkoxy.

28. A compound according to claim 27, wherein $R_1$ is H, or $C_1-C_6$ alkyl,

Q is phenyl, indolizinyl, benzofuranyl, indolyl, or dibenzofuranyl, each of which is optionally substituted with 1, 2, 3, 4, or 5 groups that are independently alkoxycarbonyl, $C_1-C_6$ alkyl, $C_1-C_6$ alkoxy, halogen, haloalkyl, haloalkoxy, $NR_6R_7$, or phenyl.

29. A compound according to claim 28, wherein $L_3$ is a bond or —$C_1-C_4$ alkyl-.

30. A compound of formula:

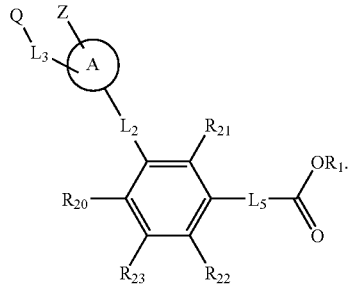

or a pharmaceutically acceptable salt thereof, wherein, $R_1$ is H, $C_1-C_6$ alkyl, phenyl$(C_1-C_6)$alkyl, or $C_1-C_6$ alkenyl;

$L_2$ is a bond;

$L_3$ is —$(C_1-C_4)$alkyl-O—, —O—$(C_1-C_4)$alkyl, —$(C_1-C_4)$ alkyl-, -alkenyl-, or -phenyl-;

$L_5$ is —$N(R_9)C(O)$—$(C_1-C_4)$ alkyl-, or —$N(R_9)SO_2$—$(C_1-C_4)$alkyl-, wherein $R_9$ is H, $C_1-C_6$ alkyl, $C_1-C_6$ alkoxycarbonyl, —$SO_2$-aryl, heteroarylalkyl, or arylalkyl, wherein the aryl or heteroaryl groups are optionally substituted with 1, 2, 3, or 4 groups that are independently $C_1-C_4$ alkyl, $C_1-C_4$ alkoxy, halogen, OH, $NO_2$, $NH_2$, $NH(C_1-C_6)$ alkyl, $N(C_1-C_6)$alkyl$(C_1-C_6)$alkyl, haloalkyl, or haloalkoxy;

$R_{20}$, $R_{21}$, $R_{22}$, and $R_{23}$ are independently selected from H, arylalkoxy, arylalkyl, halogen, alkyl, alkoxy, $NO_2$, $NH_2$, CN, $NH(C_1-C_6)$alkyl, $N(C_1-C_6)$alkyl$(C_1-C_6)$alkyl, NH-aryl, NHC(O)—$(C_1-C_4)$ alkyl-aryl, $N(C_1-C_4$ alkyl)C(O)—$(C_1-C_4)$ alkyl-aryl, $N(C_1-C_4)$alkyl-aryl, —$NHSO_2$-aryl, and —$N(C_1-C_4$alkyl$)SO_2$-aryl, wherein the aryl group is optionally substituted with 1, 2, 3, 4, or 5 groups that are independently $C_1-C_6$ alkyl, $C_1-C_6$ alkoxy, halogen, OH, $NO_2$, haloalkyl, or haloalkoxy;

the A ring is phenyl, which is optionally substituted with 1, 2, or 3 groups that are independently, halogen, $C_1-C_6$ alkyl, $C_1-C_6$ alkoxy, $C_1-C_4$ haloalkyl, $C_1-C_4$ haloalkoxy, $NO_2$, $NH_2$, $NH(C_1-C_6)$alkyl, or $N(C_1-C_6)$alkyl$(C_1-C_6)$alkyl;

Q is aryl, -aryl-carbonyl-aryl, -aryl-O-aryl, -aryl-alkyl-aryl, -aryl-heteroaryl, -aryl-heterocycloalkyl, -heteroaryl, or -heteroaryl-alkyl-aryl, wherein the aforementioned cyclic groups are optionally substituted with 1, 2, 3, 4, or 5 groups that are independently alkoxycarbonyl, $C_1-C_6$ alkyl, $C_1-C_6$ alkoxy, halogen, haloalkyl, haloalkoxy, $NR_6R_7$, phenyl, phenyl-$C_1-C_6$ alkyl-, or phenyloxy-; wherein $R_6$ and $R_7$ are independently H, $C_1-C_6$ alkyl, aryl$(C_1-C_6)$ alkyl, $C_2-C_6$ alkanoyl, aryl $C_2-C_6$ alkanoyl, $C_1-C_6$ alkoxycarbonyl, aryl $C_1-C_6$ alkoxycarbonyl, heteroarylcarbonyl, heteroaryl, heterocycloalkylcarbonyl, —C(O)$N_2$, —C(O)NH$(C_1-C_6)$alkyl, —C(O)N$(C_1-C_6)$alkyl$(C_1-C_6)$alkyl, or —$SO_2$-aryl, wherein the cyclic groups are optionally substituted with 1, 2, 3, or 4 groups that are independently halogen, $C_1-C_4$ alkyl, $C_1-C_4$ alkoxy, $NO_2$, OH, $NH_2$, $NH(C_1-C_6)$alkyl, $N(C_1-C_6)$alkyl$(C_1-C_5)$alkyl, haloalkyl or haloalkoxy; and Z is absent, H, —NHC(O)aryl, —$N(C_1-C_4$ alkyl)C(O)aryl, or aryl, wherein the aryl groups are optionally substituted with 1, 2, 3, 4, or 5 groups that are independently $C_1-C_6$ alkyl, $C_1-C_6$ alkoxy, halogen, haloalkyl, haloalkoxy, or $NO_2$, or Z is —NHC(O)—$(C_1-C_4)$alkyl-$(C_3-C_7)$cycloalkyl, or —N$(C_1-C_4)$alkyl-C(O)—$(C_1-C_4)$alkyl-$(C_3-C_7)$ cycloalkyl.

31. A compound according to claim 30 selected from the group consisting of:

3-{[4'-[(2-butyl-1-benzofuran-3-yl) methyl]-4-(3-phenyl-propoxy)biphenyl-3-yl]amino}-3-oxopropanoic acid;

4-{[4'-[(2-butyl-1-benzofuran-3-yl)methyl]-4-(3-phenyl-propoxy)biphenyl-3-yl]amino}-4-oxobutanoic acid;

5-{[4'-[(2-butyl-1-benzofuran-3-yl)methyl]-4-(3-phenyl-propoxy)biphenyl-3-yl]amino}-5-oxopentanoic acid;

N-[4-Benzyloxy-4'-(2-butyl-benzofuran-3-ylmethyl)-biphenyl-3-yl]-malonamic acid.

32. A compound of the formula:

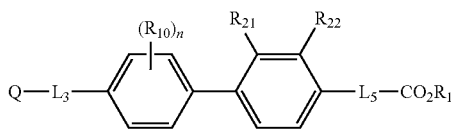

wherein n is 0, 1, 2, or 3;

each $R_{10}$ is independently, halogen, $C_1$-$C_6$ alkyl, $C_1$-$C_6$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl;

$R_1$ is H, $C_1$-$C_6$ alkyl, or benzyl;

$R_{21}$ and $R_{22}$ are independently selected from H, phenyl($C_1$-$C_6$)alkoxy, phenyl($C_1$-$C_6$)alkyl, halogen, ($C_1$-$C_6$)alkyl, $C_1$-$C_6$ alkoxy, $NO_2$, $NH_2$, $NH(C_1$-$C_6)$alkyl, and $N(C_1$-$C_6)$alkyl$(C_1$-$C_6)$alkyl, wherein the phenyl group is optionally substituted with 1, 2, 3, 4, or 5 groups that are independently $C_1$-$C_6$ alkyl, $C_1$-$C_6$ alkoxy, halogen, OH, $NO_2$, $C_1$-$C_2$ haloalkyl, or $C_1$-$C_2$ haloalkoxy;

$L_3$ is a bond or —($C_1$-$C_4$)alkyl-;

$L_5$ is —N($R_9$)C(O)—($C_1$-$C_4$) alkyl- or —N($R_9$)$SO_2$—($C_1$-$C_4$)alkyl-, wherein $R_9$ independently is H, $C_1$-$C_6$ alkyl, —$SO_2$-phenyl, —$C_1$-$C_6$ alkyl-furanyl, —$C_1$-$C_6$ alkyl-tetrazolyl, —$C_1$-$C_6$ alkyl thienyl, —$C_1$-$C_6$- alkyl pyrrolyl, —$C_1$-$C_6$- alkyl pyridyl, or benzyl, wherein the aryl and heteroaryl groups are optionally substituted with 1, 2, 3, or 4 groups that are independently $C_1$-$C_4$ alkyl, $C_1$-$C_4$ alkoxy, halogen, OH, $NO_2$, $NH_2$, $NH(C_1$-$C_6)$alkyl, $N(C_1$-$C_6)$alkyl$(C_1$-$C_6)$alkyl, $C_1$-$C_4$ haloalkyl, or $C_1$-$C_4$ haloalkoxy; and Q is phenyl, phenyl-O-phenyl, indolizinyl, benzofuranyl, indolyl, dibenzofuranyl, -benzothienyl-($C_1$-$C_4$)alkyl-phenyl, -indolyl-($C_1$-$C_4$)alkyl-phenyl, benzofuranyl-($C_1$-$C_4$) alkyl-phenyl, or imidazo[2,1-b]thiazol-3-one, wherein the aforementioned cyclic groups are optionally substituted with 1, 2, 3, 4, or 5 groups that are independently alkoxycarbonyl, $C_1$-$C_6$ alkyl, $C_1$-$C_6$ alkoxy, halogen, haloalkyl, haloalkoxy, $NR_6R_7$, phenyl, or phenyl-($C_1$-$C_6$)alkyl-.

33. A compound according to claim 32 wherein $R_1$ and $R_{21}$ are both H; and $R_{22}$ is H, phenyl($C_1$-$C_6$)alkoxy, benzyl, halogen, ($C_1$-$C_6$) alkyl, $C_1$-$C_6$ alkoxy, $NO_2$, $NH_2$, $NH(C_1$-$C_6)$alkyl, or $N(C_1$-$C_6)$alkyl$(C_1$-$C_6)$alkyl, wherein the phenyl group is optionally substituted with 1, 2, 3, 4, or 5 groups that are independently $C_2$-$C_6$ alkyl, $C_1$-$C_6$ alkoxy, halogen, OH, $NO_2$, $CF_3$, or $OCF_3$.

34. A compound according to claim 33 of the formula:

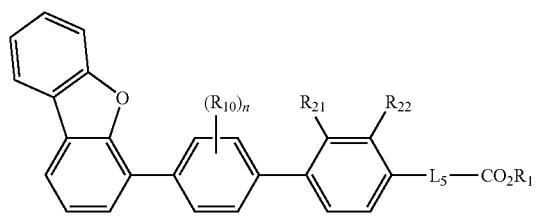

wherein n is 0, 1, 2, or 3; and each $R_{10}$ is independently, halogen, $C_1$-$C_6$ alkyl, $C_1$-$C_6$ alkoxy, $C_1$-$C_4$ haloalkyl, $C_1$-$C_6$ haloalkoxy, $NO_2$, $NH_2$, $NH(C_1$-$C_6)$alkyl, or $N(C_1$-$C_6)$alkyl$(C_1$-$C_6)$alkyl.

35. A compound according to claim 33 of the formula:

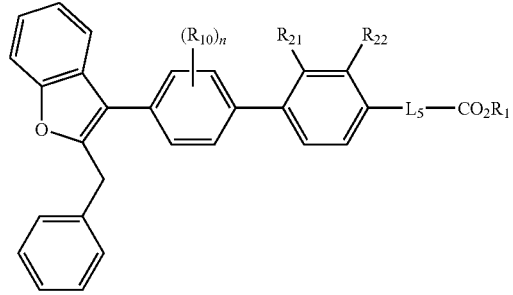

wherein n is 0, 1, 2, or 3; and each $R_{10}$ is independently, halogen, $C_1$-$C_6$ alkyl, $C_1$-$C_6$ alkoxy, $C_1C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl.

36. A compound according to claim 33 of the formula:

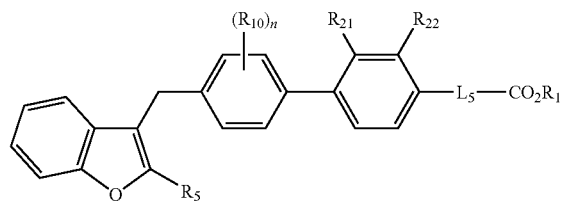

wherein n is 0, 1, 2, or 3;

each $R_{10}$, is independently, halogen, $C_1$-$C_6$ alkyl, $C_1$-$C_6$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl; and $R_5$ is alkoxycarbonyl, $C_1$-$C_6$ alkyl, $C_1$-$C_6$ alkoxy, halogen, $C_1$-$C_4$ haloalkyl, $C_1$-$C_4$ haloalkoxy, $NH_2$, $NH(C_1$-$C_6)$ alkyl, $N(C_1$-$C_6)$alkyl$(C_1$-$C_6)$alkyl, or phenyl.

37. A compound according to claim 33 of the formula:

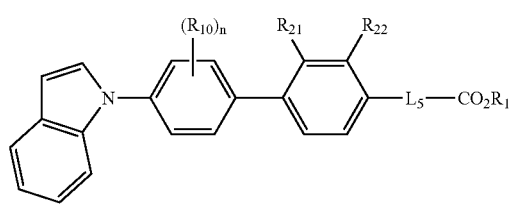

wherein n is 0, 1, 2, or 3; and each $R_{10}$ is independently, halogen, $C_1$-$C_6$ alkyl, $C_1$-$C_6$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl.

38. A compound of the formula:

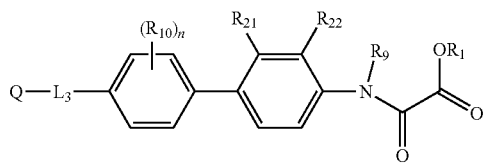

wherein n is 0, 1, 2, or 3;

each $R_{10}$ is independently, halogen, $C_1$-$C_6$ alkyl, $C_1$-$C_6$ alkoxy, $C_1$-$C_4$ haloalkyl, $C_1$-$C_6$ haloalkoxy, $NO_2$, $NH_2$, $NH(C_1$-$C_6)$alkyl, or $N(C_1$-$C_6)$alkyl$(C_1$-$C_6)$alkyl;

$R_1$ is H, $C_1$-$C_6$ alkyl, or benzyl;

$R_{21}$ and $R_{22}$ are independently selected from H, phenyl$(C_1$-$C_6)$alkoxy, phenyl$(C_1$-$C_6)$alkyl, halogen, $(C_1$-$C_6)$alkyl, $C_1$-$C_6$ alkoxy, $NO_2$, $NH_2$, $NH(C_1$-$C_6)$alkyl, and $N(C_1$-$C_6)$alkyl$(C_1$-$C_6)$alkyl, wherein the phenyl group is optionally substituted with 1, 2, 3, 4, or 5 groups that are independently $C_1$-$C_6$ alkyl, $C_1$-$C_6$ alkoxy, halogen, OH, $NO_2$, $C_1$-$C_2$ haloalkyl, or $C_1$-$C_2$ haloalkoxy;

$L_3$ is a bond or —($C_1$-$C_4$)alkyl-;

$R_9$ is H, $C_1$-$C_6$ alkyl, —$SO_2$-phenyl, —$C_1$-$C_6$ alkyl-furanyl, —$C_1$-$C_6$ alkyl-tetrazolyl, —$C_1$-$C_6$- alkyl thienyl, —$C_1$-$C_6$- alkyl pyrrolyl, —$C_1$-$C_6$- alkyl pyridyl, or benzyl, wherein the aryl and heteroaryl groups are optionally substituted with 1, 2, 3, or 4 groups that are independently $C_1$-$C_4$ alkyl, $C_1$-$C_4$ alkoxy, halogen, OH, $NO_2$, $NH_2$, $NH(C_1$-$C_6)$alkyl, $N(C_1$-$C_6)$alkyl$(C_1$-$C_6)$alkyl, $C_1$-$C_6$haloalkyl, or $C_1$-$C_4$ haloalkoxy; and Q is indolizinyl, benzofuranyl, indolyl, dibenzofuranyl, -benzothienyl-$(C_1$-$C_4)$alkyl-phenyl, -indolyl- $(C_1$-$C_4)$ alkyl-phenyl, benzofuranyl-$(C_1$-$C_4)$ alkyl-phenyl, or imidazo[2,1-b]thiazol-3-one, wherein the aforementioned cyclic groups are optionally substituted with 1, 2, 3, 4, or 5 groups that are independently alkoxycarbonyl, $C_1$-$C_6$ alkyl, $C_1$-$C_6$ alkoxy, halogen, haloalkyl, haloalkoxy, phenyl, or phenyl-$(C_1$-$C_6)$alkyl-.

39. A compound according to claim 38 wherein $R_1$ and $R_{21}$ are both H; and $R_{22}$ is H, phenyl$(C_1$-$C_6)$alkoxy, benzyl, halogen, $(C_1$-$C_6)$ alkyl, $C_1$-$C_6$ alkoxy, $NO_2$, $NH_2$, $NH(C_1$-$C_6)$alkyl, or $N(C_1$-$C_6)$alkyl$(C_1$-$C_6)$alkyl, wherein the phenyl group is optionally substituted with 1, 2, 3, 4, or 5 groups that are independently $C_1$-$C_6$ alkyl, $C_1$-$C_6$ alkoxy, halogen, OH, $NO_2$, $CF_3$, or $OCF_3$.

40. A compound according to claim 38 of the formula:

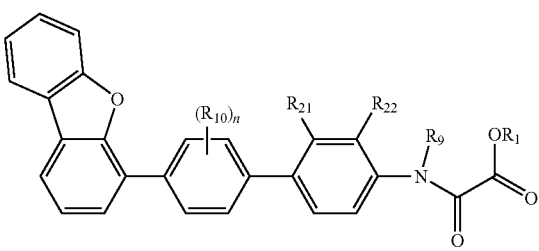

wherein n is 0, 1, 2, 3, or 4; and each $R_{10}$ is independently, halogen, $C_1$-$C_6$ alkyl, $C_1$-$C_6$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl.

41. A compound according to claim 38 of the formula:

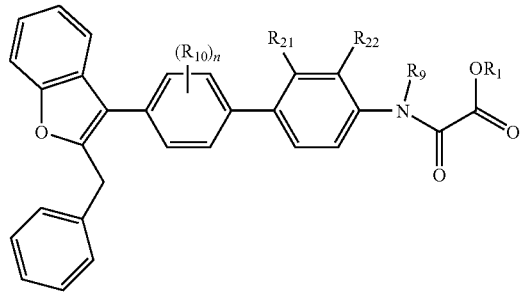

wherein n is 0, 1, 2, or 3; and each $R_{10}$ is independently, halogen, $C_1$-$C_6$ alkyl, $C_1$-$C_6$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl.

42. A compound according to claim 38 of the formula:

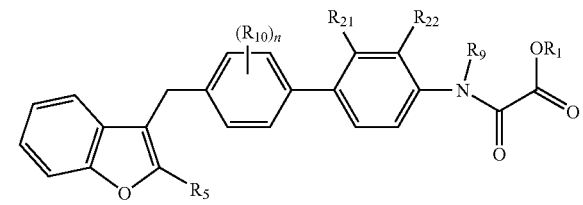

wherein n is 0, 1, 2, or 3;

each $R_{10}$ is independently, halogen, $C_1$-$C_6$ alkyl, $C_1$-$C_6$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl; and $R_5$ is alkoxycarbonyl, $C_1$-$C_6$ alkyl, $C_1$-$C_6$ alkoxy, halogen, $C_1$-$C_4$ haloalkyl, $C_1$-$C_4$ haloalkoxy, $NH_2$, $NH(C_1$-$C_6)$ alkyl, $N(C_1$-$C_6)$alkyl$(C_1$-$C_6)$alkyl, or phenyl.

43. A compound according to claim 38 of the formula:

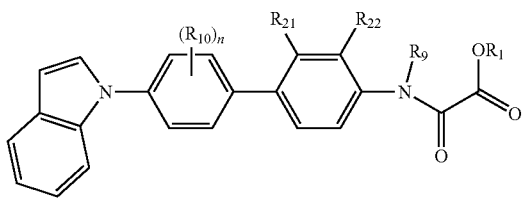

wherein n is 0, 1, 2, or 3; and each $R_{10}$ is independently, halogen, $C_1$-$C_6$ alkyl, $C_1$-$C_6$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$alkyl.

44. A compound according to claim 38 that is N-[3-Benzyloxy4'-(2-butyl-benzofuran-3-ylmethyl)-biphenyl-4-yl]-oxalamic acid

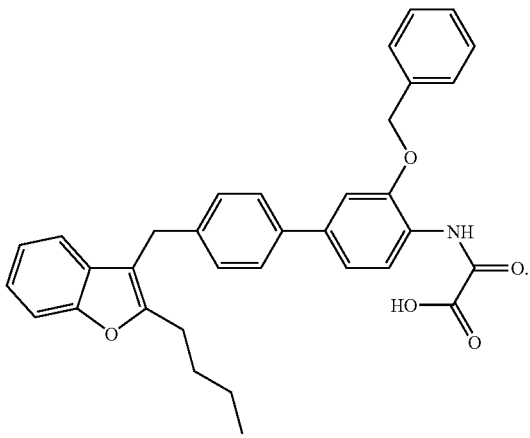

45. A pharmaceutical composition comprising a compound of claim 38 and at least one pharmaceutically acceptable solvent, carrier, adjuvant or excipient.

46. A compound of formula:

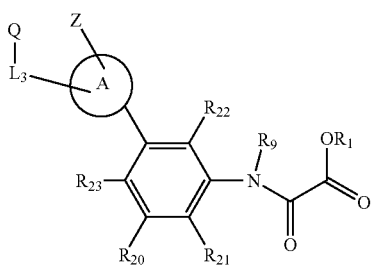

or a pharmaceutically acceptable salt thereof, wherein, $R_1$ is H, $C_1$-$C_6$ alkyl, phenyl($C_1$-$C_6$)alkyl, or $C_2$-$C_6$ alkenyl;

$L_3$ is —($C_1$-$C_4$)alkyl-O—, —O—($C_1$-$C_4$)alkyl, —($C_1$-$C_4$) alkyl-, -alkenyl-, or -phenyl-;

$R_9$ is H, $C_1$-$C_6$ alkyl, $C_1$-$C_6$ alkoxycarbonyl, —$SO_2$-aryl, heteroarylalkyl, or arylalkyl, wherein the aryl or heteroaryl groups are optionally substituted with 1, 2, 3, or 4 groups that are independently $C_1$-$C_4$ alkyl, $C_1$-$C_4$ alkoxy, halogen, OH, $NO_2$, $NH_2$, $NH(C_1$-$C_6)$alkyl, $N(C_1$-$C_6)$alkyl($C_1$-$C_6)$alkyl, haloalkyl, or haloalkoxy;

$R_{20}$, $R_{22}$, and $R_{23}$ are independently selected from H, arylalkoxy, arylalkyl, halogen, alkyl, alkoxy, $NO_2$, $NH_2$, CN, $NH(C_1$-$C_6)$alkyl, $N(C_1$-$C_6)$alkyl($C_1$-$C_6)$alkyl, NH-aryl, NHC(O)—($C_1$-$C_4$) alkyl-aryl, $N(C_1$-$C_4$ alkyl)C (O)—($C_1$-$C_4$) alkyl-aryl, $N(C_1$-$C_4$) alkyl-aryl, —$NHSO_2$-aryl, and —$N(C_1$-$C_4$alkyl)$SO_2$-aryl, wherein the aryl group is optionally substituted with 1, 2, 3, 4, or 5 groups that are independently $C_1$-$C_6$ alkyl, $C_1$-$C_6$alkoxy, halogen, OH, $NO_2$, haloalkyl, or haloalkoxy;

$R_{21}$ is arylalkoxy, wherein the aryl group is optionally substituted with 1, 2, 3, 4, or 5 groups that are independently $C_1$-$C_6$ alkyl, $C_1$-$C_6$ alkoxy, halogen, OH, $NO_2$, haloalkyl, or haloalkoxy;

the A ring is phenyl, which is optionally substituted with 1, 2, or 3 groups that are independently, halogen, $C_1$-$C_6$ alkyl, $C_1$-$C_6$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl($C_1$-$C_6)$ alkyl;

Q is aryl, -aryl-carbonyl-aryl, -aryl-O-aryl, -aryl-alkyl-aryl, -aryl-heteroaryl, -aryl-heterocycloalkyl, -heteroaryl, or -heteroaryl-alkyl-aryl, wherein the aforementioned cyclic groups are optionally substituted with 1, 2, 3, 4, or 5 groups that are independently alkoxycarbonyl, $C_1$-$C_6$alkyl, $C_1$-$C_6$ alkoxy, halogen, haloalkyl, haloalkoxy, $NR_6R_7$, phenyl, phenyl-$C_1$-$C_6$ alkyl-, or phenyloxy-; wherein $R_6$ and $R_7$ are independently H, $C_1$-$C_6$ alkyl, aryl($C_1$-$C_6$) alkyl, $C_2$-$C_6$ alkanoyl, aryl $C_2$-$C_6$ alkanoyl, $C_1$-$C_6$ alkoxycarbonyl, aryl $C_1$-$C_6$ alkoxycarbonyl, heteroarylcarbonyl, heteroaryl, heterocycloalkylcarbonyl, —C(O) $NH_2$, —C(O)NH($C_1$-$C_6)$alkyl, —C(O)N($C_1$-$C_5)$alkyl ($C_1$-$C_6)$alkyl, or —$SO_2$-aryl, wherein the cyclic groups are optionally substituted with 1, 2, 3, or 4 groups that are independently halogen, $C_1$-$C_4$ alkyl, $C_1$-$C_4$ alkoxy, $NO_2$, OH, $NH_2$, $NH(C_1$-$C_6)$alkyl, $N(C_1$-$C_6)$alkyl($C_1$-$C_6)$alkyl, haloalkyl or haloalkoxy; and Z is absent, H, —NHC(O)aryl, —N($C_1$-$C_4$ alkyl)C(O)aryl, or aryl, wherein the aryl groups are optionally substituted with 1, 2, 3, 4, or 5 groups that are independently $C_1$-$C_6$ alkyl, $C_1$-$C_6$ alkoxy, halogen, haloalkyl, haloalkoxy, or $NO_2$, or Z is —NHC(O)—($C_1$-$C_4$)alkyl-($C_3$-$C_7$)cycloalkyl, or —N($C_1$-$C_4$)alkyl-C(O)—($C_1$-$C_4$)alkyl-($C_3$-$C_7$)cycloalkyl.

47. A compound according to 46 that is N-[4'-(2-Butyl-benzofuran-3-ylmethyl)-4-(3phenyl-propoxy)-biphenyl-3-yl]-oxalamic acid

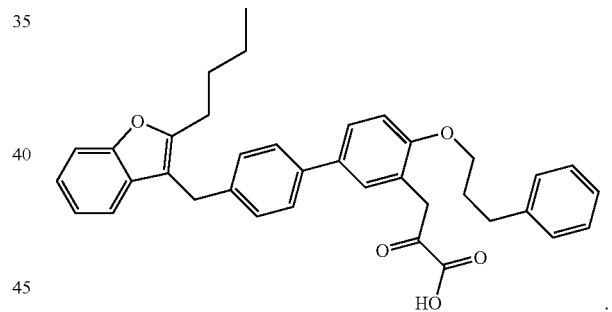

48. A pharmaceutical composition comprising a compound of claim 46 and at least one pharmaceutically acceptable solvent, carrier, adjuvant or excipient.

49. A compound of the formula:

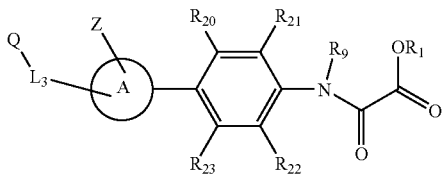

or a pharmaceutically acceptable salt thereof, wherein, $R_1$ is H, $C_1$-$C_6$ alkyl, phenyl($C_1$-$C_6$)alkyl, or $C_2$-$C_6$ alkenyl;

$L_3$ is a bond, —($C_1$-$C_4$)alkyl-O—, —O—($C_1$-$C_4$)alkyl, —($C_1$-$C_4$) alkyl-, -alkenyl-, or -phenyl-;

$R_9$ is H, $C_1$-$C_6$ alkyl, $C_1$-$C_6$ alkoxycarbonyl, —$SO_2$-aryl, heteroarylalkyl, or arylalkyl, wherein the aryl or heteroaryl groups are optionally substituted with 1, 2, 3, or 4 groups that are independently $C_1$-$C_4$ alkyl, $C_1$-$C_4$ alkoxy, halogen, OH, $NO_2$, $NH_2$, $NH(C_1$-$C_6)$alkyl, $N(C_1$-$C_6)$alkyl$(C_1$-$C_6)$alkyl, haloalkyl, or haloalkoxy;

$R_{20}$, $R_{22}$, and $R_{23}$ are independently selected from H, arylalkoxy, arylalkyl, halogen, alkyl, alkoxy, $NO_2$, $NH_2$, CN, $NH(C_1$-$C_6)$alkyl, $N(C_1$-$C_6)$alkyl$(C_1$-$C_6)$alkyl, NH-aryl, NHC(O)—($C_1$-$C_4$) alkyl-aryl, $N(C_1$-$C_4$ alkyl)C(O)—($C_1$-$C_4$) alkyl-aryl, $N(C_1$-$C_4)$alkyl-aryl, —$NHSO_2$-aryl, and —$N(C_1$-$C_4$alkyl)$SO_2$-aryl, wherein the aryl group is optionally substituted with 1, 2, 3, 4, or 5 groups that are independently $C_1$-$C_6$ alkyl, $C_1$-$C_6$ alkoxy, halogen, OH, $NO_2$, haloalkyl, or haloalkoxy;

$R_{21}$, is arylalkoxy, wherein the aryl group is optionally substituted with 1, 2, 3, 4, or 5 groups that are independently $C_1$-$C_6$ alkyl, $C_1$-$C_6$ alkoxy, halogen, OH, $NO_2$, haloalkyl, or haloalkoxy;

the A ring is phenyl, which is optionally substituted with 1, 2, or 3 groups that are independently, halogen, $C_1$-$C_6$ alkyl, $C_1$-$C_6$ alkoxy, $C_1$-$C_4$ haloalkyl, $C_1$-$C_4$ haloalkoxy, $NO_2$, $NH_2$, $NH(C_1$-$C_6)$alkyl, or $N(C_1$-$C_6)$alkyl$(C_1$-$C_6)$ alkyl;

Q is aryl, -aryl-carbonyl-aryl, -aryl-O-aryl, -aryl-alkyl-aryl, -aryl-heteroaryl, -aryl-heterocycloalkyl, -heteroaryl, or -heteroaryl-alkyl-aryl, wherein the aforementioned cyclic groups are optionally substituted with 1, 2, 3, 4, or 5 groups that are independently alkoxycarbonyl, $C_1$-$C_6$ alkyl, $C_1$-$C_6$ alkoxy, halogen, haloalkyl, haloalkoxy, $NR_6R_7$, phenyl, phenyl-$C_1$-$C_6$ alkyl-, or phenyloxy-; wherein $R_6$ and $R_7$ are independently H, $C_1$-$C_6$ alkyl, aryl($C_1$-$C_6$) alkyl, $C_2$-$C_6$ alkanoyl, aryl $C_2$-$C_6$ alkanoyl, $C_1$-$C_6$alkoxycarbonyl, aryl $C_1$-$C_6$ alkoxycarbonyl, heteroarylcarbonyl, heteroaryl, heterocycloalkylcarbonyl, —C(O)$NH_2$, —C(O)NH($C_1$-$C_6$)alkyl, —C(O)N($C_1$-$C_6$)alkyl($C_1$-$C_6$)alkyl, or —$SO_2$-aryl, wherein the cyclic groups are optionally substituted with 1, 2, 3, or 4 groups that are independently halogen, $C_1$-$C_4$ alkyl, $C_1$-$C_4$ alkoxy, $NO_2$, OH, $NH_2$, $NH(C_1$-$C_6)$alkyl, $N(C_1$-$C_6)$alkyl($C_1$-$C_6$)alkyl, haloalkyl or haloalkoxy; and Z is absent, H, —NHC(O)aryl, $N(C_1$-$C_4$ alkyl)C(O)aryl, or aryl, wherein the aryl groups are optionally substituted with 1, 2, 3, 4, or 5 groups that are independently $C_1$-$C_6$ alkyl, $C_1$-$C_6$ alkoxy, halogen, haloalkyl, haloalkoxy, or $NO_2$, or Z is —NHC(O)—($C_1$-$C_4$)alkyl-($C_3$-$C_7$)cycloalkyl, or —N($C_1$-$C_4$)alkyl-C(O)—($C_1$-$C_4$)alkyl-($C_3$-$C_7$)cycloalkyl.

50. A pharmaceutical composition comprising a compound of claim 49 and at least one pharmaceutically acceptable solvent, carrier, adjuvant or excipient.

\* \* \* \* \*